US010100088B2

(12) United States Patent
Deliencourt-Godefroy et al.

(10) Patent No.: US 10,100,088 B2
(45) Date of Patent: Oct. 16, 2018

(54) GLYCOPEPTIDE DERIVATIVES FOR THE PRESERVATION AND PROTECTION OF BIOLOGICAL MATERIALS AND MICROORGANISMS

(71) Applicant: TFCHEM, Val de Reuil (FR)

(72) Inventors: Geraldine Deliencourt-Godefroy, Bois d'Ennebourg (FR); Thibaut Martin, Rouen (FR)

(73) Assignee: TFCHEM (FR)

( * ) Notice: Subject to any disclaimer, the term of this patent is extended or adjusted under 35 U.S.C. 154(b) by 6 days.

(21) Appl. No.: 15/125,725

(22) PCT Filed: Mar. 17, 2015

(86) PCT No.: PCT/EP2015/055577
§ 371 (c)(1),
(2) Date: Sep. 13, 2016

(87) PCT Pub. No.: WO2015/140178
PCT Pub. Date: Sep. 24, 2015

(65) Prior Publication Data
US 2017/0015709 A1 Jan. 19, 2017

(30) Foreign Application Priority Data

Mar. 17, 2014 (EP) .................... 14305374

(51) Int. Cl.
| | |
|---|---|
| A01N 1/02 | (2006.01) |
| A61K 8/69 | (2006.01) |
| A61K 38/14 | (2006.01) |
| A61Q 19/08 | (2006.01) |
| C07H 7/02 | (2006.01) |
| C07K 9/00 | (2006.01) |
| A61K 31/7028 | (2006.01) |
| A61K 8/64 | (2006.01) |
| A61Q 19/00 | (2006.01) |
| C07H 15/04 | (2006.01) |
| C07H 15/18 | (2006.01) |
| C07K 5/06 | (2006.01) |
| C07K 5/062 | (2006.01) |

(52) U.S. Cl.
CPC ........... *C07K 9/001* (2013.01); *A01N 1/0226* (2013.01); *A61K 8/64* (2013.01); *A61K 8/69* (2013.01); *A61K 31/7028* (2013.01); *A61K 38/14* (2013.01); *A61Q 19/00* (2013.01); *A61Q 19/08* (2013.01); *C07H 7/02* (2013.01); *C07H 15/04* (2013.01); *C07H 15/18* (2013.01); *C07K 5/06052* (2013.01); *C07K 5/06191* (2013.01)

(58) Field of Classification Search
CPC ......... A01N 1/0226; A61K 8/69; A61K 8/72; A61K 31/7012; A61K 31/7028; A61K 38/14; A61Q 19/00; A61Q 19/08; C07H 7/02; C07H 15/18; C07K 9/001
See application file for complete search history.

(56) References Cited

FOREIGN PATENT DOCUMENTS

| | | |
|---|---|---|
| CA | 2653153 A1 | 8/2009 |
| FR | 2900405 A1 | 11/2007 |
| WO | WO-91/10361 A1 | 7/1991 |
| WO | WO-2004/014928 A1 | 2/2004 |
| WO | WO-2006/059227 A1 | 6/2006 |
| WO | WO-2007/125194 A1 | 11/2007 |
| WO | WO-2007/125203 A1 | 11/2007 |

(Continued)

OTHER PUBLICATIONS

Chaytor et al., "Assessing the ability of a short fluorinated carbohydrate derivative to inhibit ice recrystallization," Bioorganic & Medicinal Chemistry Letters, vol. 20, 2010, pp. 5251-5254.
Chorki et al., "First Synthesis of 10a-(Trifluoromethyl)deoxoartemisinin," Organic Letters, vol. 4, No. 5, 2002, pp. 757-759.

(Continued)

*Primary Examiner* — Jeffrey E. Russel
(74) *Attorney, Agent, or Firm* — Foley & Lardner LLP

(57) ABSTRACT

The present invention relates to a compound of the following formula (I):

$$R_{5a}HN \overset{O}{\underset{R_5}{\diagdown}} \underset{R_{6a}}{\overset{R_6}{\diagdown}} N \underset{O}{\overset{R_{7a}}{\diagdown}} \underset{R_7}{\diagdown} O-R_0 \quad (I)$$

in which at least one and only one group chosen among $R^5$, $R^6$ and $R^7$ is a group of the following formula:

[structure with $R$, $R_1$, $R_2$, $R_3$, $R_4$, $F_2$, $C$, $N$, $H$]

The present invention relates also to uses thereof for preservation and/or protection and/or regeneration of biological materials and or microorganisms and for cosmetic or dermatological applications such as anti-aging, skin protection and skin regeneration; to culture, storage and/or preservation media comprising such a compound; to cosmetic or dermatological compositions comprising such a compound; to processes for preparing such a compound; and to synthesis intermediates.

20 Claims, 8 Drawing Sheets

(56) References Cited

FOREIGN PATENT DOCUMENTS

WO    WO-2012/085221 A1    6/2012

OTHER PUBLICATIONS

Cuenca et al., "Addition of Ethyl Bromodifluoroacetate to Lactones: Reactivity and Stereoselectivity," Synlett, No. 17, 2005, pp. 2627-2630.
Eniade et al., "A Serendipitous Discovery of Antifreeze Protein-Specific Activity in C-Linked Antifreeze Glycoprotein Analogs", Cell Biochemistry and Biophysics, vol. 38, 2003, pp. 115-124.
Feeney et al., "Antifreeze Glycoprotiens from Polar Fish Blood," Annu. Rev. Biophys. Chem., vol. 15, 1986, pp. 59-78.
Leclere et al., "C-Linked Antifreeze Glycoprotein (C-AFGP) Analogues as Novel Cryoprotectants," Bioconjugate Chemistry, vol. 22, No. 9, 2011, pp. 1804-1810.
Liu et al., "C-linked Galactosyl Serine AFGP Analogues as Potent Recrystallization Inhibitors," Organic Letters, vol. 7, No. 12, 2005, pp. 2385-2388.
Liu et al., "In Vitro Studies of Antifreeze Glycoprotein (AFGP) and a C-Linked AFGP Analogue," Biomacromolecules, vol. 8, 2007, pp. 1456-1462.
Tam et al., "Solution Conformation of C-Linked Antifreeze Glycoprotein Analogues and Modulation of Ice Recrystallization," J. Am. Chem. Soc., vol. 131, 2009, pp. 15745-15753.
Yeh et al., "Antifreeze Proteins: Structures and Mechanisms of Function," vol. 96, No. 2, Chemical Reviews, 1996, pp. 601-618.

GLYCOPEPTIDE DERIVATIVES FOR THE PRESERVATION AND PROTECTION OF BIOLOGICAL MATERIALS AND MICROORGANISMS

The present invention relates to glycopeptide derivatives as well as their preparation processes, and their use as adjuvant for preservation and/or protection and/or regeneration of biological materials or microorganisms and for cosmetic applications such as anti-aging, skin protection or skin regeneration.

The preservation of biological materials has been the subject of intensive research. Antifreeze glycoproteins have been identified to have potential for such applications.

In the late 1960s Arthur DeVries showed that freezing resistance in Antarctic fish was due to blood serum glycoproteins that lowered their freezing temperature below that of the subzero sea surrounding them by inhibiting the growth of ice and protecting cells from hypothermic damages.

These glycoproteins called AFGPs for antifreeze glycoproteins have a structure, which consists of a number of repeating units of (Ala-Ala-Thr)n with the disaccharide β-D-galactosyl-(1→3)-α-N-acetyl-D-galactosamine being joined as a glycoside to the hydroxyl oxygen of the Thr residues.

There are eight distinct subtypes of glycopeptides, which range in molecular mass from 2.6 kDa (n=4) to 33.7 kDa (n=50). It has been observed that AFGPs protect species from cold induced damage.

Rubinsky et al. in WO 1991/010361 have underlined the effect of formulations containing antifreeze glycoproteins for these applications.

However, most of the studies performed in the above patent application or in the following publications (Chem. Rev. (1996), 96(2), 601-617; Ann. Rev. Biophys. Chem. (1986), 15, 59-78), mainly show a preservative effect in hypothermic conditions and especially in freezing and/or vitrification conditions.

In addition, natural AFGPs suffer from many disadvantages, which constitute limitations to their commercial applications. They are isolated from natural sources: fishes. 100 tons of fishes are necessary to extract 1 kg of AFGPs. The purification and isolation is difficult. The purity of the isolated compounds is very low (around 70%) and extracts are contaminated by other proteins and non-human antigenic materials. Besides it is only possible to isolate fractions with a range of molecular sizes and not a single compound. These compounds have high molecular mass (between 2.6 kDa and 33.7 kDa). They are unstable. They are highly sensitive to acid and base hydrolysis and undergo β-elimination at pH>9 and cleavage of the O-glycosidic bound in acidic conditions. They are also very sensitive to enzymatic hydrolysis which means that they also undergo cleavage of the O-glycosidic bound in biological media containing glycosidase. Such compounds have a short half-life and a low biodisponibility. They present also some cytotoxicity issues.

In order to solve some of these drawbacks and especially the stability issue, C-glycoside derivatives have been developed.

Ben and al. (Bioconjugate Chemistry (2011) 22 (9), 1804-1810; CA 2653153; Journal of the American Chemical Society (2009), 131(43), 15745-15753; Biomacromolecules (2007), 8 (5), 1456-1462; Organic Letters (2005) 7(12), 2385-2388; Cell Biochemistry and Biophysics (2003), 38(2), 115-124) have proposed $CH_2$-glycopeptide analogs to overcome such a stability issue and develop a family of compounds which shows antifreeze properties through TH (Thermal Hysteresis) and IRI (Ice Recristallization Inhibition). However none of these compounds has shown other potential for biological material protection against various stresses and they have only shown potential action on the physical properties of freezing. They have also underlined the need to have a polymeric structure, with repeating units of a glycotriaminoacid, to have efficacy.

Other derivatives corresponding to $CF_2$-glycopeptide analogs have been also described in WO 2006/059227 and WO 2007/125203 to overcome the issues of the natural compounds and the amazing properties of this class of compounds for biological material preservation were discovered. Indeed, these compounds, in addition to hypothermic preservation, showed preservative effects against different sorts of stress and do not require polymeric form to have efficacy. However, these compounds still undergo stability issues and decompose on the very sensitive $CF_2$—C(=O)—NH function by releasing a strong difluorinated acid that turns to be highly cytotoxic.

This instability is a major problem, especially as the compounds have to be neutralized in the biological media, and are particularly sensitive to the basic neutralisation.

There is thus a need for an adjuvant that allows improving the preservation/protection, or even regeneration, of biological material such as cells, tissues, body fluids and organs and of microorganisms by improving their quality and their shelf life, by protecting them from different stresses (such as oxidation, UV, radiations, pH, temperature (hypothermal to hyperthermal), starvation, chemical or bacterial contamination, etc.) or by recovering them after different stresses and/or by improving already existing protocols for biological material and microorganism preservation to render them more reproducible or easier to perform.

Such adjuvants will present also advantageously all the characteristics required to be included in cosmetic or dermatologic formulations in order to protect and/or preserve skin cells and tissues, or even to regenerate skin cells and tissues, and thus to lead to high potent product for anti-aging or skin protection, or even for skin regeneration.

The inventors of the present invention have recently identified a new family of $CF_2$-glycopeptides that solve the drawbacks related to the stability issues observed on the previous glycopeptide derivatives, that show properties for biological material and microorganism preservation and protection, and even regeneration, under different conditions, that have a potential for cosmetic or dermatologic applications (anti-aging, skin protection, skin regeneration, etc.) and that can be easily synthetize.

The present invention relates thus to a compound of the following formula (I):

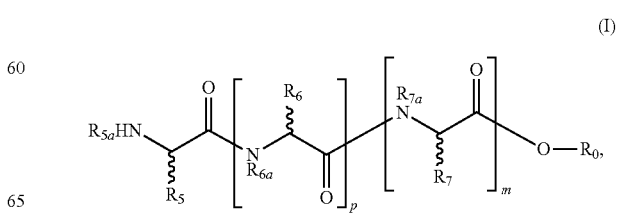

notably to a compound of the following formula (I'):

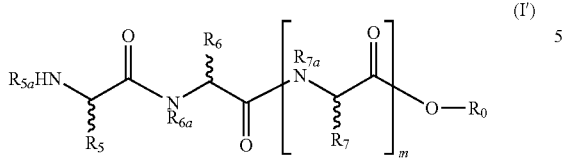

or a salt thereof, a solvate, a tautomer, a stereoisomer or a mixture of stereoisomers in any proportion, in particular a mixture of enantiomers, and particularly a racemate mixture, in which:

m represents 0 or 1,
p represents 0 or 1, and notably represents 1,
$R_0$ represents a hydrogen atom, a O-protecting group or a $(C_1-C_6)$alkyl, $(C_2-C_6)$alkenyl, $(C_2-C_6)$alkynyl, $(C_3-C_7)$ cycloalkyl, 5- to 7-membered heterocycloalkyl, aryl, heteroaryl, aryl-$(C_1-C_6)$alkyl, heteroaryl-$(C_1-C_6)$alkyl, $(C_1-C_6)$-alkyl-aryl or $(C_1-C_6)$-alkyl-heteroaryl group, this group being possibly substituted with one or more groups chosen among a halogen atom, $(C_1-C_6)$alkoxy, OH, COOH and CHO,
$R_{5a}$, $R_{6a}$ and $R_{7a}$ represent, independently from each other, a hydrogen or a N-protecting group, and
$R_5$, $R_6$ and $R_7$ represent, independently from each other, a hydrogen; a $(C_1-C_6)$alkyl optionally substituted by a $(C_1-C_6)$alkoxy or a $(C_1-C_6)$thioalkoxy; an aryl; an aryl-$(C_1-C_6)$alkyl optionally substituted by a $(C_1-C_6)$ alkoxy; or a group of the following formula:

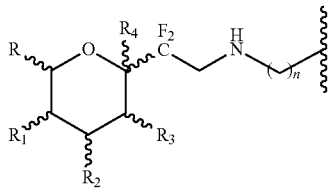

or $R_5$ and $R_{5a}$ and/or $R_6$ and $R_{6a}$ and/or $R_7$ and $R_{7a}$ form, with the nitrogen and carbon atoms carrying them, a pyrrolidine cycle

provided that at least one and only one group among $R_5$, $R_6$ and $R_7$ when m=p=1, or at least one and only one group among $R_5$ and $R_6$ when m=0 and p=1, or at least one and only one group among $R_5$ and $R_7$ when m=1 and p=0, or $R_5$ when m=p=0, represents a group of formula:

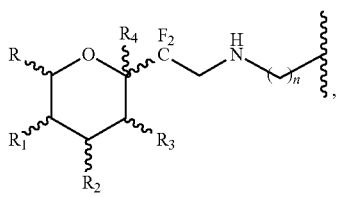

with
n representing an integer from 1 to 6,
R representing a hydrogen or fluorine atom or a $CH_3$, $CH_2F$, $CH_2OSiR^{a1}R^{b1}R^{c1}$, $CH_2OR_8$, $CH_2OC(O)R_9$, $CH_2OCO_2R_{10}$, $CH_2OC(O)NR_{11}R_{12}$, $CH_2OP(O)(OR_{13})_2$ or $CH_2OSO_3R_{14}$ group,
$R_1$ and $R_2$ representing, independently from one another, a fluorine atom or an $OSiR^{a2}R^{b2}R^{c2}$, $OR_{15}$, $OC(O)R_{16}$, $OCO_2R_{17}$, $OC(O)NR_{18}R_{19}$, $OP(O)(OR_{20})_2$ or $OSO_3R_{21}$ group,
$R_3$ representing a fluorine atom or an $OSiR^{a3}R^{b3}R^{c3}$, $OR_{22}$, $OC(O)R_{23}$, $OCO_2R_{24}$, $OCONR_{25}R_{26}$, $OP(O)(OR_{27})_2$, $OSO_3R_{28}$, $N_3$, phtalimidyl, $NR_{29}R_{30}$, $NR_{31}C(O)R_{32}$, $NR_{33}C(O)OR_{34}$, $N(C(O)R_{35})C(O)R_{36}$, $N(C(O)R_{37})C(O)OR_{38}$ and $N(C(O)OR_{39})C(O)OR_{40}$ group,
$R_4$ representing a hydrogen or halogen atom or an $OSiR^{a4}R^{b4}R^{c4}$, $OR_{41}$, $OC(O)R_{42}$, $OCO_2R_{43}$, $OCONR_{44}R_{45}$, $OP(O)(OR_{46})_2$, or $OSO_3R_{47}$ group, or R and $R_1$, together with the carbon atoms carrying them, form a cyclic acetal having the following formula:

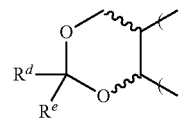

and/or ($R_1$ and $R_2$), ($R_2$ and $R_3$), and/or ($R_3$ and $R_4$), together with the carbon atoms carrying them, form a cyclic acetal having the following formula:

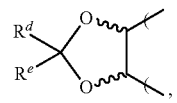

$R_8$, $R_{15}$, $R_{22}$ and $R_{41}$ representing, independently from one another, a hydrogen atom, a O-protecting group or a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, aryl-$(C_1-C_6)$alkyl, heteroaryl-$(C_1-C_6)$ alkyl, $(C_1-C_6)$-alkyl-aryl, $(C_1-C_6)$-alkyl-heteroaryl, saccharidic or polysaccharidic group, this group being possibly substituted with one or more groups chosen among a halogen atom, $(C_1-C_6)$alkoxy, OH, COOH and CHO; in particular a hydrogen atom, a $(C_1-C_6)$alkyl, aryl, aryl-$(C_1-C_6)$alkyl, saccharidic or polysaccharidic group, this group being possibly substituted with one or more groups chosen among a halogen atom, $(C_1-C_6)$ alkoxy, OH, COOH and CHO; and more particularly a hydrogen atom, a $(C_1-C_6)$alkyl, aryl or aryl-$(C_1-C_6)$ alkyl group, this group being possibly substituted with one or more groups chosen among a halogen atom, $(C_1-C_6)$alkoxy, OH, COOH and CHO,
$R_9$, $R_{10}$, $R_{16}$, $R_{17}$, $R_{23}$, $R_{24}$, $R_{32}$, $R_{34}$ to $R_{40}$, $R_{42}$ and $R_{43}$ representing, independently from one another, a $(C_1-C_6)$alkyl, $(C_2-C_6)$alkenyl, $(C_2-C_6)$alkynyl, $(C_3-C_7)$ cycloalkyl, 5- to 7-membered heterocycloalkyl, aryl, heteroaryl, aryl-$(C_1-C_6)$alkyl, heteroaryl-$(C_1-C_6)$alkyl, $(C_1-C_6)$-alkyl-aryl or $(C_1-C_6)$-alkyl-heteroaryl group, this group being possibly substituted with one or more groups chosen among a halogen atom, $(C_1-C_6)$alkoxy, OH, COOH and CHO; and in particular a $(C_1-C_6)$alkyl, aryl or aryl-$(C_1-C_6)$alkyl group, this group being possibly substituted with one or more groups chosen among a halogen atom, $(C_1-C_6)$alkoxy, OH, COOH and CHO, $R_{11}$, $R_{12}$, $R_{18}$, $R_{19}$, $R_{25}$, $R_{26}$, $R_{29}$ to $R_{31}$, $R_{33}$, $R_{44}$ and $R_{45}$ representing, independently from one another, a hydrogen atom or a $(C_1-C_6)$alkyl, $(C_2-C_6)$alkenyl, $(C_2-C_6)$ alkynyl, aryl, heteroaryl, aryl-$(C_1-C_6)$alkyl, heteroaryl-$(C_1-C_6)$alkyl, $(C_1-C_6)$-alkyl-aryl or $(C_1-C_6)$-alkyl-heteroaryl group, this group being possibly substituted with one or more groups chosen among a halogen atom, $(C_1-C_6)$alkoxy, OH, COOH and CHO; advantageously a hydrogen atom or a $(C_1-C_6)$alkyl, $(C_2-C_6)$alkenyl, $(C_2-C_6)$alkynyl, aryl-$(C_1-C_6)$alkyl, heteroaryl-$(C_1-C_6)$ alkyl group, this group being possibly substituted with one or more groups chosen among a halogen atom, $(C_1-C_6)$alkoxy, OH, COOH and CHO; and in particular a hydrogen atom or a $(C_1-C_6)$alkyl, aryl or aryl-$(C_1-C_6)$alkyl group, this group being possibly substituted with one or more groups chosen among a halogen atom, $(C_1-C_6)$alkoxy, OH, COOH and CHO, $R_{13}$, $R_{14}$, $R_{20}$, $R_{21}$, $R_{27}$, $R_{28}$, $R_{46}$ and $R_{47}$ representing, independently from one another, a hydrogen atom or a $(C_1-C_6)$alkyl group, $R^{a1}$ to $R^{a4}$, $R^{b1}$ to $R^{b4}$ and $R^{c1}$ to $R^{c4}$ representing, independently from one another, a $(C_1-C_6)$alkyl, aryl or aryl-$(C_1-C_6)$alkyl group, and $R^d$ and $R^e$ representing, independently from one another, a hydrogen atom or a $(C_1-C_6)$alkyl group.

In the context of the present invention, a salt can be:

(1) an acid addition salt formed with an inorganic acid such as hydrochloric, hydrobromic, sulfuric, nitric and phosphoric acid and the like; or formed with an organic acid such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic and trifluoroacetic acid and the like, or (2) a salt formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate, sodium hydroxide and the like.

In the context of the present invention, solvates of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

For the purpose of this invention, "tautomer" is intended to designate the various tautomer forms that the sugar of compound (I) may assume, namely a pyranose (6-membered ring), furanose (5-membered ring) or linear (open form) form. However, for practical reasons, the sugar of compound (I) is represented in the present description by its pyranose form.

However, the compounds of the invention can assume various tautomer forms only when the radical $R_4$ represents an OH group, $R_1$ having also to represent an OH group in order that the compounds of the invention can be in the furanose form.

Thus, for example, in the galactose series, the compounds of the invention might appear under the following various forms:

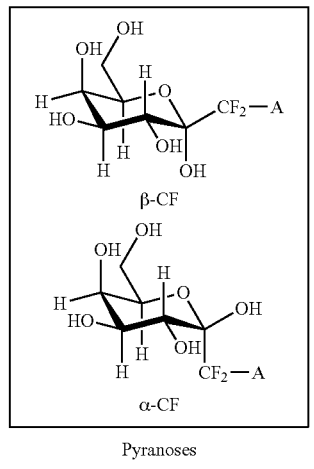

Pyranoses

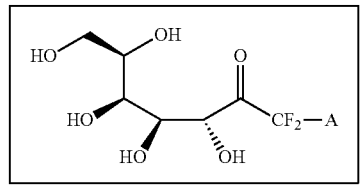

Linear

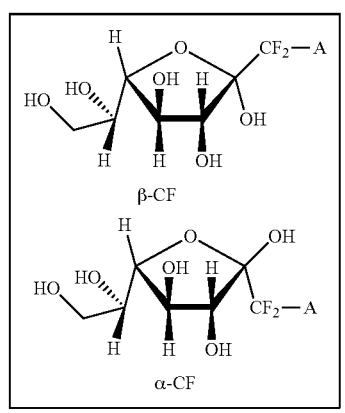

Furanoses

The group

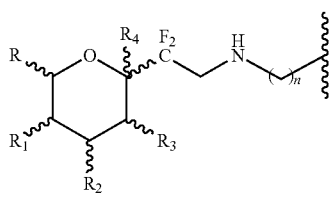

when $R_4=R_1=OH$ can thus assume the following tautomer forms:

pyranose form:

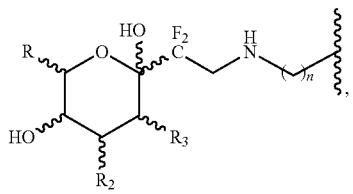

furanose form:

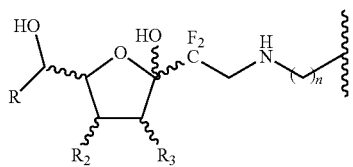

and
linear form:

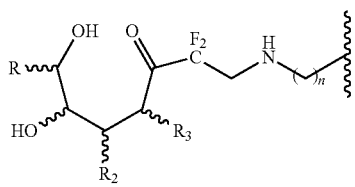

In the same way, the group

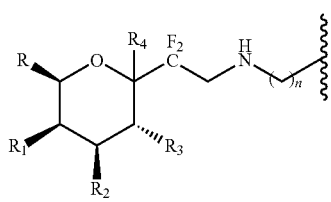

when $R_4=R_1=OH$ can thus assume the following tautomer forms:
pyranose form:

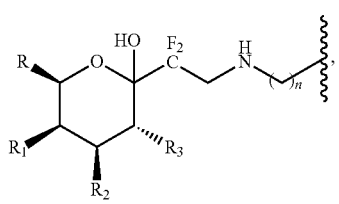

furanose form:

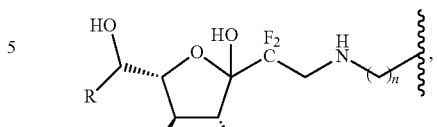

and
linear form:

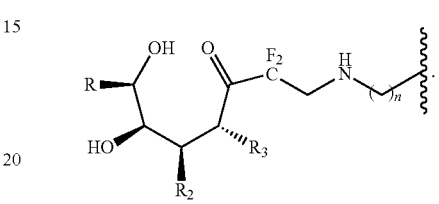

The anomeric carbon can appear in two different configurations in the closed pyranose and furanose forms.

The compounds of the invention can assume different tautomer forms which can be present in solution in equilibrium, with optionally a major tautomer form relatively to the other(s) tautomer form(s), or the compounds of the invention can assume only one tautomer form, such as only a pyranose form. This will depend notably on the nature of the medium, the temperature, the concentration of the compound, etc.

In this last case where the sugar assumes only one tautomer form, it is possible to block the configuration of the sugar in this tautomeric form when $R_4=OH$ is transformed, notably by substitution of the OH group or conversion in a hydrogen or halogen atom.

Within the meaning of this invention, "stereoisomers" is intended to designate diastereoisomers or enantiomers. These are therefore optical isomers. Stereoisomers which are not mirror images of one another are thus designated as "diastereoisomers," and stereoisomers which are non-superimposable mirror images are designated as "enantiomers".

Notably, the sugar moiety and the amino acid moieties of the compounds of the invention can belong to the D or L series.

A carbon atom bond to four non-identical substituents is called a "chiral centre".

An equimolar mixture of two enantiomers is called a racemate mixture.

The term "halogen" as used in the present invention refers to an atom of fluorine, bromine, chlorine or iodine. Advantageously, this is an atom of fluorine.

The term "$(C_1-C_6)$-alkyl" as used in the present invention refers to a saturated, linear or branched hydrocarbon chain comprising from 1 to 6 carbon atoms, in particular the methyl, ethyl, n-propyl, isopropyl, n-butyl, iso-butyl, sec-butyl, tert-butyl, n-pentyl, n-hexyl groups.

The term "$(C_2-C_6)$-alkenyl" as used in the present invention refers to a linear or branched hydrocarbon chain comprising at least one double bond and comprising from 2 to 6 carbon atoms, e.g., such as an ethenyl (vinyl) or propenyl (e.g. allyl) group.

The term "$(C_2-C_6)$-alkynyl" as used in the present invention refers to a linear or branched hydrocarbon chain comprising at least one triple bond and comprising from 2 to 6 carbon atoms, e.g., such as an ethynyl or propynyl group.

The term "($C_1$-$C_6$)alkoxy", as used in the present invention, refers to a ($C_1$-$C_6$)alkyl group as defined above bound to the molecule via an oxygen atom, including, but not limited to, methoxy, ethoxy, n-propoxy, iso-propoxy, n-butoxy, iso-butoxy, sec-butoxy, t-butoxy, n-pentoxy, n-hexoxy, and the like.

The term "($C_1$-$C_6$)thioalkoxy", as used in the present invention, refers to a ($C_1$-$C_6$)alkyl group as defined above bound to the molecule via a sulfur atom, including, but not limited to, thiomethoxy, thioethoxy, n-thiopropoxy, iso-thiopropoxy, n-thiobutoxy, iso-thiobutoxy, sec-thiobutoxy, t-thiobutoxy, n-thiopentoxy, n-thiohexoxy, and the like.

The term "($C_3$-$C_7$)-cycloalkyl" as used in the present invention refers to a saturated hydrocarbon ring comprising from 3 to 7, advantageously from 5 to 7, carbon atoms, in particular the cyclohexyl, cyclopentyl or cycloheptyl group.

The term "heterocycloalkyl" as used in the present invention refers to a saturated hydrocarbon ring having 5 to 7 members, in which one or more, advantageously one or two, carbon atoms have been each replaced with a heteroatom, such as sulphur, nitrogen or oxygen atoms. It can be notably a tetrahydrofuranyl, piperidinyl, pyrrolidinyl, tetrahydropyranyl, or 1,3-dioxolanyl group.

The term "aryl", as used in the present invention, refers to an aromatic hydrocarbon group comprising preferably 6 to 10 carbon atoms and comprising one or more fused rings, such as, for example, a phenyl or naphtyl group. Advantageously, it will be a phenyl group.

The term "heteroaryl" as used in the present invention refers to an aromatic group, preferably a 5- to 10-membered aromatic group, comprising one or more fused rings, in which the atoms of the ring(s) consist of one or more, advantageously 1 to 4, and more advantageously 1 or 2, heteroatoms, such as a nitrogen, oxygen or sulphur atom, the remainder being carbon atoms. A heteroaryl group can be notably a thienyl, furanyl, pyrrolyl, pyridyl, pyrimidyl, pyrazolyl, imidazolyl, tetrazolyl or indyl group.

The term "aryl-($C_1$-$C_6$)-alkyl" as used in the present invention refers to any aryl group as defined above, which is bound to the molecule by means of a ($C_1$-$C_6$)-alkyl group as defined above. In particular, it can be a benzyl group.

The term "heteroaryl-($C_1$-$C_6$)-alkyl" as used in the present invention refers to mean a heteroaryl group as defined above, which is bound to the molecule by means of a ($C_1$-$C_6$)-alkyl group as defined above.

The term "($C_1$-$C_6$)-alkyl-aryl" as used in the present invention refers to a ($C_1$-$C_6$)-alkyl group as defined above, which is bound to the molecule by means of an aryl group as defined above. In particular, it can be a methylphenyl group.

The term "($C_1$-$C_6$)-alkyl-heteroaryl" as used in the present invention refers to a ($C_1$-$C_6$)-alkyl group as defined above, which is bound to the molecule by means of a heteroaryl group as defined above.

The term "trialkylsilyl group", as used in the present invention, refers to a group —Si$Alk_1Alk_2Alk_3$ in which $Alk_1$, $Alk_2$ and $Alk_3$, identical or different, represent a ($C_1$-$C_6$)-alkyl group as defined above. For example, it can be a trimethylsilyl or triethylsilyl group.

The term "protecting group", as used in the present invention, refers to a chemical group which selectively blocks a reactive site in a multifunctional compound so as to allow selectively performing a chemical reaction on another unprotected reactive site.

The term "N-protecting group", as used in the present invention, refers to those groups intended to protect an amine function against undesirable reactions during synthetic procedures. Commonly used N-protecting groups are disclosed in Greene, "Protective Groups In Organic Synthesis," (John Wiley & Sons, New York (1981)). An amine function protected by a N-protecting group can be a carbamate, an amide, a sulfonamide, an N-alkyl derivative, an amino acetal derivative, a N-benzyl derivative, an imine derivative, an enamine derivative or a N-heteroatom derivative. In particular, N-protecting groups can be formyl; an aryl, such as a phenyl, optionally substituted with one or several methoxy groups such as p-methoxyphenyl (PMP); an aryl-($C_1$-$C_6$)alkyl, such as a benzyl, the aryl moiety being optionally substituted with one or several methoxy groups, such as benzyl (Bn), p-methoxybenzyl (PMB) or 3,4-dimethoxybenzyl (DMPM); —CO—$R_{GP1}$ such as acetyl (Ac), pivaloyl (Piv or Pv), benzoyl (Bz) or p-methoxybenzylcarbonyl (Moz); —$CO_2$—$R_{GP1}$ such as tbutyloxycarbonyl (Boc), trichloroethoxycarbonyl (TROC), allyloxycarbonyl (Alloc), benzyloxycarbonyl (Cbz or Z) or 9-fluorenylmethyloxycarbonyl (Fmoc); —$SO_2$—$R_{GP1}$ such as phenylsulfonyl, tosyl (Ts or Tos) or 2-nitrobenzenesulfonyl (also called nosyl—Nos or Ns); and the like, with $R_{GP1}$ representing a ($C_1$-$C_6$)alkyl optionally substituted with one or several halogen atoms such as F or Cl; a ($C_2$-$C_6$)alkenyl such as an allyl; an aryl, such as a phenyl, optionally substituted with one or several groups chosen among OMe (methoxy) and $NO_2$ (nitro); an aryl-($C_1$-$C_6$)alkyl, such as a benzyl, the aryl moiety being optionally substituted with one or several methoxy groups; or a 9-fluorenylmethyl group.

The N-protecting group can be in particular —$CO_2$—$R_{GP1}$ such as Cbz, Boc or Fmoc, notably Cbz.

The term "O-Protecting group" as used in the present invention refers to a substituent which protects hydroxyl groups against undesirable reactions during synthetic procedures such as those O-protecting groups disclosed in Greene, "Protective Groups In Organic synthesis", (John Wiley & Sons, New York (1981)). A hydroxyl group protected by a O-protecting group can be for example an ether, an ester, a carbonate, an acetal and the like. In particular, O-protecting groups can be a ($C_1$-$C_6$)alkyl optionally substituted with one or several (notably 1 to 3) halogen atoms (such as chlorine atoms), such as methyl, ethyl, tert-butyl or 2,2,2-trichloroethyl; an aryl-($C_1$-$C_6$)alkyl, such as a benzyl, the aryl moiety being optionally substituted with one or several methoxy groups, such as benzyl (Bn) or p-methoxybenzyl (PMB); a trityl group of formula —$CAr_1Ar_2Ar_3$ such as triphenylmethyl (also called trityl—Tr), (4-methoxyphenyl)diphenylmethyl (also called methoxytrityl—NMT) or bis-(4-methoxyphenyl)phenylmethyl (also called dimethoxytrityl—DMT); a substituted methyl group of formula —$CH_2OR_{GP2}$ or —$CH_2SR_{GP2}$ (in particular —$CH_2OR_{GP2}$), for example, methoxymethyl (MOM), benzyloxymethyl, 2-methoxyethoxymethyl (MEM), 2-(trimethylsilyl)ethoxymethyl or methylthiomethyl; a substituted ethyl group of formula —$CH_2CH_2OR_{GP2}$ or —$CH_2CH_2SR_{GP2}$ (in particular —$CH_2CH_2OR_{GP2}$), for example, ethoxyethyl (EE); a silyl group of formula —$SiR_{GP3}R_{GP4}R_{GP5}$, for example, trimethylsilyl (TMS), triethylsilyl (TES), t-butyldimethylsilyl (TBS or TBDMS) and t-butyldiphenylsilyl (TBDPS); carbonylated groups of formula —CO—$R_{GP6}$ such as acetyl (Ac), pivaloyl (Piv or Pv) or benzoyl (Bz) or of formula —$CO_2$—$R_{GP7}$ such as allyloxycarbonyl (Alloc) or 9-fluorenylmethyloxycarbonyl (Fmoc); or a tetrahydropyranyl

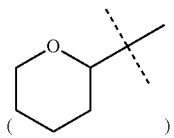

(THP) or tetrahydrofuranyl

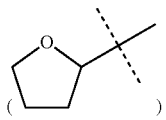

group;

with $Ar_1$, $Ar_2$ and $Ar_3$ representing, independently from one another, n aryl, such as a phenyl, optionally substituted with one or several methoxy groups; $R_{GP2}$ representing a ($C_1$-$C_6$)alkyl (such as methyl or ethyl) optionally substituted with an aryl (such as phenyl), a ($C_1$-$C_6$)alkoxy (such as methoxy) or a trialkylsilyl group (such as $SiMe_3$); $R_{GP3}$, $R_{GP4}$ and $R_{GP5}$ representing, independently from one another, a ($C_1$-$C_6$)alkyl or aryl (such as phenyl) group; and $R_{GP6}$ and $R_{GP7}$ representing, independently of each other, a ($C_1$-$C_6$)alkyl, a ($C_2$-$C_6$)alkenyl, an aryl, an aryl-($C_1$-$C_6$)alkyl or a 9-fluorenylmethyl group.

The O-protecting group can be in particular a ($C_1$-$C_6$) alkyl group or an aryl-($C_1$-$C_6$)alkyl group (such as a benzyl).

The term "saccharide" as used in the present invention refers to erythrose, threose, ribose, arabinose, xylose, lyxose, allose, altrose, glucose, mannose, gulose, idose, galactose, talose, erythrulose, ribulose, xylulose, psicose, fructose, sorbose or tagatose, in D or L form.

The term "saccharidic group" as used in the present invention refers to a saccharide as defined above bond to the molecule by means of its oxygen atom present at the anomeric centre.

The term "polysaccharide" as used in the present invention refers to a chain comprising at least 2, and preferably 2 to 10 saccharides as defined above bound together by means of an oxygen bridge formed between the OH function at the anomeric position of a saccharide and the OH function not at the anomeric position of another saccharide.

The term "polysaccharidic group" as used in the present invention refers to a polysaccharide as defined above bond to the molecule by means of the oxygen atom present at the anomeric centre of the terminal saccharide.

The compounds according to the invention can have the following formula (Ia):

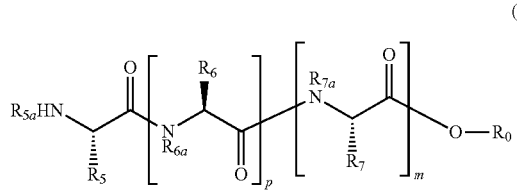

(Ia)

and notably can have the following formula (Ia'):

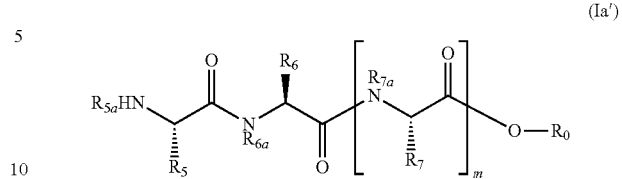

(Ia')

with m, p, $R_0$, $R_5$, $R_{5a}$, $R_6$, $R_{6a}$, $R_7$ and $R_{7a}$ as defined above, and notably with p=1.

The compound of formula (I) can be advantageously in the form of an acid addition salt, the acid being notably hydrochloric acid. The acid can be also acetic acid.

The value m can be in particular 1. In particular, m=p=1.

According to a particular embodiment, $R_5$, $R_6$ and $R_7$ represent, independently from each other, H, $CH_3$, $CH(CH_3)_2$, $CH_2CH(CH_3)_2$, $CH(CH_3)CH_2CH_3$, $CH_2Ph$, $CH_2PhOCH_3$ (in particular $CH_2Ph$-$pOCH_3$), $CH_2CH_2SCH_3$ or a group of the following formula:

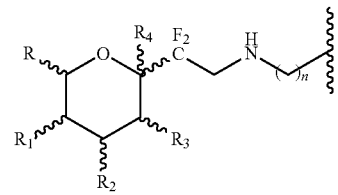

or $R_5$ and $R_{5a}$ and/or $R_6$ and $R_{6a}$ and/or $R_7$ and $R_{7a}$ form, with the nitrogen and carbon atoms carrying them, a pyrrolidine cycle

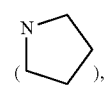, provided that at least one and only one group among $R_5$, $R_6$ and $R_7$ when m=p=1, or at least one and only one group among $R_5$ and $R_6$ when m=0 and p=1, or at least one and only one group among $R_5$ and $R_7$ when m=1 and p=0, or $R_5$ when m=p=0, represents a group of formula:

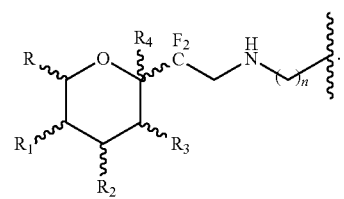

According to another particular embodiment, $R_5$, $R_6$ and $R_7$ represent, independently from each other, a hydrogen atom, a ($C_1$-$C_6$)alkyl, an aryl, an aryl-($C_1$-$C_6$)alkyl, the aryl moiety of the aryl or aryl-($C_1$-$C_6$)alkyl group being optionally substituted by an OH or ($C_1$-$C_6$)alkoxy group, or a group of the following formula:

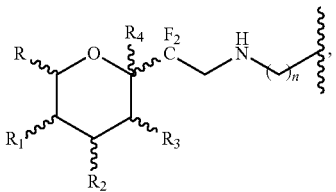

or $R_5$ and $R_{5a}$ and/or $R_6$ and $R_{6a}$ and/or $R_7$ and $R_{7a}$ form, with the nitrogen and carbon atoms carrying them, a pyrrolidine cycle

provided that at least one and only one group among $R_5$, $R_6$ and $R_7$ when m=p=1, or at least one and only one group among $R_5$ and $R_6$ when m=0 and p=1, or at least one and only one group among $R_5$ and $R_7$ when m=1 and p=0, or $R_5$ when m=p=0, represents a group of formula:

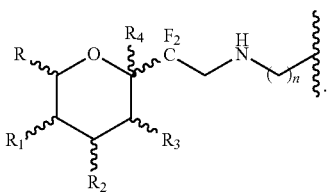

According to another particular embodiment, $R_5$, $R_6$ and $R_7$ represent, independently from each other, a hydrogen atom; a $(C_1-C_6)$alkyl; an aryl; an aryl-$(C_1-C_6)$alkyl optionally substituted by a $(C_1-C_6)$alkoxy group, or a group of the following formula:

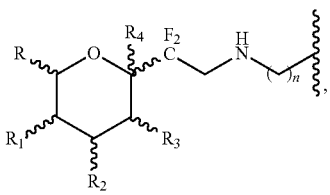

or $R_5$ and $R_{5a}$ and/or $R_6$ and $R_{6a}$ and/or $R_7$ and $R_{7a}$ form, with the nitrogen and carbon atoms carrying them, a pyrrolidine cycle

provided that at least one and only one group among $R_5$, $R_6$ and $R_7$ when m=p=1, or at least one and only one group among $R_5$ and $R_6$ when m=0 and p=1, or at least one and only one group among $R_5$ and $R_7$ when m=1 and p=0, or $R_5$ when m=p=0, represents a group of formula:

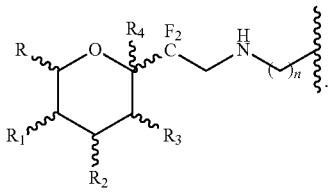

According to still another particular embodiment, $R_5$, $R_6$ and $R_7$ represent, independently from each other, a hydrogen atom, a $(C_1-C_6)$alkyl (such as methyl) or a group of the following formula:

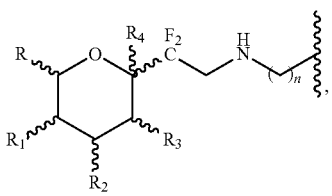

or $R_5$ and $R_{5a}$ and/or $R_6$ and $R_{6a}$ and/or $R_7$ and $R_{7a}$ form, with the nitrogen and carbon atoms carrying them, a pyrrolidine cycle

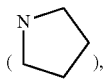

provided that at least one and only one group among $R_5$, $R_6$ and $R_7$ when m=p=1, or at least one and only one group among $R_5$ and $R_6$ when m=0 and p=1, or at least one and only one group among $R_5$ and $R_7$ when m=1 and p=0, or $R_5$ when m=p=0, represents a group of formula:

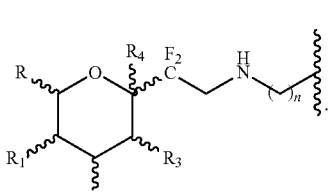

According to still another particular embodiment, $R_5$, $R_6$ and $R_7$ represent, independently from each other, a $(C_1-C_6)$ alkyl (such as methyl) or a group of the following formula:

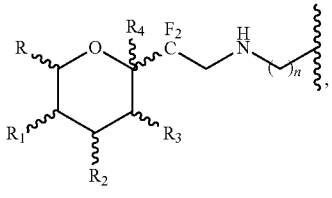

provided that at least one and only one group among $R_5$, $R_6$ and $R_7$ when m=p=1, or at least one and only one group among $R_5$ and $R_6$ when m=0 and p=1, or at least one and only one group among $R_5$ and $R_7$ when m=1 and p=0, or $R_5$ when m=p=0, represents a group of formula:

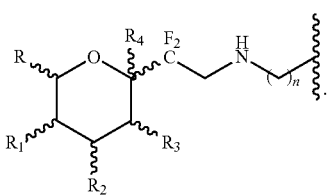

When $R_5$ represents

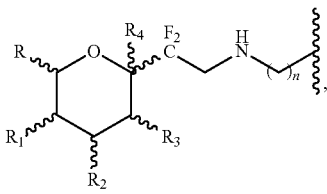

$R_{5a}$ represents a hydrogen or a N-protecting group, notably a hydrogen atom.
Then:
- when m=p=1, $R_7$ and $R_7$ represent, independently from each other, a hydrogen; a $(C_1-C_6)$alkyl optionally substituted by a $(C_1-C_6)$alkoxy or a $(C_1-C_6)$thioalkoxy; an aryl; or an aryl-$(C_1-C_6)$alkyl optionally substituted by a $(C_1-C_6)$alkoxy; notably H, $CH_3$, $CH(CH_3)_2$, $CH_2CH(CH_3)_2$, $CH(CH_3)CH_2CH_3$, $CH_2Ph$, $CH_2PhOCH_3$ or $CH_2CH_2SCH_3$, and $R_{6a}$ and $R_{7a}$ represent a hydrogen or a N-protecting group, notably a hydrogen atom,
- or $R_7$ and $R_{6a}$ and/or $R_7$ and $R_{7a}$ form, with the nitrogen and carbon atoms carrying them, a pyrrolidine cycle

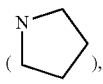

- when m=0 and p=1, $R_7$ is absent and $R_7$ represents independently from each other a hydrogen; a $(C_1-C_6)$alkyl optionally substituted by a $(C_1-C_6)$alkoxy or a $(C_1-C_6)$thioalkoxy; an aryl; or an aryl-$(C_1-C_6)$alkyl optionally substituted by a $(C_1-C_6)$alkoxy; notably H, $CH_3$, $CH(CH_3)_2$, $CH_2CH(CH_3)_2$, $CH(CH_3)CH_2CH_3$, $CH_2Ph$, $CH_2PhOCH_3$ or $CH_2CH_2SCH_3$, and $R_{6a}$ represents a hydrogen or a N-protecting group, notably a hydrogen atom,
- or $R_6$ and $R_{6a}$ form, with the nitrogen and carbon atoms carrying them, a pyrrolidine cycle

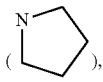

- when m=1 and p=0, $R_6$ is absent and $R_7$ represents independently from each other a hydrogen; a $(C_1-C_6)$ alkyl optionally substituted by a $(C_1-C_6)$alkoxy or a $(C_1-C_6)$thioalkoxy; an aryl; or an aryl-$(C_1-C_6)$alkyl optionally substituted by a $(C_1-C_6)$alkoxy; notably H, $CH_3$, $CH(CH_3)_2$, $CH_2CH(CH_3)_2$, $CH(CH_3)CH_2CH_3$, $CH_2Ph$, $CH_2PhOCH_3$ or $CH_2CH_2SCH_3$, and $R_{7a}$ represents a hydrogen or a N-protecting group, notably a hydrogen atom,
- or $R_7$ and $R_{7a}$ form, with the nitrogen and carbon atoms carrying them, a pyrrolidine cycle

- when m=p=0, $R_6$ and $R_7$ are absent.

When m=p=1, $R_6$ and $R_7$ can also represent, independently from each other, a hydrogen, a $(C_1-C_6)$alkyl, an aryl or an aryl-$(C_1-C_6)$alkyl; notably a $(C_1-C_6)$alkyl, an aryl or an aryl-$(C_1-C_6)$alkyl; in particular a $(C_1-C_6)$alkyl (such as methyl), and $R_{6a}$ and $R_{7a}$ represent a hydrogen or a N-protecting group, notably a hydrogen atom.

When m=0 and p=1, $R_6$ can also represent, independently from each other, a hydrogen, a $(C_1-C_6)$alkyl, an aryl or an aryl-$(C_1-C_6)$alkyl; notably a $(C_1-C_6)$alkyl, an aryl or an aryl-$(C_1-C_6)$alkyl; in particular a $(C_1-C_6)$alkyl (such as methyl), and $R_{6a}$ represents a hydrogen or a N-protecting group, notably a hydrogen atom.

When m=1 and p=0, $R_7$ can also represent, independently from each other, a hydrogen, a $(C_1-C_6)$alkyl, an aryl or an aryl-$(C_1-C_6)$alkyl; notably a $(C_1-C_6)$alkyl, an aryl or an aryl-$(C_1-C_6)$alkyl; in particular a $(C_1-C_6)$alkyl (such as methyl), and $R_{7a}$ represents a hydrogen or a N-protecting group, notably a hydrogen atom.

When $R_6$ represents

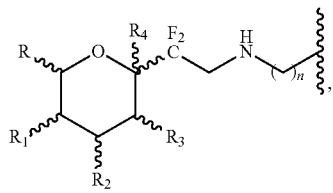

$R_{6a}$ represents a hydrogen or a N-protecting group, notably a hydrogen atom, and p represents 1.
Then:
- when m=1, $R_5$ and $R_7$ represent, independently from each other, a hydrogen; a $(C_1-C_6)$alkyl optionally substituted by a $(C_1-C_6)$alkoxy or a $(C_1-C_6)$thioalkoxy; an aryl; or an aryl-$(C_1-C_6)$alkyl optionally substituted by a $(C_1-C_6)$alkoxy; notably H, $CH_3$, $CH(CH_3)_2$, $CH_2CH(CH_3)_2$, $CH(CH_3)CH_2CH_3$, $CH_2Ph$, $CH_2PhOCH_3$ or $CH_2CH_2SCH_3$, and $R_{5a}$ and $R_{7a}$ represent a hydrogen or a N-protecting group, notably a hydrogen atom,
- or $R_5$ and $R_{5a}$ and/or $R_7$ and $R_{7a}$ form, with the nitrogen and carbon atoms carrying them, a pyrrolidine cycle

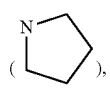

and
- when m=0, $R_7$ is absent and $R_5$ represents independently from each other a hydrogen; a $(C_1-C_6)$alkyl optionally substituted by a $(C_1-C_6)$alkoxy or a $(C_1-C_6)$thioalkoxy; an aryl; or an aryl-$(C_1-C_6)$alkyl optionally substituted by a $(C_1-C_6)$alkoxy; notably H, $CH_3$, $CH(CH_3)_2$, $CH_2CH(CH_3)_2$, $CH(CH_3)CH_2CH_3$, $CH_2Ph$, CH$_2$PhOCH$_3$ or CH$_2$CH$_2$SCH$_3$, and R$_{5a}$ represents a hydrogen or a N-protecting group, notably a hydrogen atom, or R$_5$ and R$_{5a}$ form, with the nitrogen and carbon atoms carrying them, a pyrrolidine cycle

.

When m=1, R$_5$ and R$_7$ can also represent, independently from each other, a hydrogen, a (C$_1$-C$_6$)alkyl, an aryl or an aryl-(C$_1$-C$_6$)alkyl; notably a (C$_1$-C$_6$)alkyl, an aryl or an aryl-(C$_1$-C$_6$)alkyl; in particular a (C$_1$-C$_6$)alkyl (such as methyl), and R$_{5a}$ and R$_{7a}$ represent a hydrogen or a N-protecting group, notably a hydrogen atom.

When m=0, R$_5$ can also represent, independently from each other, a hydrogen, a (C$_1$-C$_6$)alkyl, an aryl or an aryl-(C$_1$-C$_6$)alkyl; notably a (C$_1$-C$_6$)alkyl, an aryl or an aryl-(C$_1$-C$_6$)alkyl; in particular a (C$_1$-C$_6$)alkyl (such as methyl), and R$_{5a}$ represents a hydrogen or a N-protecting group, notably a hydrogen atom.

When R$_7$ represents

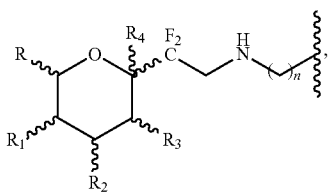

R$_{7a}$ represents a hydrogen or a N-protecting group, notably a hydrogen atom, and m represent 1. Advantageously, p=1. Then:

when p=1, R$_5$ and R$_6$ represents independently from each other a hydrogen; a (C$_1$-C$_6$)alkyl optionally substituted by a (C$_1$-C$_6$)alkoxy or a (C$_1$-C$_6$)thioalkoxy; an aryl; or an aryl-(C$_1$-C$_6$)alkyl optionally substituted by a (C$_1$-C$_6$)alkoxy; notably H, CH$_3$, CH(CH$_3$)$_2$, CH$_2$CH(CH$_3$)$_2$, CH(CH$_3$)CH$_2$CH$_3$, CH$_2$Ph, CH$_2$PhOCH$_3$ or CH$_2$CH$_2$SCH$_3$, and R$_{5a}$ and R$_{6a}$ represent a hydrogen or a N-protecting group, notably a hydrogen atom, or R$_5$ and R$_{5a}$ and/or R$_6$ and R$_{6a}$ form, with the nitrogen and carbon atoms carrying them, a pyrrolidine cycle

.

when p=0, R$_6$ is absent and R$_5$ represents a hydrogen; a (C$_1$-C$_6$)alkyl optionally substituted by a (C$_1$-C$_6$)alkoxy or a (C$_1$-C$_6$)thioalkoxy; an aryl; or an aryl-(C$_1$-C$_6$)alkyl optionally substituted by a (C$_1$-C$_6$)alkoxy; notably H, CH$_3$, CH(CH$_3$)$_2$, CH$_2$CH(CH$_3$)$_2$, CH(CH$_3$)CH$_2$CH$_3$, CH$_2$Ph, CH$_2$PhOCH$_3$ or CH$_2$CH$_2$SCH$_3$, and R$_{5a}$ represent a hydrogen or a N-protecting group, notably a hydrogen atom, or R$_5$ and R$_{5a}$ form, with the nitrogen and carbon atoms carrying them, a pyrrolidine cycle

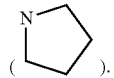.

When p=1, R$_5$ and R$_6$ can also represent, independently from each other, a hydrogen, a (C$_1$-C$_6$)alkyl, an aryl or an aryl-(C$_1$-C$_6$)alkyl; notably a (C$_1$-C$_6$)alkyl, an aryl or an aryl-(C$_1$-C$_6$)alkyl; in particular a (C$_1$-C$_6$)alkyl (such as methyl), and R$_{5a}$ and R$_{6a}$ represent a hydrogen or a N-protecting group, notably a hydrogen atom.

When p=0, R$_5$ can also represent a hydrogen, a (C$_1$-C$_6$)alkyl, an aryl or an aryl-(C$_1$-C$_6$)alkyl; notably a (C$_1$-C$_6$)alkyl, an aryl or an aryl-(C$_1$-C$_6$)alkyl; in particular a (C$_1$-C$_6$)alkyl (such as methyl), and R$_{5a}$ represent a hydrogen or a N-protecting group, notably a hydrogen atom.

According to a particular embodiment, when m=p=1, two groups chosen among R$_5$, R$_6$ and R$_7$ represent, independently from each other, a hydrogen; a (C$_1$-C$_6$)alkyl optionally substituted by a (C$_1$-C$_6$)alkoxy or a (C$_1$-C$_6$)thioalkoxy; an aryl; or an aryl-(C$_1$-C$_6$)alkyl optionally substituted by a (C$_1$-C$_6$)alkoxy; notably H, CH$_3$, CH(CH$_3$)$_2$, CH$_2$CH(CH$_3$)$_2$, CH(CH$_3$)CH$_2$CH$_3$, CH$_2$Ph, CH$_2$PhOCH$_3$ (in particular CH$_2$Ph-pOCH$_3$) or CH$_2$CH$_2$SCH$_3$.

The remaining group represents then a group of formula:

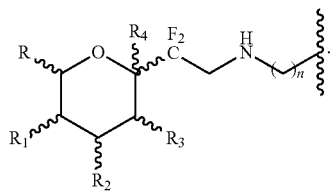

According to another particular embodiment, when m=0 and p=1, one of R$_5$ and R$_6$ represents a hydrogen; a (C$_1$-C$_6$)alkyl optionally substituted by a (C$_1$-C$_6$)alkoxy or a (C$_1$-C$_6$)thioalkoxy; an aryl; or an aryl-(C$_1$-C$_6$)alkyl optionally substituted by a (C$_1$-C$_6$)alkoxy; notably H, CH$_3$, CH(CH$_3$)$_2$, CH$_2$CH(CH$_3$)$_2$, CH(CH$_3$)CH$_2$CH$_3$, CH$_2$Ph, CH$_2$PhOCH$_3$ (in particular CH$_2$Ph-pOCH$_3$) or CH$_2$CH$_2$SCH$_3$.

The remaining group represents then a group of formula:

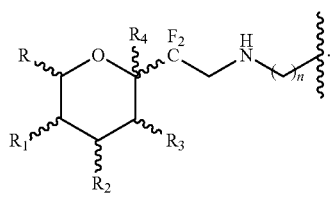

This particular embodiment corresponds also to the particular embodiment, when m=1 and p=0, one of R$_5$ and R$_7$ represents a hydrogen; a (C$_1$-C$_6$)alkyl optionally substituted by a (C$_1$-C$_6$)alkoxy or a (C$_1$-C$_6$)thioalkoxy; an aryl; or an aryl-(C$_1$-C$_6$)alkyl optionally substituted by a (C$_1$-C$_6$)alkoxy; notably H, CH$_3$, CH(CH$_3$)$_2$, CH$_2$CH(CH$_3$)$_2$, CH(CH$_3$)CH$_2$CH$_3$, CH$_2$Ph, CH$_2$PhOCH$_3$ (in particular CH$_2$Ph-pOCH$_3$) or CH$_2$CH$_2$SCH$_3$, and the remaining group represents then a group of formula:

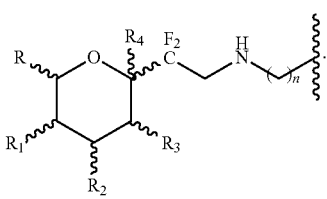

According to another particular embodiment, when m=p=0, $R_5$ represents a group of formula:

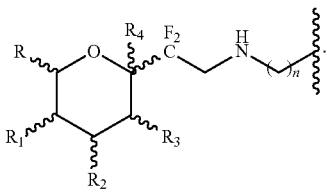

When $R_{5a}$, $R_{6a}$ and/or $R_{7a}$ represent a N-protecting group, the N-protecting group is as defined above. It can be in particular an aryl, such as a phenyl, optionally substituted with one or several methoxy groups; an aryl-($C_1$-$C_6$)alkyl, such as a benzyl, the aryl moiety being optionally substituted with one or several methoxy groups; —CO—$R_{GP1}$; —$CO_2$—$R_{GP1}$; or —$SO_2$—$R_{GP1}$, with $R_{GP1}$ as defined above. The N-protecting group can be notably a —$CO_2$—$R_{GP1}$ group such as Cbz, Boc or Fmoc, notably Cbz.

Thus, $R_{5a}$, $R_{6a}$ and $R_{7a}$ represent, independently from one another, a hydrogen or a N-protecting group such as —$CO_2$—$R_{GP1}$, notably a hydrogen, or $R_5$ and $R_{5a}$ and/or $R_6$ and $R_{6a}$ and/or $R_7$ and $R_{7a}$ form, with the nitrogen and carbon atoms carrying them, a pyrrolidine cycle

In particular, $R_{5a}$, $R_{6a}$ and $R_{7a}$ each represent a hydrogen. The group of formula:

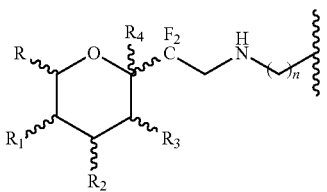

can have in particular the following stereochemistry:

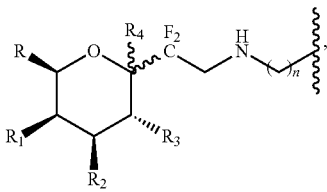

for example

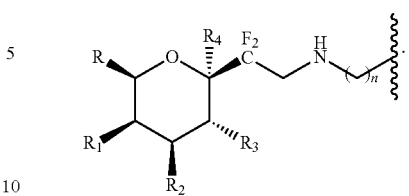

The value n can be in particular 2, 3 or 4, notably 4.

$R_0$ can represent notably a hydrogen atom or a O-protecting group (for example a aryl-($C_1$-$C_6$)alkyl group such as Bn), in particular a hydrogen atom.

$R_0$ can also represent a hydrogen atom or a ($C_1$-$C_6$)alkyl, aryl or aryl-($C_1$-$C_6$)alkyl group, this group being unsubstituted or substituted with one or more groups chosen among a halogen atom, ($C_1$-$C_6$)alkoxy, OH, COOH and CHO, notably unsubstituted.

$R_0$ can represent in particular a hydrogen atom or a ($C_1$-$C_6$)alkyl or aryl-($C_1$-$C_6$)alkyl group, notably H, Bn or Et.

R can represent a $CH_2OSiR^{a1}R^{b1}R^{c1}$, $CH_2OR_8$, $CH_2OC(O)R_9$, $CH_2OCO_2R_{10}$, $CH_2OC(O)NR_{11}R_{12}$, $CH_2OP(O)(OR_{13})_2$ or $CH_2OSO_3R_{14}$ group, advantageously a $CH_2OSiR^{a1}R^{b1}R^{c1}$, $CH_2OR_8$ or $CH_2OC(O)R_9$ group, more advantageously a $CH_2OR_8$ or $CH_2OC(O)R_9$ group, and even more advantageously a $CH_2OR_8$ group.

R can represent in particular a $CH_2OR_8$ group with $R_8$ representing a hydrogen atom, a O-protecting group or a ($C_1$-$C_6$)-alkyl, aryl or aryl-($C_1$-$C_6$)-alkyl group; or a $CH_2OC(O)R_9$ group with $R_9$ representing a ($C_1$-$C_6$)-alkyl, aryl or aryl-($C_1$-$C_6$)-alkyl group.

R can represent more particularly a $CH_2OR_8$ group with $R_8$ representing a hydrogen atom or a O-protecting group. For instance, R can represent a $CH_2OH$ or $CH_2OBn$ group.

$R_1$ and $R_2$ can represent, independently from one another, an $OSiR^{a2}R^{b2}R^{c2}$, $OR_{15}$, $OC(O)R_{16}$, $OCO_2R_{17}$ or $OC(O)NR_{18}R_{19}$ group, advantageously an $OSiR^{a2}R^{b2}R^{c2}$, $OR_{15}$ or $OC(O)R_{16}$ group, more advantageously an $OR_{15}$ or $OC(O)R_{16}$ group, and even more advantageously an $OR_{15}$ group.

$R_1$ and $R_2$ can represent in particular, independently from one another, an $OR_{15}$ group with $R_{15}$ representing a hydrogen atom, a O-protecting group or a ($C_1$-$C_6$)-alkyl, aryl or aryl-($C_1$-$C_6$)-alkyl group; or an $OC(O)R_{16}$ group $R_{16}$ representing a ($C_1$-$C_6$)-alkyl, aryl or aryl-($C_1$-$C_6$)-alkyl group.

$R_1$ and $R_2$ can represent more particularly, independently from one another, an $OR_{15}$ group with $R_{15}$ representing a hydrogen atom or a O-protecting group. For instance, $R_1$ and $R_2$ can represent an OH or OBn group.

Preferably, $R_1$ and $R_2$ are identical, and represent notably an OH or OBn group.

In particular, R represents a $CH_2OR_8$ group and $R_1$ and $R_2$ represent, independently from one another, an $OR_{15}$ group, $R_8$ and $R_{15}$ representing advantageously a hydrogen atom or an O-protecting group (for example Bn). $R_8$ and the two $R_{15}$ groups can be identical, such as H or an O-protecting group (for example Bn).

According to another particular embodiment, R=$CH_2OH$ and $R_1$=$R_2$=OH or R=$CH_2OBn$ and $R_1$=$R_2$=OBn.

According to a first embodiment, $R_3$ represent an $OSiR^{a3}R^{b3}R^{c3}$, $OR_{22}$, $OC(O)R_{23}$, $OCO_2R_{24}$, $OCONR_{25}R_{26}$, $NR_{29}R_{30}$, $NR_{31}C(O)R_{32}$, $NR_{33}C(O)OR_{34}$, $N(C(O)R_{35})C(O)R_{36}$, $N(C(O)R_{37})C(O)OR_{38}$ or $N(C(O)OR_{39})C(O)OR_{40}$ group, advantageously an $OSiR^{a3}R^{b3}R^{c3}$, $OR_{22}$, $OC(O)R_{23}$, $NR_{29}R_{30}$, $NR_{31}C(O)R_{32}$ or $NR_{33}C(O)OR_{34}$ group, more advantageously an $OR_{22}$, $OC(O)R_{23}$ or $NR_{31}C(O)R_{32}$ group, and even more advantageously an $OR_{22}$ or $NR_{31}C(O)R_{32}$ group.

$R_3$ can represent in particular an $OR_{22}$ group with $R_{22}$ representing a hydrogen atom, a O-protecting group or a $(C_1\text{-}C_6)$-alkyl, aryl or aryl-$(C_1\text{-}C_6)$-alkyl group; an $OC(O)R_{23}$ group with $R_{23}$ representing a $(C_1\text{-}C_6)$-alkyl, aryl or aryl-$(C_1\text{-}C_6)$-alkyl group; or a $NR_{31}C(O)R_{32}$ group with $R_{31}$ representing a hydrogen atom or a $(C_1\text{-}C_6)$-alkyl, aryl or aryl-$(C_1\text{-}C_6)$-alkyl group and $R_{32}$ representing a $(C_1\text{-}C_6)$ alkyl, aryl or aryl-$(C_1\text{-}C_6)$alkyl group.

$R_3$ can represent more particularly an $OR_{22}$ group with $R_{22}$ representing a hydrogen atom or a O-protecting group (for example Bn); or a $NR_{31}C(O)R_{32}$ group with $R_{31}$ representing a hydrogen atom and $R_{32}$ representing a $(C_1\text{-}C_6)$ alkyl. For instance, $R_3$ can represent an OH, OBn, OMOM or NHAc group, in particular OH or OBn.

According to a second embodiment $R_3$ can represent an $OSiR^{a3}R^{b3}R_{c3}$, $OR_{22}$, $OC(O)R_{23}$, $OCO_2R_{24}$ or $OCONR_{25}R_{26}$ group, advantageously an $OSiR^{a3}R^{b3}R^{c3}$, $OR_{22}$ or $OC(O)R_{23}$ group, more advantageously an $OR_{22}$ or $OC(O)R_{23}$ group, and even more advantageously an $OR_{22}$ group.

$R_3$ can represent in particular an $OR_{22}$ group with $R_{22}$ representing a hydrogen atom, a O-protecting group or a $(C_1\text{-}C_6)$-alkyl, aryl or aryl-$(C_1\text{-}C_6)$-alkyl group; or an $OC(O)R_{23}$ group $R_{23}$ with representing a $(C_1\text{-}C_6)$-alkyl, aryl or aryl-$(C_1\text{-}C_6)$-alkyl group.

$R_3$ can represent more particularly an $OR_{22}$ group with $R_{22}$ representing a hydrogen atom or a O-protecting group (for example Bn). For instance, $R_3$ can represent an OH or OBn group.

According to a particular embodiment, $R_1$, $R_2$ and $R_3$ are identical.

According to another particular embodiment, R represents a $CH_2OR_8$ group; $R_1$ and $R_2$ represent, independently from one another, an $OR_{15}$ group; and $R_3$ represents an $OR_{22}$ group, $R_8$, $R_{15}$ and $R_{22}$ representing advantageously a hydrogen atom or an O-protecting group (for example Bn). $R_8$ and the two $R_{15}$ groups can be identical, such as H or an O-protecting group (for example Bn). $R_8$, the two $R_{15}$ and $R_{22}$ groups can also be identical, such as H or an O-protecting group (for example Bn).

According to another particular embodiment, $R=CH_2OH$, $R_1=R_2=OH$ or $R_1=R_2=R_3=OH$.

$R_4$ can advantageously represent a hydrogen or halogen atom or an $OR_{41}$ group; in particular a hydrogen atom or an $OR_{41}$ group; and more particularly an $OR_{41}$ group.

Yet even more advantageously, $R_4$ may represent a hydrogen or halogen atom or an OH, O-protecting, —O—$(C_1\text{-}C_6)$-alkyl, —O-aryl and —O—$(C_1\text{-}C_6)$-alkyl-aryl group; in particular, a hydrogen atom or an OH, O-protecting, —O—$(C_1\text{-}C_6)$-alkyl, —O-aryl and —O—$(C_1\text{-}C_6)$-alkyl-aryl group; and more particularly an OH, O-protecting, —O—$(C_1\text{-}C_6)$-alkyl, —O-aryl and —O—$(C_1\text{-}C_6)$-alkyl-aryl group.

$R_4$ can also represent a hydrogen or halogen atom or an OH, —O—$(C_1\text{-}C_6)$-alkyl, —O-aryl and —O—$(C_1\text{-}C_6)$-alkyl-aryl group; in particular, a hydrogen atom or an OH, —O—$(C_1\text{-}C_6)$-alkyl, —O-aryl and —O—$(C_1\text{-}C_6)$-alkyl-aryl group; and more particularly an OH, —O—$(C_1\text{-}C_6)$-alkyl, —O-aryl and —O—$(C_1\text{-}C_6)$-alkyl-aryl group.

In particular, $R_4$ can represent a hydrogen or halogen (such as Br, Cl, F) atom or an OH or O-protecting group (for ex. OMe or OBn); advantageously a hydrogen atom or an OH or O-protecting group (for ex. OMe or OBn); in particular an OH or O-protecting group such as OH, OMe or OBn.

According to a particular embodiment, $R_0=H$, Et or Bn, $R=CH_2OH$ or $CH_2OBn$ and $R_1=R_2=R_3=OH$ or OBn.

According to another particular embodiment, $R_0=H$ or Bn, $R=CH_2OH$ or $CH_2OBn$ and $R_1=R_2=R_3=OH$ or OBn.

According to another particular embodiment, $R_0=H$, $R=CH_2OH$ and $R_1=R_2=R_3=OH$.

According to yet another particular embodiment, $R_0=H$, $R=CH_2OH$, $R_1=R_2=R_3=OH$ and $R_4=H$ or OH, in particular OH.

According to a particular embodiment, the compound of the invention is a compound of formula (I):
or a salt thereof, a solvate, a tautomer, a stereoisomer or a mixture of stereoisomers in any proportion, in particular a mixture of enantiomers, and particularly a racemate mixture, in which:

m represents 0 or 1, p represents 0 or 1, notably 1, $R_0$ represents a hydrogen atom or a O-protecting group (for example a $(C_1\text{-}C_6)$alkyl or aryl-$(C_1\text{-}C_6)$alkyl group), $R_{5a}$, $R_{6a}$ and $R_{7a}$ represent, independently from each other, a hydrogen or a N-protecting group (for example —$CO_2$—$R_{GP1}$), and $R_5$, $R_6$ and $R_7$ represent, independently from each other, a hydrogen; a $(C_1\text{-}C_6)$alkyl optionally substituted by a $(C_1\text{-}C_6)$alkoxy or a $(C_1\text{-}C_6)$thioalkoxy; an aryl; an aryl-$(C_1\text{-}C_6)$alkyl optionally substituted by a $(C_1\text{-}C_6)$alkoxy; or a group of the following formula:

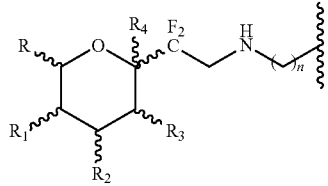

or $R_5$ and $R_{5a}$ and/or R % and $R_{6a}$ and/or $R_7$ and $R_{7a}$ form, with the nitrogen and carbon atoms carrying them, a pyrrolidine cycle

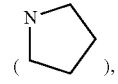

provided that at least one and only one group among $R_5$, R % and $R_7$ when m=p=1, or at least one and only one group among $R_5$ and R % when m=0 and p=1, or at least one and only one group among $R_5$ and $R_7$ when m=1 and p=0, or $R_5$ when m=p=0 represents a group of formula:

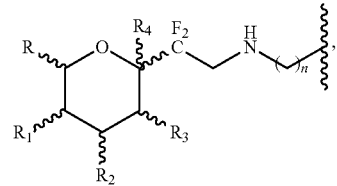

with
n representing an integer from 1 to 6,

R representing $CH_2OR_8$, $R_1$ and $R_2$ representing, independently from one another, $OR_{15}$, $R_3$ representing $OR_{22}$, $R_4$ representing H or $OR_{41}$, in particular $OR_{41}$, or R and $R_1$, together with the carbon atoms carrying them, form a cyclic acetal having the following formula:

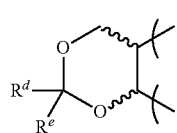

and/or ($R_1$ and $R_2$), ($R_2$ and $R_3$), and/or ($R_3$ and $R_4$), together with the carbon atoms carrying them, form a cyclic acetal having the following formula:

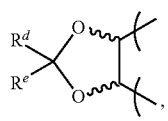

$R_8$, $R_{15}$ and $R_{22}$ representing, independently from one another, a hydrogen atom or a O-protecting group (for example a ($C_1$-$C_6$)alkyl or aryl-($C_1$-$C_6$)alkyl group), $R_{41}$ representing a hydrogen atom, a O-protecting group (for example a ($C_1$-$C_6$)alkyl or aryl-($C_1$-$C_6$)alkyl group) or a ($C_1$-$C_6$)alkyl, aryl, aryl-($C_1$-$C_6$)alkyl, or ($C_1$-$C_6$)-alkyl-aryl group, this group being possibly unsubstituted or substituted with one or more groups chosen among a halogen atom and ($C_1$-$C_6$)alkoxy, and $R^d$ and $R^e$ representing, independently from one another, a hydrogen atom or a ($C_1$-$C_6$)alkyl group.

According to a particular embodiment, the compounds of the present invention have one of the following formulas (Ib), (Ic), (Id1), (Id2), (Ie1) and (Ie2), notably of the following formulas (Ib), (Ic), (Id2) and (Ie2):

(Ib)
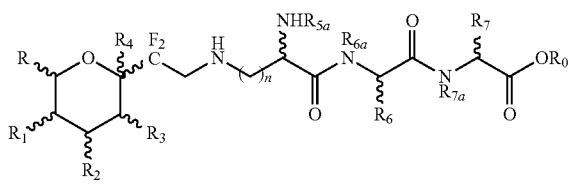

(Ic)
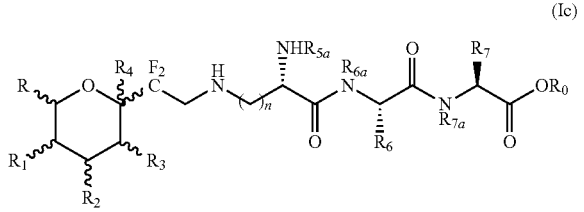

(Id1)
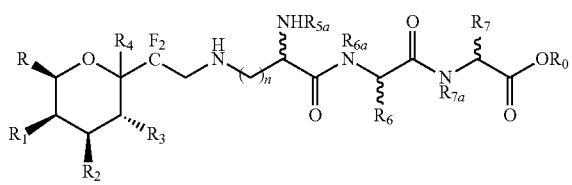

(Id2)
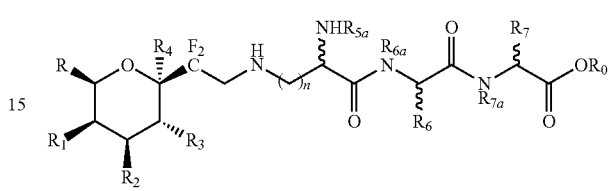

(Ie1)
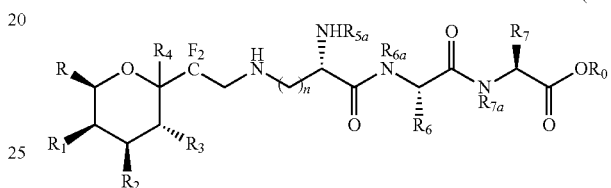

(Ie2)
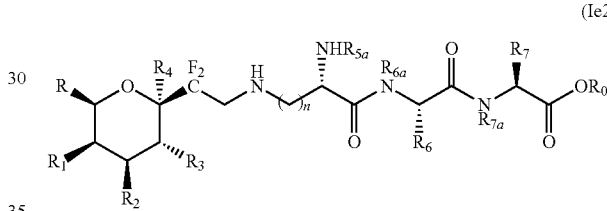

in which n, $R_0$, R, $R_1$, $R_2$, $R_3$, $R_4$, $R_{5a}$, $R_6$, $R_{6a}$, $R_7$ and $R_{7a}$ are as defined above.

According to another particular embodiment, the compounds of the present invention have one of the following formulas (If), (Ig), (Ih1), (Ih2), (Ii1), and (Ii2), notably of the following formulas (If), (Ig), (Ih2) and (Ii2):

(If)
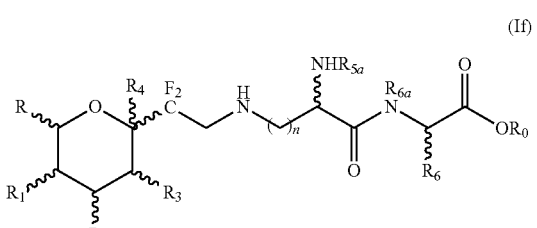

(Ig)
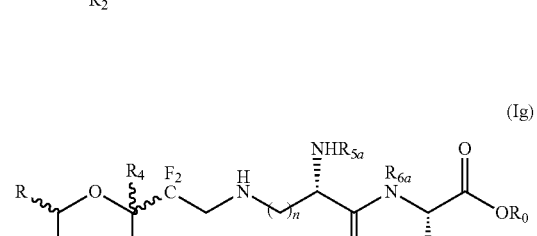

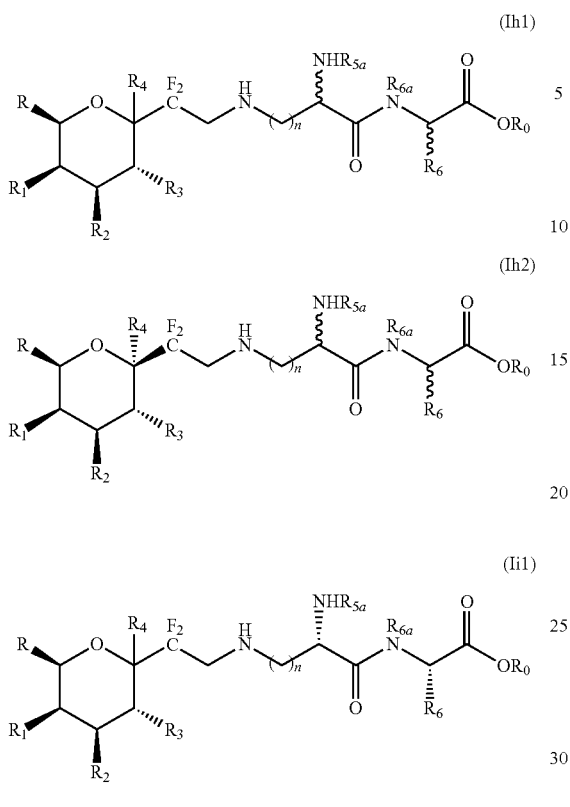
(Ih1)
(Ih2)
(Ii1)
(Ii2)
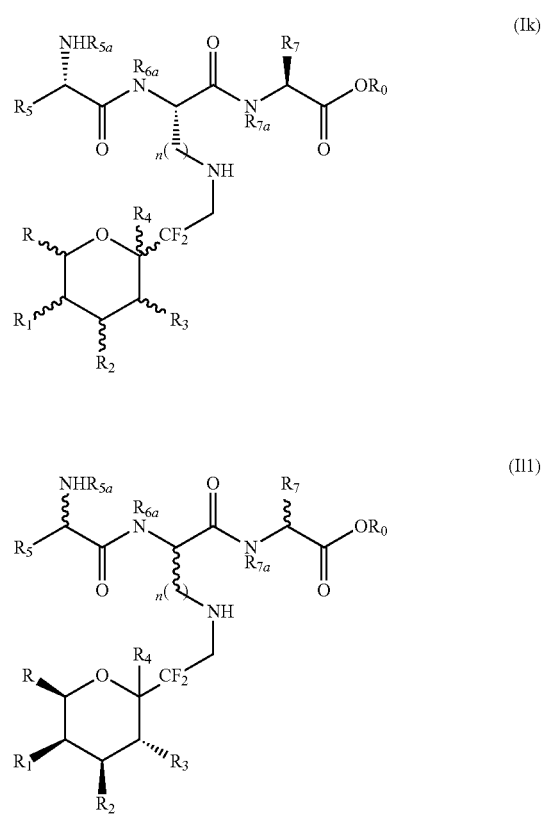
(Ik)
(Il1)
(Il2)
in which n, $R_0$, R, $R_1$, $R_2$, $R_3$, $R_4$, $R_{5a}$, $R_6$ and $R_{6a}$ are as defined above.
According to yet another particular embodiment, the compounds of the present invention have one of the following formulas (Ij), (Ik), (Il1), (Il2), (Im1) and (Im2), notably of the following formulas (Ij), (Ik), (Il2) and (Im2):
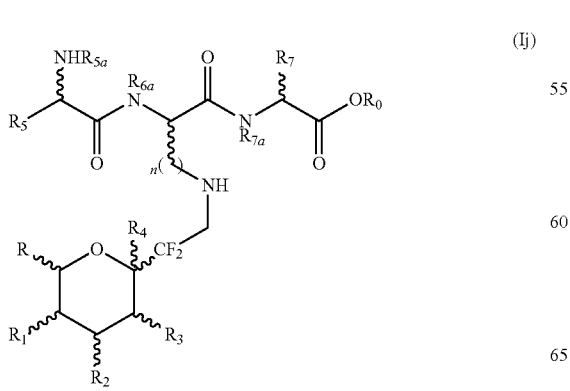
(Ij)
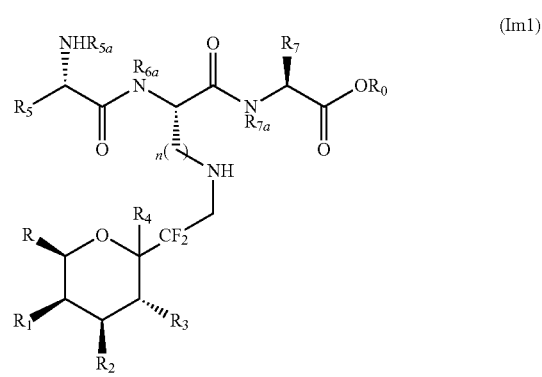
(Im1)

-continued

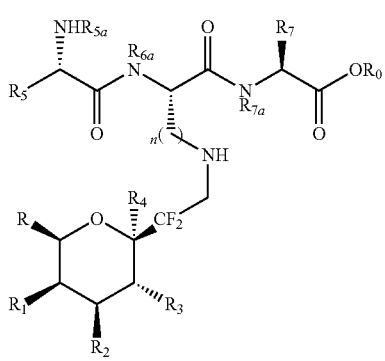
(Im2)

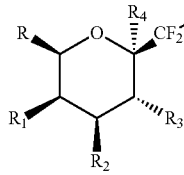

in which n, $R_0$, R, $R_1$, $R_2$, $R_3$, $R_4$, $R_{5a}$, $R_6$, $R_{6a}$, $R_7$ and $R_{7a}$ are as defined above.

According to still another particular embodiment, the compounds of the present invention have one of the following formulas (In), (Io), (Ip1), (Ip2), (Iq1) and (Iq2), notably of the following formulas (In), (Io), (Ip2) and (Iq2):

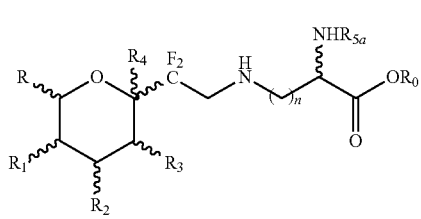
(In)

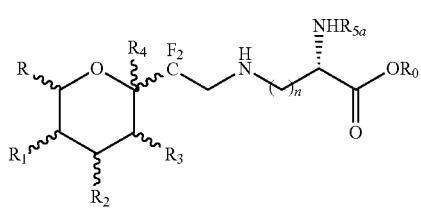
(Io)

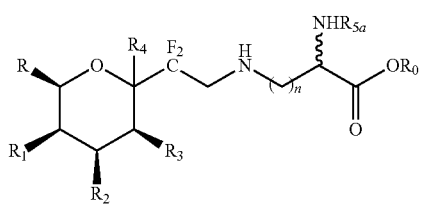
(Ip1)

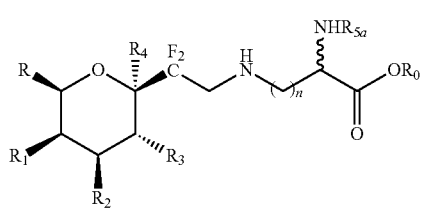
(Ip2)

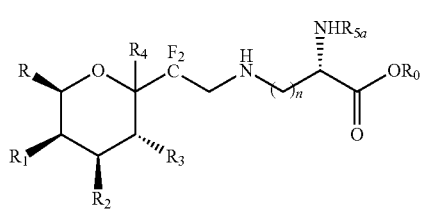
(Iq1)

(Iq2)

in which n, $R_0$, R, $R_1$, $R_2$, $R_3$, $R_4$ and $R_{5a}$ are as defined above.

Advantageously, the compounds of the present invention is a compound of formula (Ib), (If), (Ij) or (In), notably of formula (Ib), (If) or (Ij), in particular of formula (Ib).

Preferably, the compounds of the present invention is a compound of formula (Ie1), (Ii1), (Im1) or (Iq1), notably of formula (Ie1), (Ii1) or (Im1), in particular of formula (Ie1).

In particular, the compounds of the present invention is a compound of formula (Ie2), (Ii2), (Im2) or (Iq2), notably of formula (Ie2), (Ii2) or (Im2), in particular of formula (Ie2).

The compound of formula (I) can be chosen among the following compounds:

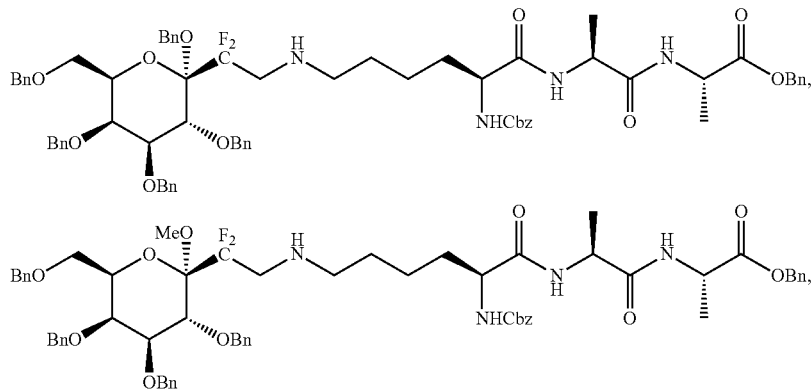

-continued
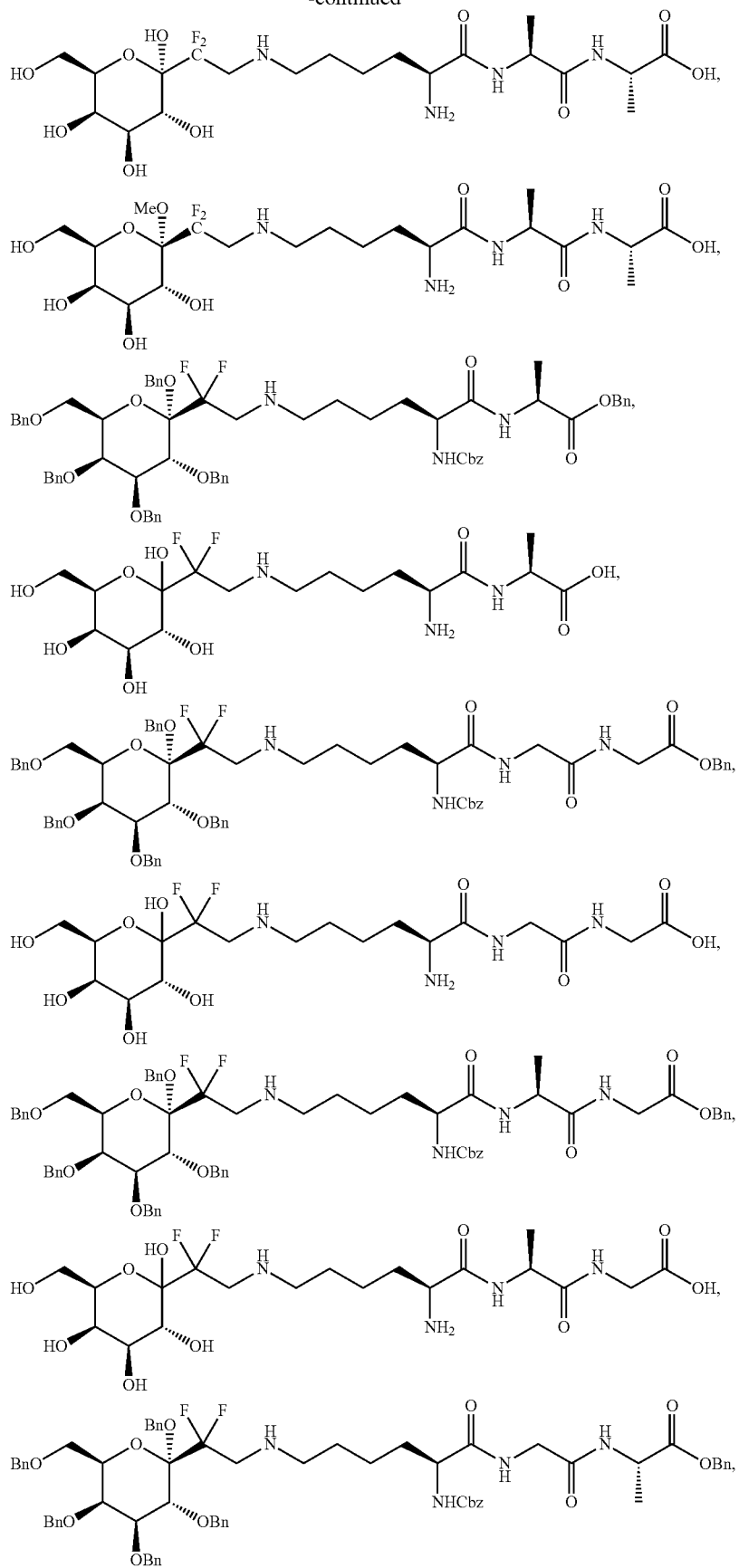

-continued
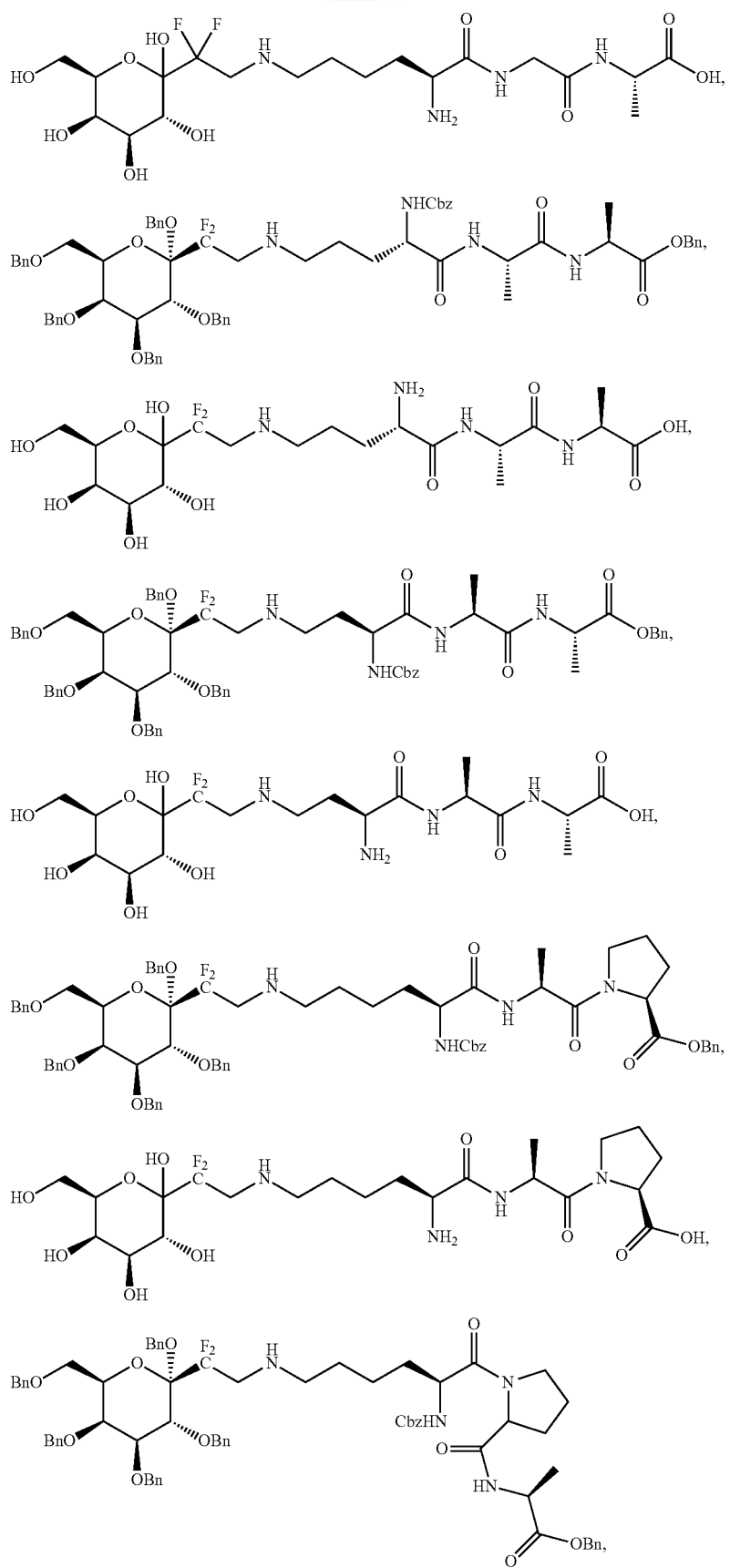

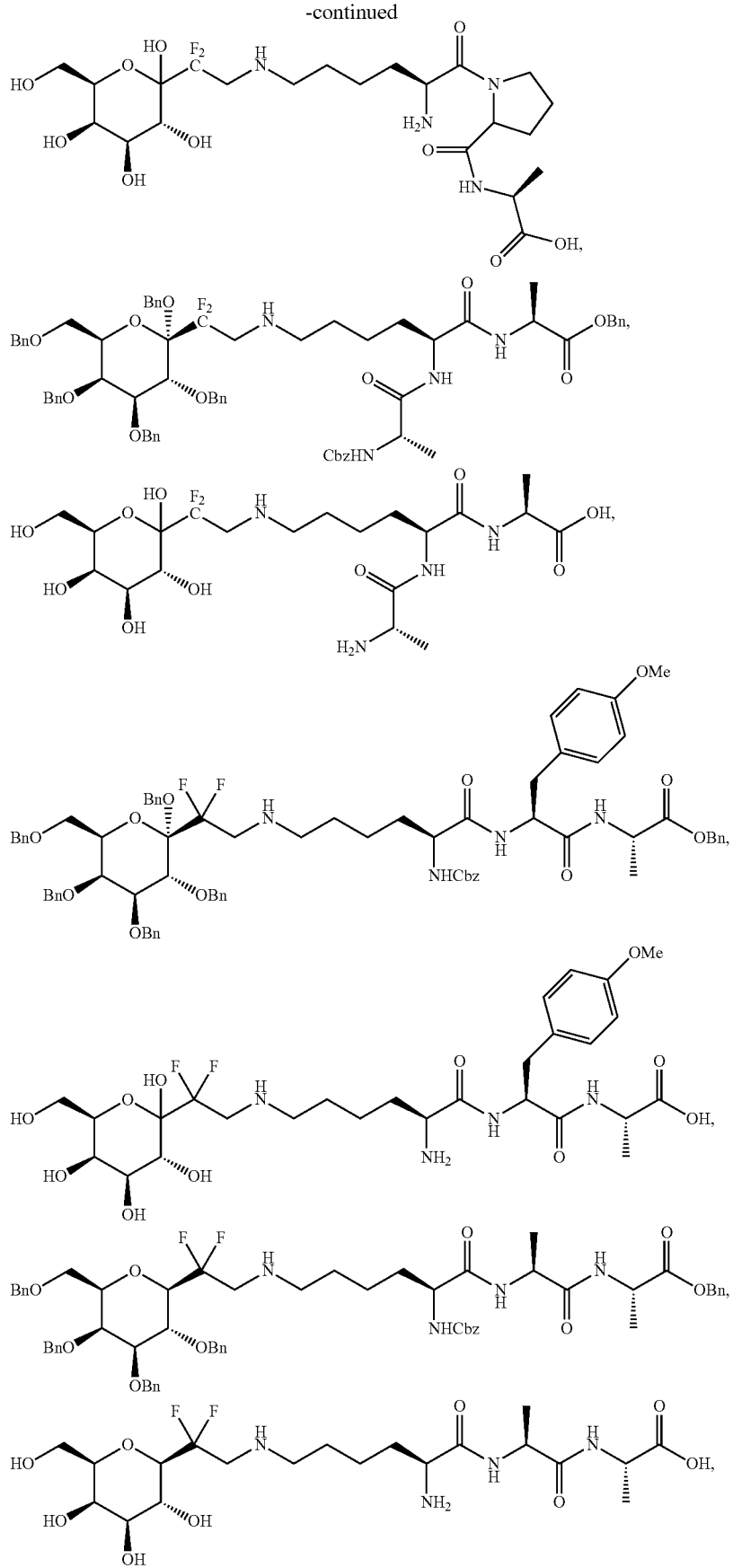

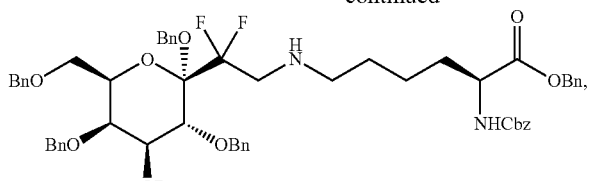
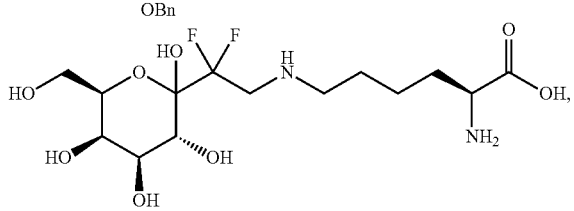
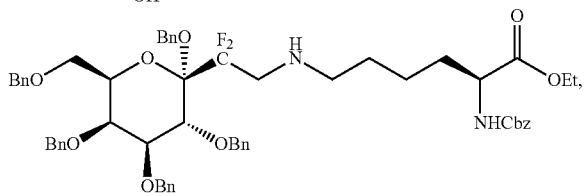
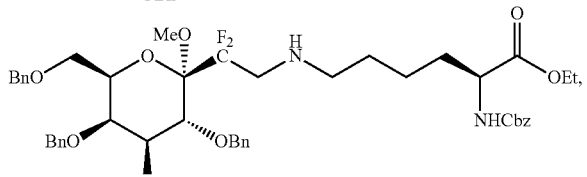
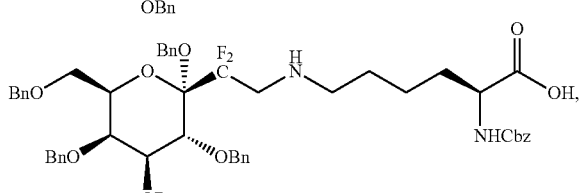
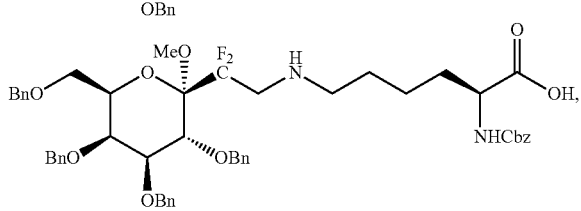
and the salts and solvates thereof (notably acid addition salts in particular with hydrochloric acid or acetic acid, more particularly with hydrochloric acid).
In particular, the compound of formula (I) can be chosen among the following compounds:
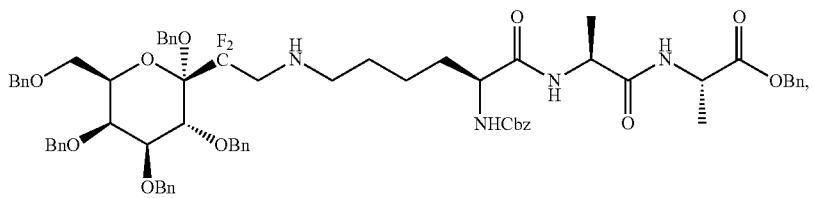

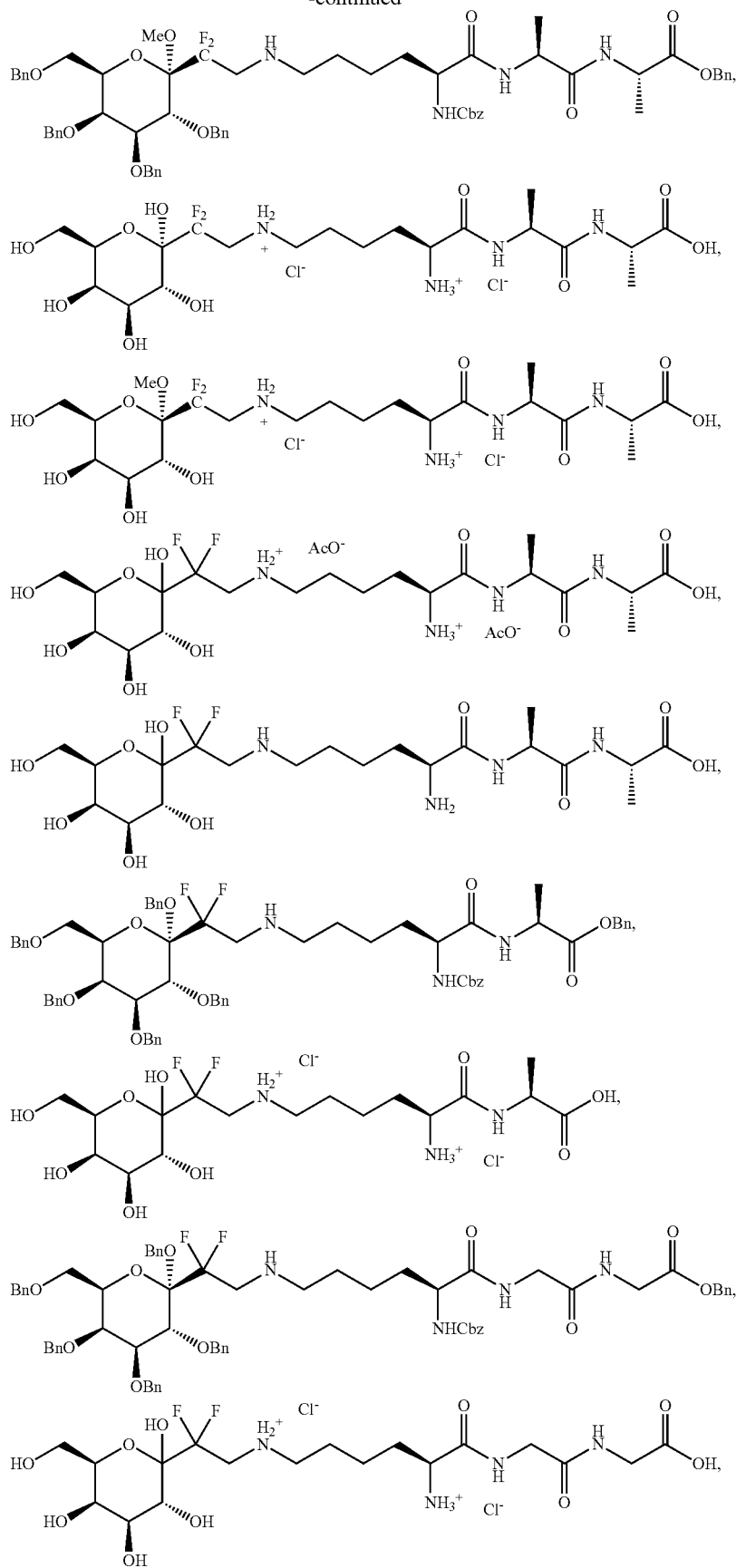

-continued
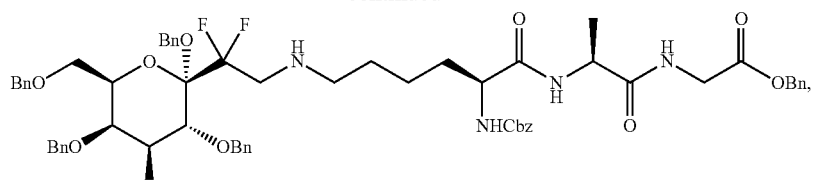
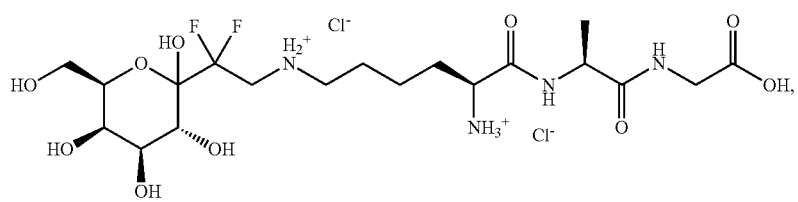
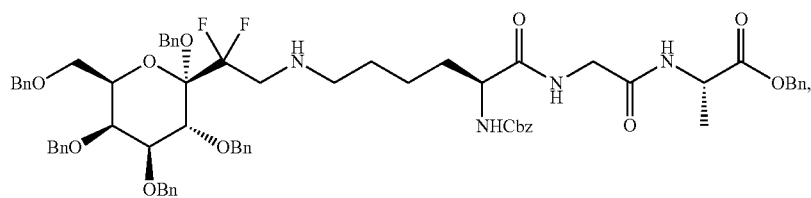
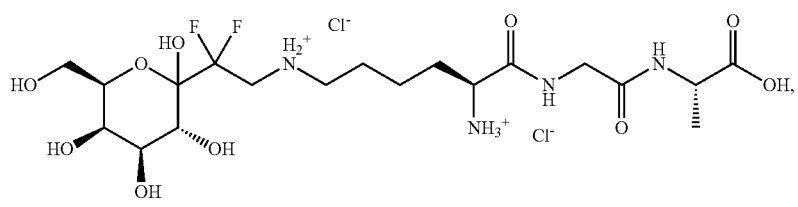
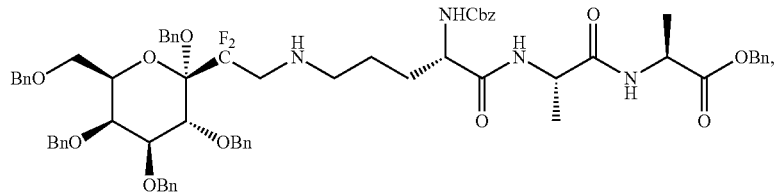
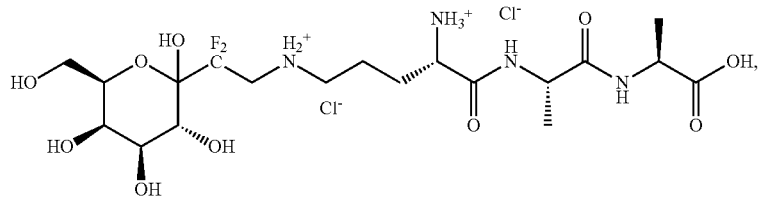
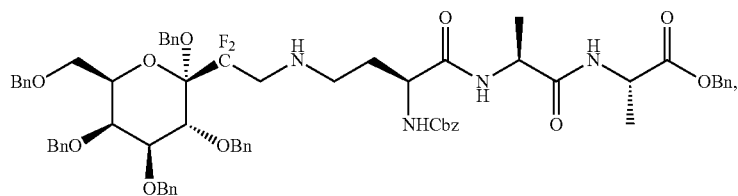
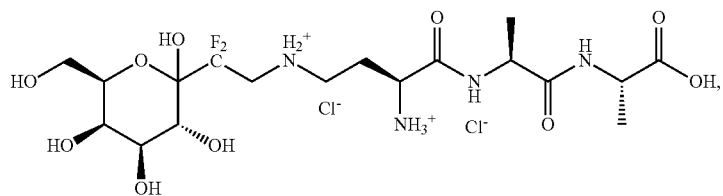

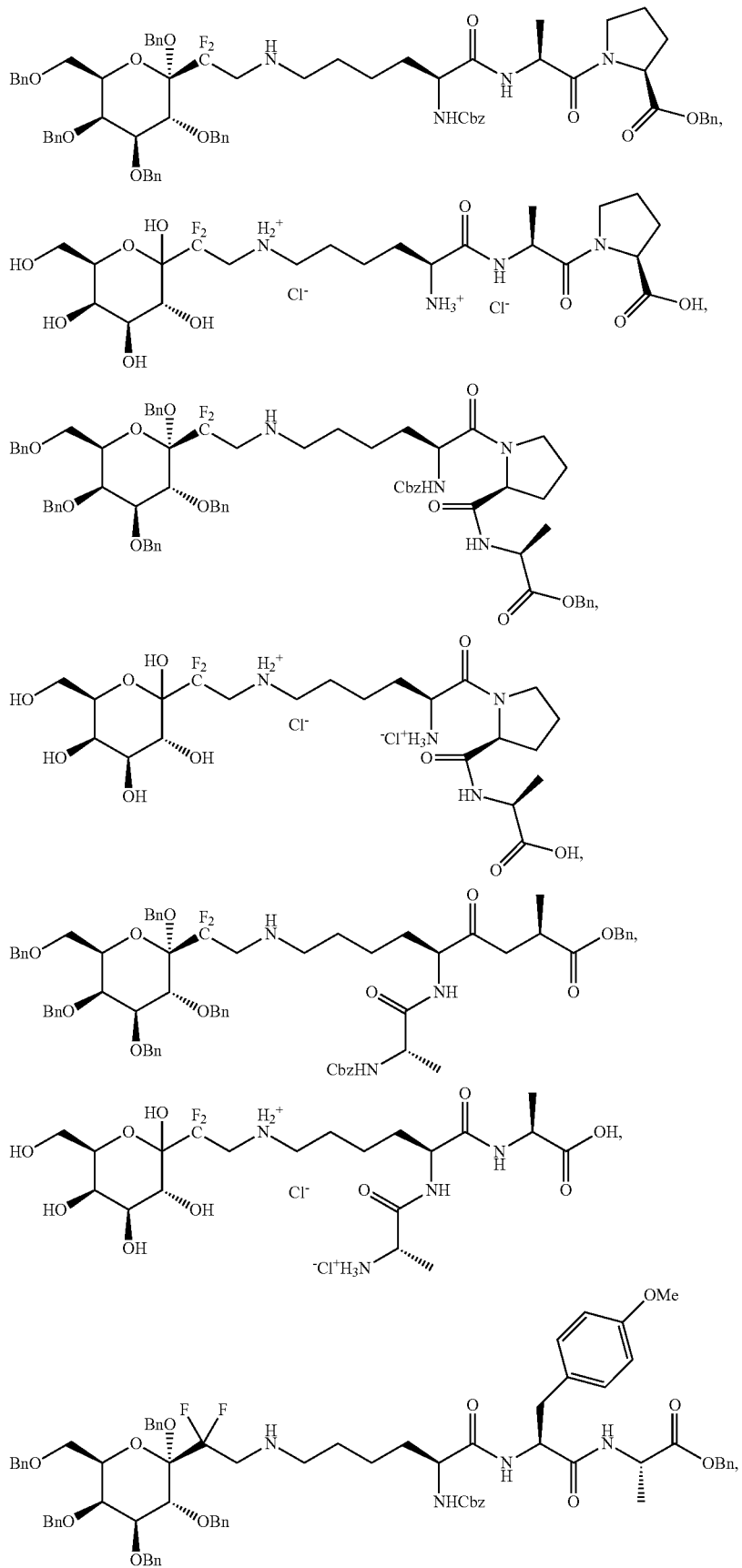

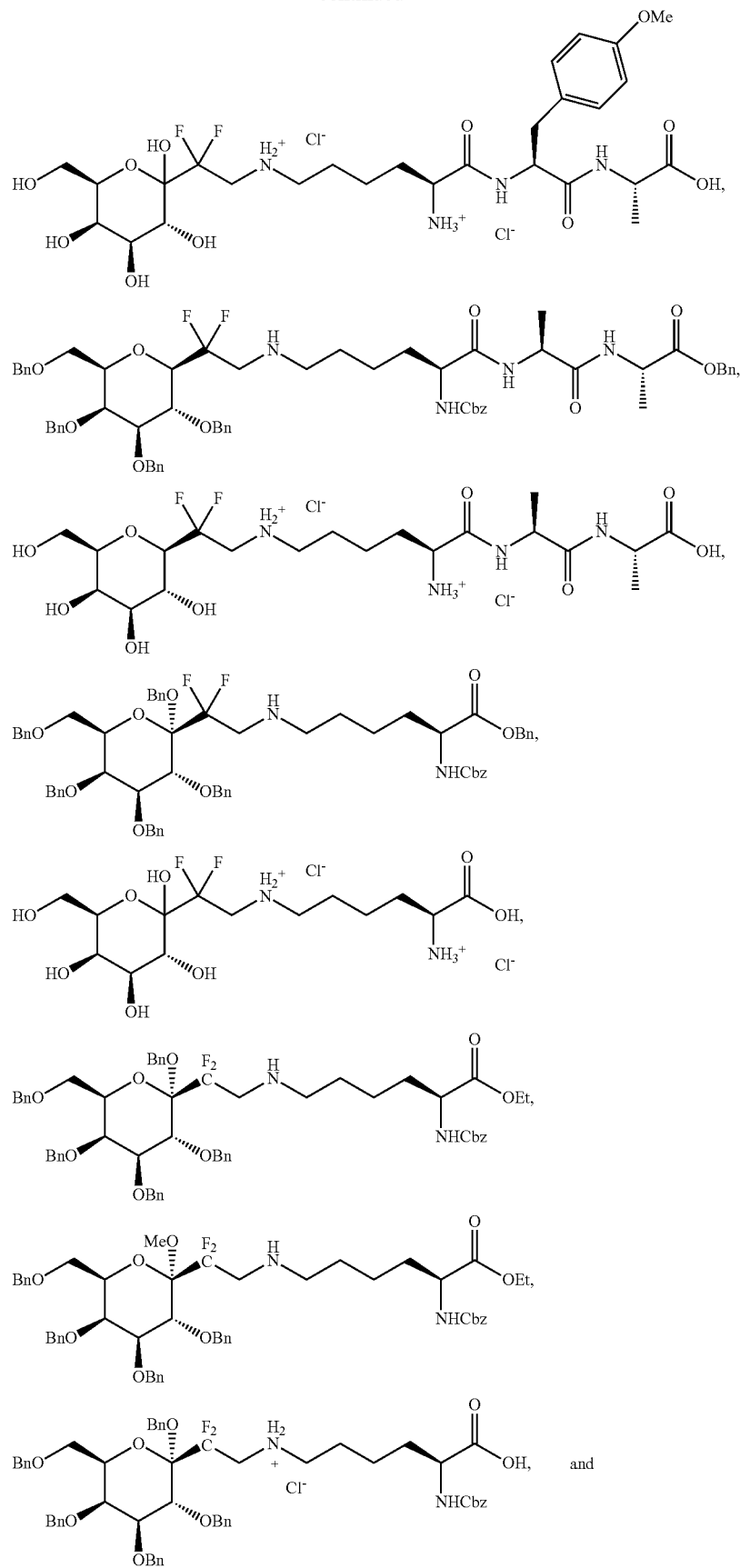

-continued

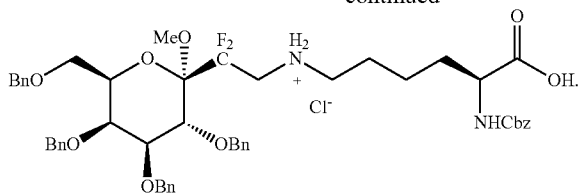

The present invention relates also to the use of a compound of formula (I) as defined above for the preservation and/or protection and/or regeneration of biological materials and of microorganisms.

The present invention relates also to a method of preservation and/or protection of biological materials and of microorganisms by placing said biological materials in a medium containing a compound of formula (I) as defined above.

The term "preservation" of a biological material or of a microorganism as used in the present invention refers to the fact to maintain the state (notably the structure and function) of the biological material or microorganism as it already exists or to prevent or limit the degradation of this state.

The term "protection" of a biological material or of a microorganism as used in the present invention refers to the fact that the biological material or microorganism is protected against an internal or external aggression, such as a stress, for ex. an oxidative stress (for ex. UV), a change of temperature, a change of pH, a chemical or bacterial contamination, starvation conditions, etc.

The term "regeneration" of a biological material or of a microorganism as used in the present invention refers to the fact to recover the state (notably the structure and function) of the biological material or microorganism as it existed before an internal or external aggression, such as a stress, for ex. an oxidative stress (for ex. UV), a change of temperature, a change of pH, a chemical or bacterial contamination, starvation conditions, etc. It concerns more particularly a biological material, such as cells.

In particular, a biological material or a microorganism can be protected/preserved when placed at a temperature below 37° C., such as below 0° C., notably in conditions of cryopreservation in particular for biological materials such as human organs, tissues (e.g. for transplant), body fluids or cells.

The cryopreservation of a biological material or a microorganism implies to cool to sub-zero temperatures the biological material or microorganism, and notably at a temperature of about −196° C. by using liquid nitrogen.

The biological material can be in particular cells, tissues, body fluids or organs.

The microorganism can be in particular a prokaryotic or eukaryotic microorganism, being notably unicellular or pluricellular.

The microorganism can be notably chosen among bacteria, fungi, including yeasts, algae, viruses, including phages, microparasites (also called parasitic microorganisms) and protozoa.

The present invention relates also to the use of a compound of formula (I) as defined above as an adjuvant in a culture, storage and/or preservation medium.

The culture, storage and/or preservation medium is intended for the culture, storage and/or preservation of a biological material or of a microorganism. The biological material will be more particularly cells or tissues in the case of a culture medium.

The present invention relates also to a culture, storage and/or preservation medium comprising at least one compound of formula (I) as defined above.

The culture, storage and/or preservation medium can be liquid or in the form of a gel. It contains thus water. However, the medium can be in a dehydrated form which can be rehydrated by water addition.

It can contain one or several components of the group consisting of co-solvents (e.g. dimethylsulfoxyde (DMSO)), salts (for ex. NaCl, $MgCl_2$, $ZnCl_2$, $MnCl_2$, $CuCl_2$, $K_2PO_4$, $KH_2PO_4$, $K_2HPO_4$, $Na_2S_2O_3$, $K_2SO_4$, $MgSO_4$, $KNO_3$, $Ca(NO_3)_2$, $Na_2CO_3$, $NaHCO_3$, etc.), carbon sources such as carbohydrates (for ex. glucose, lactose or sucrose) or polyols (for ex mannitol or glycerol), vitamins (for ex. vitamins B1, B2, B6, B12, B3, B5, B9, B7, C, A, D, E and K), nitrogen and amino acid sources (for ex. peptones, beef or yeast extract, serum, etc.), growth factors (for ex. insulin, transferrin, fibonectin, albumin), differentiating factors, antibiotics and antimycotics (also called antibacterial and antifungal agents—e.g. actinomycin D, amphotericin B, ampicillin, carbenicillin, cefotaxime, fosmidomycin, gentamicin, kanamycin, neomycin, streptomycin, penicillin, polymixin B), hormones, cytokines and trace elements.

Other additives can be present such as indicators (of pH for example), inhibitors, etc.

When it is in the form of a gel, the culture medium can further comprise a gelling agent such as agar, gelatine, silica gel, etc.

Preferably, in the case of such an application, $R_0$=H, R=$CH_2OH$ and $R_1$=$R_2$=$R_3$=OH. Advantageously, $R_{5a}$, $R_{6a}$ and $R_{7a}$ represent, independently from one another, a hydrogen or $R_5$ and $R_{5a}$ and/or $R_6$ and $R_{6a}$ and/or $R_7$ and $R_{7a}$ form, with the nitrogen and carbon atoms carrying them, a pyrrolidine cycle

The present invention relates also to a cosmetic use of a compound of formula (I) for anti-aging and skin protection, or also for skin regeneration.

The present invention relates also to a cosmetic method for anti-aging and skin protection, or also for skin regeneration, by applying a compound of formula (I) as defined above to the skin.

The present invention relates also to a method for anti-aging and skin protection, or also for skin regeneration, by applying to the skin of a person in need thereof of an affective amount of a compound of formula (I) as defined above.

In such use or method, the compound of formula (I) can be applied topically on the skin.

The present invention relates also to a cosmetic or dermatological composition comprising at least one compound of formula (I) as defined above and at least one cosmetically or dermatologically acceptable excipient.

Preferably, in the case of such a cosmetic application, $R_0$=H, R=CH$_2$OH and $R_1$=$R_2$=$R_3$=OH. Advantageously, $R_{5a}$, $R_{6a}$ and $R_{7a}$ represent, independently from one another, a hydrogen or $R_5$ and $R_{5a}$ and/or $R_6$ and $R_{6a}$ and/or $R_7$ and $R_{7a}$ form, with the nitrogen and carbon atoms carrying them, a pyrrolidine cycle

The cosmetic or dermatological composition of the invention can also comprise one or more additive(s), such as antimicrobial agents (for dermatological composition), antioxidants, dermatologically active agents (for dermatological composition), emollients, humectants, thickening agents, fragrances, preservatives, pigments or colorants or opacifiers. Such additives are conventional to those of skill in the art.

Examples of these additives are listed below as well as in the International Cosmetic Ingredient Dictionary and Handbook, eds. Wenninger and McEwen (The Cosmetic, Toiletry, and Fragrance Assoc., Washington, D.C., 7@th Edition, 1997) (hereinafter "ICT Handbook").

Antimicrobial agents can be used when the composition is to be applied to skin prone to microbial infection, e.g., by bacteria, fungal, or protozoa. Examples of such agents include benzyl alcohol, chlorobutanol, phenylethyl alcohol, phenylmercuric acetate, potassium sorbate, sorbic acid, benzoic acid, phenoxyethanol, butylparaben, ethylparaben, methylparaben, propylparaben, and sodium benzoate, and in particular methylparaben. Other antimicrobial agents are listed on page 1612 of the ICT handbook.

Antioxidants can be used to protect ingredients of the composition from oxidizing agents that are included within or come in contact with the composition. Examples of antioxidants include ascorbyl palmitate, butylated hydroxyanisole, butylated hydroxytoluene, potassium propyl gallate, octyl gallate, dodecyl gallate, phenyl-α-napthyl-amine, and tocopherols such as α-tocopherol. Other antioxidants are listed on pages 1612-13 of the ICT Handbook.

Dermatologically active agents include agents for treating wound healing, inflammation, acne, psoriasis, impetigo, herpes, dermatitis, pain, itching or skin irritation. Examples of such dermatologically active agents include hydrocortisone, dexamethesone, panthenol, phenol, tetracycline hydrochloride, yeast, hexylresorcinol, lamin, kinetin, betamethasone, triamcinolone, fluocinolone, methylpredniso lone, retinoids such as retinol and retinoic acid, dapsone, sulfasalazine, resorcinol, salicylic acid, benzoyl peroxide, erythromycin-benzoyl peroxide, erythromycin, clindamycin, mupirocin, griseofulvin, azoles such as miconazole, econozole, itraconazole, fluconazole, and ketoconazole, ciclopirox, allylamines such as naftifine and terfinafine, acyclovir, famciclovir, valacyclovir, benzocaine, lidocaine, dibucaine, pramoxine hydrochloride, methyl salicylate, camphor, menthol, resocinol, and vitamins such as tocopherol, and tocopherol acetate.

Emollients are agents that soften and smooth the skin. Examples of emollients include oils and waxes such as microcrystaline wax, polyethylene, triglyceride esters such as those of castor oil, cocoa butter, safflower oil, corn oil, olive oil, cod liver oil, almond oil, palm oil, squalene, and soybean oil, acetylated monoglycerides, ethoxylated glycerides, fatty acids, alkyl esters of fatty acids, alkenyl esters of fatty acids, fatty alcohols, fatty alcohol ethers, etheresters, lanolin and derivatives of lanolin, polyhydric alcohol esters, wax esters such as beeswax, vegetable waxes, phospholids, and sterols, isopropyl palmitate or glyceryl stearate, and in particular almond oil or fatty alcohols such as cetyl, stearyl and/or myristyl alcohols. Other emollients are listed on pages 1656-61 of the ICT handbook.

Siloxanes are particularly preferred emollient. Siloxanes that may be used in the present invention include, but are not limited to, dimethicone, cyclomethicone, phenyl trimethicone, phenyl dimethicone, cetyl dimethicone, stearyl dimethicone, amodimethicone, $C_{30-45}$ alkyl dimethicone, $C_{30-45}$ Alkyl Methicone, Cetearyl methicone, dimethicone copolyol, cyclopentasiloxane, cyclohexasiloxane or any combinations thereof. In particular, amodimethicone could be used as emollient in the present invention.

Thickening agents could be in particular fatty alcohols such as cetyl, stearyl and/or myristyl alcohols.

Examples of fragrances or perfume include peppermint, rose oil, rose water, aloe vera, clove oil, menthol, camphor, eucalyptus oil, and other plant extracts. To eliminate certain odours from compositions, masking agents may be used. Other fragrances and masking agents are listed on pages 1639-40 of the ICT Handbook.

Preservatives can be used to protect the composition from degradation. Examples of preservatives include phenoxyethanol, butylparaben, ethylparaben, methylparaben, propyl paraben, benzalkonium chloride, benzethonium chloride, benzoic acid, benzyl alcohol, and mixtures thereof such as liquipar oil. In particular, it can be phenoxyethanol, methylparaben or a mixture thereof. Other preservatives are listed on pages 1654-55 of the ICT Handbook. However, the composition of the present invention can be preservative free.

Pigments or colorants are used to modify the color of the composition, such as to obtain a white composition. It can be in particular titanium dioxide.

Opacifiers, such as titanium oxide, are used in clear or transparent composition in order to render it opaque.

The cosmetic or dermatological composition according to the invention can be formulated in particular for a topical administration. It can thus be a lotion, a foam, a gel, a dispersion, a suspension, a spray, a serum, a cream, an emulsion, a body milk, a shampoo, or also a mask.

The cosmetic or dermatological composition is intended in particular for anti-aging and skin protection, or also for skin regeneration.

The inventors of the present invention have thus developed processes to prepare the compounds according to the invention. The present invention relates thus also to processes for preparing a compound of formula (I) as defined above.

A first process for preparing a compound of formula (I) as defined above comprises the following successive steps:

(a) reducing the imine function of a compound of the following formula (II):

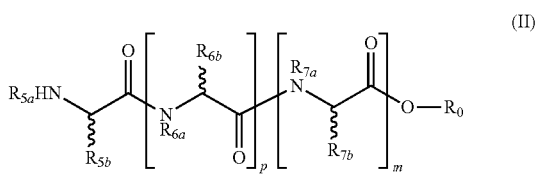
(II)

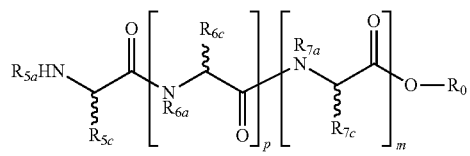
(III)

in which:
m, p, $R_0$, $R_{5a}$, $R_{6a}$ and $R_{7a}$ are as defined above, and
$R_{5b}$, $R_{6b}$ and $R_{7b}$ represent, independently from each other, a hydrogen; a ($C_1$-$C_6$)alkyl optionally substituted by a ($C_1$-$C_6$)alkoxy or a ($C_1$-$C_6$)thioalkoxy; an aryl; an aryl-($C_1$-$C_6$)alkyl optionally substituted by a ($C_1$-$C_6$)alkoxy; or a group of the following formula:

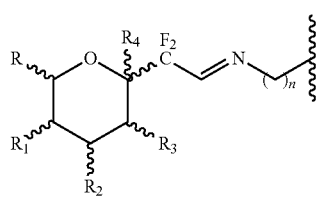

with n, R, $R_1$, $R_2$, $R_3$ and $R_4$ as defined above,
or $R_{5b}$ and $R_{5a}$ and/or $R_{6b}$ and $R_{6a}$ and/or $R_{7b}$ and $R_{7a}$ form, with the nitrogen and carbon atoms carrying them, a pyrrolidine cycle

provided that at least one and only one group among $R_{5b}$, $R_{6b}$ and $R_{7b}$ when m=p=1, or at least one and only one group among $R_{5b}$ and $R_{6b}$ when m=0 and p=1, or at least one and only one group among $R_{5b}$ and $R_{7b}$ when m=1 and p=0, or $R_{5b}$ when m=p=0, represents a group of formula:

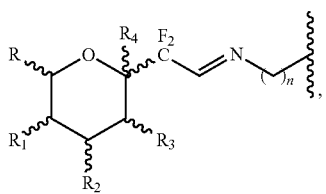

to obtain a compound of formula (I), and
(b) optionally salifying or solvating the compound obtained in previous step (a) to obtain a salt or solvate of a compound of formula (I). A deprotection step can be carried out after, before and or during this step.
Step (a):
The reduction reaction can be carried out in the presence of a borohydride such as $NaBH_3CN$ or $NaBH(OAc)_3$.
The compound of formula (II) can be prepared by reacting a compound of the following formula (III):

or a salt thereof (notably an acid addition salt for example with trifluoroacetic or hydrochloric acid),
in which:
m, p, $R_0$, $R_{5a}$, $R_{6a}$ and $R_{7a}$ are as defined above, and
$R_5$, $R_{6c}$ and $R_7$ represent, independently from each other, a hydrogen; a ($C_1$-$C_6$)alkyl optionally substituted by a ($C_1$-$C_6$)alkoxy or a ($C_1$-$C_6$)thioalkoxy; an aryl; an aryl-($C_1$-$C_6$)alkyl optionally substituted by a ($C_1$-$C_6$)alkoxy; or a group of the following formula:

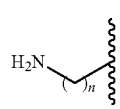

with n as defined above,
or $R_{5c}$ and $R_{5a}$ and/or $R_6$, and $R_{6a}$ and/or $R_{7c}$ and $R_{7a}$ form, with the nitrogen and carbon atoms carrying them, a pyrrolidine cycle

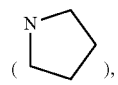

provided that at least one and only one group among $R_{5c}$, $R_{6c}$ and $R_{7c}$ when m=p=1, or at least one and only one group among $R_{5c}$ and $R_{6c}$ when m=0 and p=1, or at least one and only one group among $R_{5c}$ and $R_{7c}$ when m=1 and p=0, or $R_{5c}$ when m=p=0, represents a group of formula:

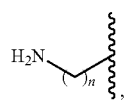

with a compound of the following formula (IV):

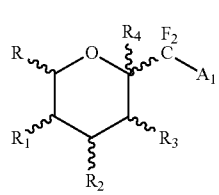
(IV)

in which R, $R_1$, $R_2$, $R_3$ and $R_4$ are as defined above and $A_1$ represents CHO or $C(OA_2)(OA_3)$ with $A_2$ and $A_3$ representing, independently of one another, H, ($C_1$-$C_6$)alkyl or aryl-($C_1$-$C_6$)alkyl; notably with $A_2$=H and $A_3$ representing ($C_1$-$C_6$)alkyl or aryl-($C_1$-$C_6$)alky, notably ($C_1$-$C_6$)alkyl.
This reaction can be carried out in toluene at the reflux temperature in the presence of a Dean-Stark apparatus.

This reaction can also be carried out in the presence of a base, such as triethylamine, and a dessicant agent, such as MgSO$_4$. In this case dichloromethane can be used as solvent.

In the case of this reaction, advantageously R$_0$≠H, R$_{5a}$≠H, R≠CH$_2$OH, R$_1$≠H, R$_2$≠H, R$_3$≠H, and R$_4$≠OH. Thus, to prepare compounds which such substituents, the OH or NH functions should be preferably protected by a protecting group as defined above before performing the reaction between the compounds of formulas (III) and (IV). A deprotection step can be carried out after this step, notably at the last step of the process.

The compound of formula (IV) can be prepared notably by reduction of a compound of the following formula (V):

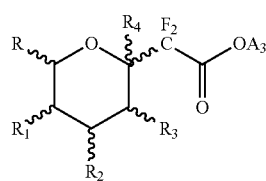

(V)

in which A$_3$, R, R$_1$, R$_2$, R$_3$ and R$_4$ are as defined above.

Such a reduction reaction can be carried out in conditions well-known to the person skilled in the art, notably in the presence of a reducing agent such as DIBAl-H.

The compound of formula (V) can be prepared by methods well known to the person skilled in the art or described in the literature.

In the case of this reaction, advantageously R≠CH$_2$OH, R$_1$≠H, R$_2$≠H, R$_3$≠H, and R$_4$≠OH. Thus, to prepare compounds which such substituents, the OH functions should be preferably protected by a O-protecting group as defined above before performing the reaction between the compounds of formulas (III) and (IV). A deprotection step can be carried out after this step, notably at the last step of the process.

Step (b):

The salification or solvatation step can be carried out by methods well known to the one skilled in the art, in particular by reaction of the compound of formula (I) obtained in step (a) with an organic or inorganic acid, an organic or inorganic base or a solvent, as defined previously.

The solvent can be notably the solvent used in the last step of the preparation of the compound according to the invention, in particular the solvent used in step (a).

Thus steps (a) and (b) can be carried out in a single step, without isolating intermediate compounds.

A deprotection step can be carried out after, before and or during this step.

A second process for preparing a compound of formula (I) as defined above comprises the following successive steps:
(i) reacting a compound of the following formula (IX):

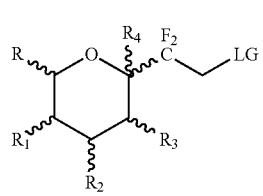

(IX)

in which R, R$_1$, R$_2$, R$_3$ and R$_4$ are as defined above and LG represents a leaving group,
with a compound of formula (III) as defined above or a salt thereof (notably an acid addition salt for example with trifluoroacetic acid),
to obtain a compound of formula (I), and
(ii) optionally salifying or solvating the compound obtained in previous step (i) to obtain a salt or solvate of a compound of formula (I).

Step (i):

The term "leaving group" as used in the present invention refers to a chemical group which can be easily replaced with a nucleophile during a nucleophile substitution reaction, the nucleophile being in the present case an amine, i.e. a molecule carrying a group NH$_2$ (optionally in the form of a salt). Such a leaving group can be in particular a halogen atom or a sulfonate. The sulfonate is in particular a group —OSO$_2$—R$_{48}$ with R$_{48}$ representing a (C$_1$-C$_6$)alkyl, aryl, aryl-(C$_1$-C$_6$)alkyl or (C$_1$-C$_6$)alkyl-aryl group, the said group being optionally substituted with one or several halogen atoms such as fluorine atoms. The sulfonate can be notably a mesylate (CH$_3$—S(O$_2$)O—), a triflate (CF$_3$—S(O)$_2$O—) or a tosylate (p-Me-C$_6$H$_4$—S(O)$_2$O—).

The leaving group LG will be notably a sulfonate such as a triflate.

The substitution reaction of step (i) is advantageously carried out in the presence of a base such as K$_2$CO$_3$. The reaction can be carried out in a solvent such as DMF.

In the case of the reaction of step (i), advantageously R$_0$≠H, R$_{5a}$≠H, R≠CH$_2$OH, R$_1$≠H, R$_2$≠H, R$_3$≠H, and R$_4$≠OH. Thus, to prepare compounds which such substituents, the OH or NH functions should be preferably protected by a protecting group as defined above before performing the reaction between the compounds of formulas (III) and (IX). A deprotection step can be carried out after this step, notably at the last step of the process.

The compound of formula (IX) can be prepared by transformation into a leaving group of the hydroxyl function (OH) of a compound of the following formula (X):

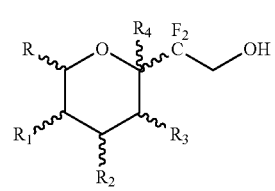

(X)

in which R, R$_1$, R$_2$, R$_3$ and R$_4$ are as defined above.

The reaction of transformation of the OH function into a leaving group is well known to the person skilled in the art. In the case where LG=OTf, the reaction can be carried out in the presence of Tf$_2$O and a base such as pyridine. The reaction can be carried out in a solvent such as dichloromethane.

In the case of this reaction, advantageously R≠CH$_2$OH, R$_1$≠H, R$_2$≠H, R$_3$≠H, and R$_4$≠OH. Thus, to prepare compounds which such substituents, the OH functions should be preferably protected by a O-protecting group as defined above before performing this reaction. A deprotection step can be carried out after this step, notably at the last step of the process.

The compound of formula (X) can be prepared from compound of formula (V) by a reduction step using a standard reducing agent such as NaBH$_4$, for example in a solvent such as THF, MeOH or a mixture THF/MeOH.

Step (ii):

The salification or solvatation step can be carried out by methods well known to the one skilled in the art, in particular by reaction of the compound of formula (I) obtained in step (i) with an organic or inorganic acid, an organic or inorganic base or a solvent, as defined previously.

The solvent can be notably the solvent used in the last step of the preparation of the compound according to the invention, in particular the solvent used in step (i).

Thus steps (i) and (ii) can be carried out in a single step, without isolating intermediate compounds.

A deprotection step can be carried out after, before or during this step.

A third process for preparing a compound of formula (I) as defined above where m and p are not both 0 and $R_5$ represents a group of the following formula:

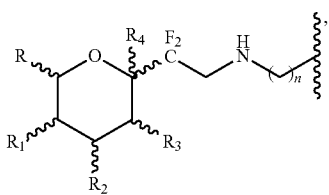

comprises the following successive steps:

(1) reacting a compound of the following formula (XIa):

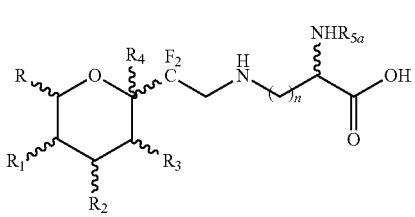

(XIa)

or a salt thereof (notably an acid addition salt for example with hydrochloric acid), in which n, R, $R_1$, $R_2$, $R_3$, $R_4$ and $R_{5a}$ are as defined above, with a compound of the following formula (VII):

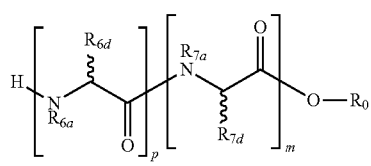

(VII)

or a salt thereof (notably an acid addition salt for example with trifluoroacetic or hydrochloric acid), in which m, p, $R_0$, $R_{6a}$ and $R_{7a}$ are as defined above (m and p are not both 0) and $R_{6d}$ and $R_{7d}$ represent, independently of each other, a hydrogen; a ($C_1$-$C_6$) alkyl optionally substituted by a ($C_1$-$C_6$)alkoxy or a ($C_1$-$C_6$)thioalkoxy; an aryl; or an aryl-($C_1$-$C_6$)alkyl optionally substituted by a ($C_1$-$C_6$)alkoxy; or $R_{6d}$ and $R_{6a}$ and/or $R_{7d}$ and $R_{7a}$ form, with the nitrogen and carbon atoms carrying them, a pyrrolidine cycle

to obtain a compound of formula (I), and (2) optionally salifying or solvating the compound obtained in previous step (1) to obtain a salt or solvate of a compound of formula (I).

Step (1):

The reaction of step (1) can be carried out in conventional conditions used for peptide coupling, these conditions being well known to the person skilled in the art.

The peptide coupling can be carried out in the presence of a coupling agent, such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), hexafluorophosphate 2-(1H-benzotriazole-1-yl)-1,1,3,3-tetraméthyluronium (HBTU), tetrafluoroborate 2-(1H-benzotriazole-1-yl)-1,1,3,3-tetramethyluronium (TBTU), hexafluorophosphate O-(7-azobenzotriazol-1-yl)-1,1,3,3-tetramethyluronium (HATU) or (benzotriazol-1-yloxy)tripyrrolodinophosphonium hexafluorophosphate (PyBOP); optionally associated with an additive or a base, such as N-hydroxy-succinimide (NHS), N-hydroxy-benzotriazole (HOBt), 3,4-dihydro-3-hydroxy-4-oxo-1,2,3-benzotriazole (HOOBt), 1-hydroxy-7-azabenzotriazole (HAt), N-hydroxy sylfosuccinimide (sulfo NHS), dimethylaminopyridine (DMAP) or N-methyl morpholine (NMM). In the present case, the reaction can be carried out in the presence of PyBOP and NMM.

Advantageously, this reaction is carried out with a compound of formula (VII) in which $R_{6a}$=H if p=1 or $R_{7a}$=H if p=0. Thus an additional step of substitution of the amine function can be performed to obtain a compound of formula (I) with $R_{6a} \neq H$ if p=1 or $R_{7a} \neq H$ if p=0. Such a substitution step can be carried out by methods well-known to the one skilled in the art.

In the case of this reaction, advantageously $R_0 \neq H$, $R_{5a} \neq H$, $R \neq CH_2OH$, $R_1 \neq H$, $R_2 \neq H$, $R_3 \neq H$, and $R_4 \neq OH$. Thus, to prepare compounds which such substituents, the OH or NH functions should be preferably protected by a protecting group as defined above before performing the reaction between the compounds of formulas (III) and (IV). A deprotection step can be carried out after this step, notably at the last step of the process.

The compound of formula (XIa) can be prepared by reduction of the imine function of a compound of the following formula (VI):

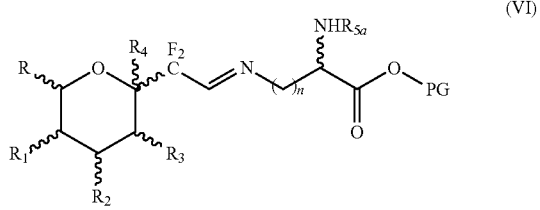

(VI)

in which n, PG, R, $R_1$, $R_2$, $R_3$, $R_4$ and $R_{5a}$ are as defined above and PG represents a O-protecting group such as a ($C_1$-$C_6$)alkyl group (for example ethyl), to give a compound of the following formula (XIb):

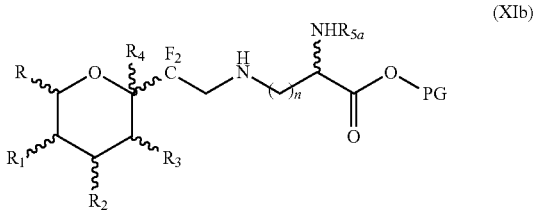
(XIb)

in which n, PG, R, $R_1$, $R_2$, $R_3$, $R_4$ and $R_{5a}$ are as defined above,
followed by a deprotection step of the carboxylic acid function bearing the PG group.

The reduction reaction can be carried out in the presence of a borohydride such as $NaBH_3CN$ or $NaBH(OAc)_3$.

In the case of this reaction, advantageously $R_0 \neq H$, $R_{5a} \neq H$, $R \neq CH_2OH$, $R_1 \neq H$, $R_2 \neq H$, $R_3 \neq H$, and $R_4 \neq OH$. Thus, to prepare compounds which such substituents, the OH or NH functions should be preferably protected by a protecting group as defined above before performing the reaction between the compounds of formulas (III) and (IV). A deprotection step can be carried out after this step, notably at the last step of the process.

The compound of formula (XIb) can also be prepared by reacting a compound of the following formula (VIII):

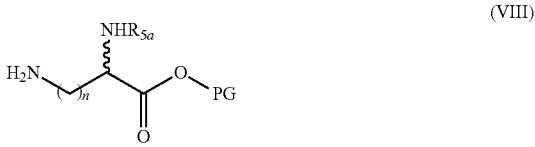
(VIII)

in which n and $R_{5a}$ are as defined above and PG represents a O-protecting group such as a $(C_1\text{-}C_6)$alkyl group (for example ethyl),
with a compound of formula (IX).

This reaction can be carried out in the presence of a base such as $K_2CO_3$. The reaction can be carried out in a solvent such as DMF.

In the case of this reaction, advantageously $R_0 \neq H$, $R_{5a} \neq H$, $R \neq CH_2OH$, $R_1 \neq H$, $R_2 \neq H$, $R_3 \neq H$, and $R_4 \neq OH$. Thus, to prepare compounds which such substituents, the OH or NH functions should be preferably protected by a protecting group as defined above before performing the reaction between the compounds of formulas (III) and (IX). A deprotection step can be carried out after this step, notably at the last step of the process.

Step (2):

The salification or solvatation step can be carried out by methods well known to the one skilled in the art, in particular by reaction of the compound of formula (I) obtained in step (1) with an organic or inorganic acid, an organic or inorganic base or a solvent, as defined previously.

The solvent can be notably the solvent used in the last step of the preparation of the compound according to the invention, in particular the solvent used in step (1).

Thus steps (1) and (2) can be carried out in a single step, without isolating intermediate compounds.

A deprotection step can be carried out after, before and or during this step.

Further protection/deprotection steps can be carried out in the processes described above, such steps and their reaction conditions being well known to the one skilled in the art.

The compound obtained by any of the preceding processes can be separated from the reaction medium by methods well known to the person skilled in the art, such as by extraction, evaporation of the solvent or by precipitation or crystallisation (followed by filtration).

The compound can be also purified if necessary by methods well known to the person skilled in the art, such as by recrystallization, by distillation, by chromatography on a column of silica gel or by high performance liquid chromatography (HPLC).

The present invention relates also to:
a compound of the following formula (II):

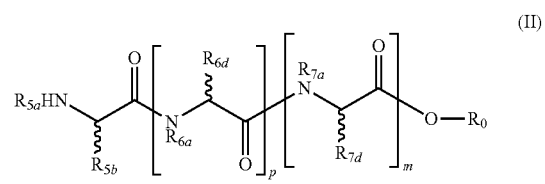
(II)

in which m, p, $R_0$, $R_{5a}$, $R_{5b}$, $R_{6a}$, $R_{6b}$, $R_{7a}$ and $R_{7b}$ are as defined above but m and p are not both 0,
a compound of the following formula (VI):

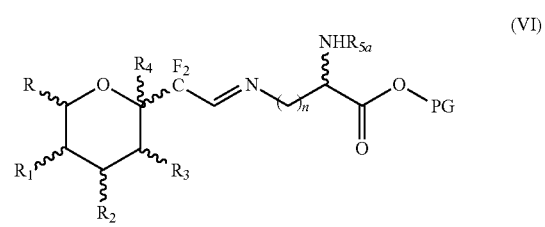
(VI)

in which n, R, $R_1$, $R_2$, $R_3$, $R_4$, $R_{5a}$ and PG are as defined above,
a compound of the following formula (XI):

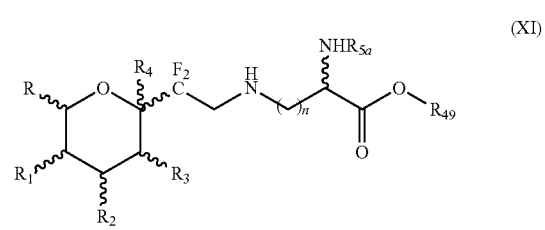
(XI)

in which n, R, $R_1$, $R_2$, $R_3$, $R_4$ and $R_{5a}$ are as defined above and $R_{49}$ represents H or a O-protecting group such as a $(C_1\text{-}C_6)$alkyl group,
or a salt thereof, a solvate, a tautomer, a stereoisomer or a mixture of stereoisomers in any proportion, in particular a mixture of enantiomers, and particularly a racemate mixture.

These compounds of formula (II), (VI) or (XI) are useful as synthesis intermediate in the preparation of compounds of formula (I).

The examples which follow illustrate the invention without limiting its scope in any way.

FIGURES

FIG. 1 represents the percentage of fibroblasts viability during time (from 0 to 12 days) after incubation in a common culture medium (surviving control), in a starvation medium (serum-free control) and in a starvation medium containing compound 17 at 5 mg/mL.

FIGS. 2 and 3 represent respectively the $^1$H RMN spectrum of a solution of compound 17 after addition of 0 or 8 equivalents of NaOD and 2 h 30 of reaction.

EXAMPLES

Figure 1:
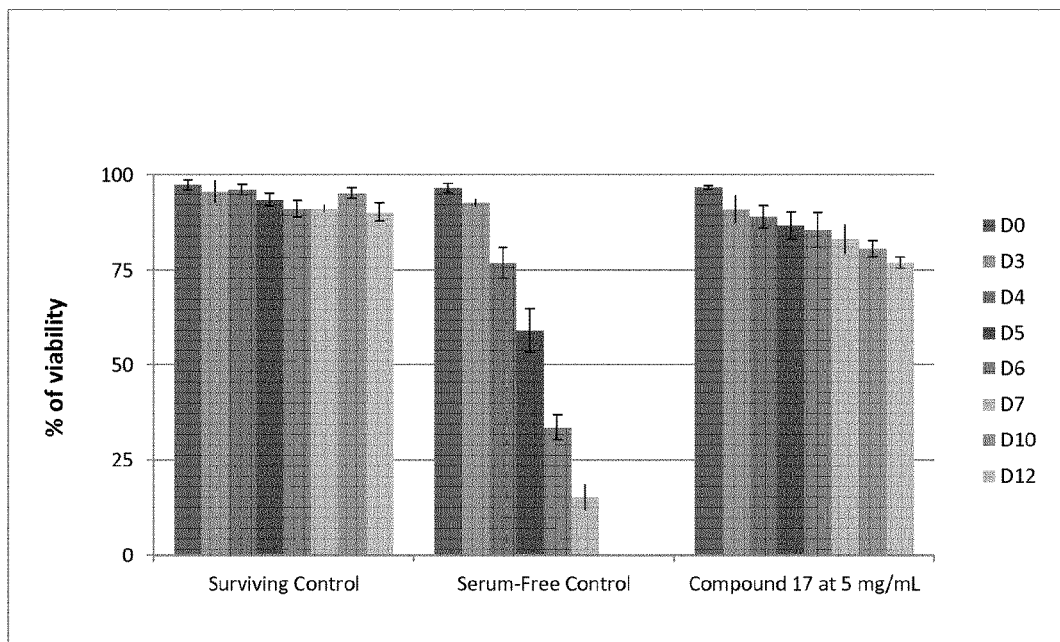

The following abbreviations have been used:
Ala: Alanine
Ac: Acetyl (COCH$_3$)
Bn: Benzyl (CH$_2$Ph)
Cbz: Benzyloxycarbonyl (CO$_2$CH$_2$Ph)
CDI: Carbonyldiimidazole
Dab: 2,4-Diaminobutyric acid
DCE: Dichloroethane
DMEM: Dulbecco's Modified Eagle Medium
DMF: Dimethylformamide
DIBAl-H: Diisobutylaluminium hydride
DIEA: N,N-Diisopropylethylamine
EDTA: Ethylenediaminetetraacetic acid
ESI: Electrospray ionisation
Et: Ethyl (CH$_2$CH$_3$)
FBS: Fetal Bovine Serum
Gly: Glycine
Lys: Lysine
Me: Methyl (CH$_3$)
MEM: Minimum Essential Media
NMM: N-Methylmorpholine
NMR: Nuclear Magnetic Resonance
OD: Optical density
Orn: Ornithine
PBS: Phosphate buffered saline
Pro: Proline
PSNEt$_2$: Diethylaminomethyl-polystyrene
PyBOP: (1H-Benzotriazol-1-yloxy)tripyrrolidinophosphonium hexafluorophosphate
Tf: Trifluoromethanesulfonyl (SO$_2$CF$_3$)
TFA: Trifluoroacetic acid
THF: Tetrahydrofuran
Tyr: Tyrosine
Z: Benzyloxycarbonyl (CO$_2$CH$_2$Ph)

I—Synthesis of the Compounds According to the Invention

It should be noted that the compounds according to the invention where $R_4=R_1=OH$ can be obtained in the form of a mixture of tautomer forms as explained in the description above. For practical reasons, these compounds are represented by their pyranose form. It concerns compounds 17, 19, 20, 22, 24, 26, 28, 30, 32, 34, 36, 38, 40 and 44 according to the invention.

I-1. General procedure
Synthesis of Peptide Intermediates

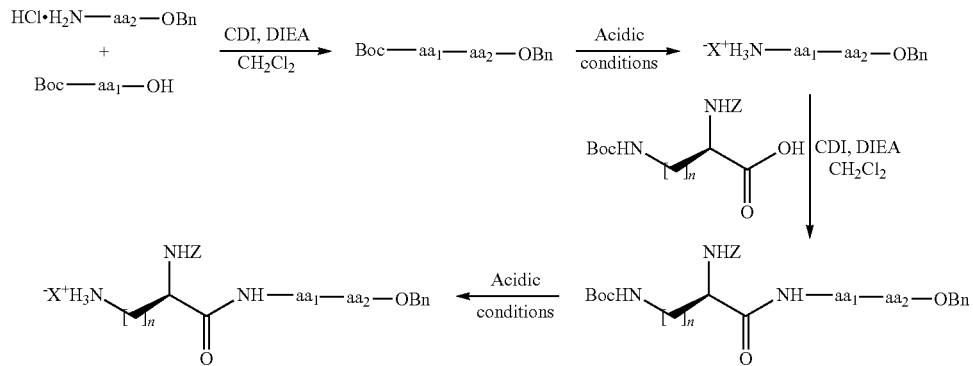

(where aa$_1$ and aa$_2$ each represent independently a residue of amino acid)

Example of Synthesis of Peptide Intermediates

General Procedure A

Boc-aa$_1$-OH and HCl.H$_2$N-aa$_2$-OBn coupling: Boc-aa$_1$-OH was dissolved in dichloromethane and carbonyldiimidazole (1.03 eq.) was added portionwise. After stirring during 1 h, a solution of HCl.H$_2$N-aa$_2$-OBn (1 eq.) and DIEA (2.1 eq.) in dichloromethane was added dropwise. The reaction mixture was stirred at room temperature overnight. Aqueous HCl 1N was added and the mixture was vigorously stirred for 10 min. The layers were separated and the aqueous one was extracted with dichloromethane. The combined organic layers were washed with brine, dried over anhydrous sodium sulfate and concentrated under vacuum. The obtained residue was purified by flash column chromatography to give Boc-aa$_1$-aa$_2$-OBn.

General Procedure B

N-deprotection using TFA: N-Boc peptide was dissolved in dichloromethane and trifluoroacetic acid (20 eq.) was added dropwise. The reaction mixture was stirred at room temperature overnight before being concentrated under vacuum to give ammonium trifluoroacetate salt of the peptide (X$^-$=CF$_3$CO$_2^-$).

General Procedure C

N-deprotection using HCl: N-Boc peptide was dissolved in dichloromethane and a 4M solution of HCl in dioxane (10 eq.) was added dropwise. The reaction mixture was stirred at room temperature for 2 h before being concentrated under vacuum to give ammonium hydrochloride salt of the peptide (X$^-$=Cl$^-$).

General Procedure D

Z,Boc-protected amino acid

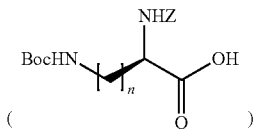

and ⁻X.⁺H₃N-aa₁-aa₂-OBn coupling: Z,Boc-protected amino acid was dissolved in dichloromethane and carbonyldiimidazole (1.2 eq.) was added portionwise. After stirring during 1 h, a solution of ⁻X.⁺H₃N-aa₁-aa₂-OBn (1 eq.) and DIEA (2.1 eq.) in dichloromethane was added dropwise. The reaction mixture was stirred at room temperature overnight. An aqueous solution of 1M HCl was added and the mixture was vigorously stirred for 10 min. The layers were separated and the aqueous one was extracted with dichloromethane. The combined organic layers were washed with brine, dried over anhydrous sodium sulfate and concentrated under vacuum. The obtained residue was purified by flash column chromatography to give the coupling residue.

Boc-Ala-Ala-OBn: Using general procedure A with Boc-Ala-OH (10 g, 52.9 mmol, 1 eq.) and HCl.H₂N-Ala-OBn (11.4 g, 52.9 mmol, 1 eq.). Pale yellow oil (18.2 g, 98%). MS (ESI⁺): 351.2 [M+H]⁺; 373.2 [M+Na]⁺; 389.1 [M+K]⁺

HCl.H₂N-Ala-Ala-OBn: Using general procedure C starting from Boc-Ala-Ala-OBn (18.04 g, 51.5 mmol, 1 eq.). White solid (14.75 g, 100%).

MS (ESI⁺): 251.1 [M-HCl+H]⁺; 273.1 [M-HCl+Na]⁺; 289.1 [M-HCl+K]⁺

TFA.H₂N-Ala-Ala-OBn: Using general procedure B starting from Boc-Ala-Ala-OBn (17.2 g, 49.03 mmol, 1 eq.). Pale yellow oil (17.9 g, 100%).

$^1$H NMR (CDCl₃, 300 MHz): 1.3-1.5 (m, 6H), 4.0-4.2 (m, 1H), 4.3-4.5 (m, 1H), 5.02 (d, 1H, $^1J_{H-H}$=11.5 Hz), 5.11 (d, 1H, $^1J_{H-H}$=11.5 Hz), 7.1-7.4 (m, 5H), 7.65 (d, 1H, $^3J_{H-H}$=6 Hz), 7.8-8.3 (m, 2H)

Z-Lys(Boc)-Ala-Ala-OBn: Using general procedure D starting from HCl.H₂N-ALa-Ala-OBn (15 g, 52.3 mmol, 1 eq.) and Z-Lys(Boc)-OH (19.9 g, 52.5 mmol, 1 eq.). White solid (21.2 g, 67%).

MS (ESI⁺): 613.3 [M+H]⁺; 635.2 [M+Na]⁺; 651.2 [M+K]⁺

Z-Lys(HCl)-Ala-Ala-OBn: Using general procedure C starting from Z-Lys(Boc)-Ala-Ala-OBn (21 g, 34.3 mmol, 1 eq.). White solid (16.4 g, 87%).

MS (ESI⁺): 513.2 [M-HCl+H]⁺; 535.2 [M-HCl+Na]⁺; 551.2 [M-HCl+K]⁺

Z-Lys(Boc)-Ala-OBn: Using general procedure D with Z-Lys(Boc)-OH (2 g, 5.26 mmol, 1 eq.) and HCl.H₂N-Ala-OBn (1.13 g, 5.26 mmol, 1 eq.) instead of HCl.H₂N-aa₁-aa₂-OBn. Pale yellow solid (1.89 g, 66%).

$^1$H NMR_(CDCl₃, 300 MHz): 1.3 (m, 16H); 1.6-1.7 (m, 2H); 3.0 (m, 2H); 4.1 (m, 1H); 4.5 (m, 1H); 4.6 (m, 1H); 5.0 (s, 2H); 5.1 (m, 1H); 5.5 (d, 7 Hz, 1H); 6.8 (d, 6.5 Hz, 1H); 7.3 (m, 10H).

Z-Lys(HCl)-Ala-OBn: Using general procedure C starting from Z-Lys(Boc)-Ala-OBn (756 mg, 1.40 mmol, 1 eq.). White solid (778 mg, 100%).

MS (ESI⁺): 223.1 [M+H]⁺; 245.1 [M+Na]⁺; 261.1 [M+K]⁺

Boc-Gly-Gly-OBn: Using general procedure A with Boc-Gly-OH (800 mg, 4.57 mmol, 1 eq.) and HCl.H₂N-Gly-OBn (922 mg, 4.57 mmol, 1 eq.). Colorless oil (1.40 g, 95%).

MS (ESI⁺): 323.2 [M+H]⁺; 345.1 [M+Na]⁺; 361.1 [M+K]⁺

HCl.H₂N-Gly-Gly-OBn: Using general procedure C starting from Boc-Gly-Gly-OBn (1.37 g, 4.25 mmol, 1 eq.). White solid (1.14 g, 100%).

MS (ESI⁺): 223.1[M-HCl+H]⁺; 245.1 [M-HCl+Na]⁺; 261.1 [M-HCl+K]⁺

Z-Lys(Boc)-Gly-Gly-OBn: Using general procedure D starting from HCl.H₂N-Gly-Gly-OBn (1.12 g, 4.17 mmol, 1 eq.) and Z-Lys(Boc)-OH (1.68 g, 4.17 mmol, 1 eq.). Yellow oil (1.69 g, 69%).

MS (ESI⁺): 585.3 [M+H]⁺; 607.2 [M+Na]⁺; 623.2 [M+K]⁺

Z-Lys(HCl)-Gly-Gly-OBn: Using general procedure C starting from Z-Lys(Boc)-Gly-Gly-OBn (1.60 g, 2.79 mmol, 1 eq.). White solid (1.59 g, 100%).

MS (ESI⁺): 485.2 [M-HCl+H]⁺; 507.2 [M-HCl+Na]⁺; 523.2 [M-HCl+K]⁺

Boc-Ala-Gly-OBn: Using general procedure A with Boc-Ala-OH (400 mg, 2.1 mmol, 1 eq.) and HCl.H₂N-Gly-OBn (425 mg, 2.1 mmol, 1 eq.). Colorless oil (666 mg, 94%).

MS (ESI⁺): 359.2 [M+Na]⁺; 375.1 [M+K]⁺

TFA.H₂N-Ala-Gly-OBn: Using general procedure B starting from Boc-Ala-Gly-OBn (646 mg, 1.92 mmol, 1 eq.). Yellow oil (759 mg, 100%).

MS (ESI⁺): 237.1 [M-TFA+H]⁺; 259.1 [M-TFA+Na]⁺

Z-Lys(Boc)-Ala-Gly-OBn: Using general procedure D starting from TFA.H₂N-Ala-Gly-OBn (739 mg, 1.87 mmol, 1 eq.) and Z-Lys(Boc)-OH (711 mg, 1.87 mmol, 1 eq.). White solid (797 mg, 71%).

MS (ESI⁺): 621.4 [M+Na]⁺; 637.4 [M+K]⁺

Z-Lys(TFA)-Ala-Gly-OBn: Using general procedure B starting from Z-Lys(Boc)-Ala-Gly-OBn (777 mg, 1.30 mmol, 1 eq.). Yellow oil (947 mg, 100%).

MS (ESI⁺): 499.3 [M-TFA+H]⁺; 521.3 [M-TFA+Na]⁺; 537.3 [M-TFA+K]⁺

Boc-Gly-Ala-OBn: Using general procedure A with Boc-Gly-OH (400 mg, 2.29 mmol, 1 eq.) and HCl.H₂N-Ala-OBn (494 mg, 2.29 mmol, 1 eq.). Colorless oil (703 mg, 91%).

MS (ESI⁺): 359.2 [M+Na]⁺; 375.1 [M+K]⁺

TFA.H₂N-Gly-Ala-OBn: Using general procedure B starting from Boc-Gly-Ala-OBn (683 mg, 2.03 mmol, 1 eq.). Yellow oil (772 mg, 100%).

MS (ESI⁺): 237.1 [M-TFA+H]⁺; 259.1 [M-TFA+Na]⁺

Z-Lys(Boc)-Gly-Ala-OBn: Using general procedure D starting from TFA.H₂N-Gly-Ala-OBn (753 mg, 1.98 mmol, 1 eq.) and Z-Lys(Boc)-OH (753 mg, 1.98 mmol, 1 eq.). Yellow oil (939 mg, 79%).

MS (ESI⁺): 621.4 [M+Na]⁺; 637.4 [M+K]⁺

Z-Lys(TFA)-Gly-Ala-OBn: Using general procedure B starting from Z-Lys(Boc)-Gly-Ala-OBn (919 mg, 1.53 mmol, 1 eq.). Yellow oil (1.10 g, 100%).

MS (ESI⁺): 499.3 [M-TFA+H]⁺; 521.3 [M-TFA+Na]⁺

Z-Orn(Boc)-Ala-Ala-OBn: Using general procedure D starting from TFA.H₂N-Ala-Ala-OBn (878 mg, 2.41 mmol, 1.04 eq.) and Z-Orn(Boc)-OH (850 mg, 2.32 mmol, 1 eq.). White solid (879 mg, 63%).

MS (ESI⁺): 599.3 [M+H]⁺; 621.3 [M+Na]⁺; 637.3 [M+K]⁺

Z-Ornn(HCl)-Ala-Ala-OBn: Using general procedure C starting from Z-Orn(Boc)-Ala-Ala-OBn (874 mg, 1.46 mmol, 1 eq.). White solid (822 mg, 100%).

MS (ESI⁺): 499.3 [M-HCl+H]⁺; 521.2 [M-HCl+Na]⁺

Z-Dab(Boc)-Ala-Ala-OBn: Using general procedure D starting from TFA.H₂N-Ala-Ala-OBn (463 mg, 1.27 mmol, 1 eq.) and Z-Dab(Boc)-OH (447 mg, 1.27 mmol, 1 eq.). Z-Dab(Boc)-OH was prepared from Z-Dab(Boc)-OH.D-

CHA (dicyclohexylamine salt) as follows: The salt was diluted in dichloromethane, this solution was washed three times with a saturated aqueous solution of potassium hydrogenosulfate, dried over anhydrous sodium sulfate and concentrated under vacuum. White solid (402 mg, 54%).

MS (ESI$^+$): 585.3 [M+H]$^+$; 607.3 [M+Na]$^+$; 623.3 [M+K]$^+$

Z-Dab(HCl)-Ala-Ala-OBn: Using general procedure C starting from Z-Dab(Boc)-Ala-Ala-OBn (400 mg, 0.684 mmol, 1 eq.). White solid (413 mg, 100%).

MS (ESI$^+$): 485.2 [M-HCl+H]$^+$; 507.2 [M-HCl+Na]$^+$

Boc-Ala-Pro-OBn: Boc-Ala-OH (1.00 g, 5.28 mmol, 1 eq.) was dissolved in dichloromethane (8 mL) under $N_2$ atmosphere. HCl.H$_2$N-Pro-OBn (1.40 g, 5.81 mmol, 1.1 eq.) and 2-bromoethylpyridinium (1.59 g, 5.81 mmol, 1.1 eq.) were added sequentially. The reaction mixture was cooled to 0° C. and N,N-diisopropylethylamine (2.8 mL, 16.9 mmol, 3.2 eq.) was added dropwise. The mixture was allowed to warm to room temperature and stirred for 5 h. After completion of the reaction, the reaction mixture was diluted with dichloromethane (20 mL). The obtained solution was washed with an aqueous solution of citric acid (10%, 15 mL), then with an aqueous solution of sodium hydrogenocarbonate (5%, 15 mL) before being dried over anhydrous sodium sulfate and concentrated under vacuum. The obtained residue was purified by flash column chromatography to give Boc-Ala-Pro-OBn as a pale yellow oil (1.34 g, 67%).

MS (ESI$^+$): 399.2 [M+Na]$^+$

TFA.H$_2$N-Ala-Pro-OBn: Using general procedure B, starting from Boc-Ala-Pro-OBn (1.27 g, 3.7 mmol, 1 eq.). Pale brown oil (1.31 g, 100%).

MS (ESI$^+$): 277.2 [M-TFA+H]$^+$; 299.1 [M-TFA+Na]$^+$

Z-Lys(Boc)-Ala-Pro-OBn: Using general procedure D starting from Z-Lys(Boc)-OH (1.30 mg, 3.43 mmol, 1 eq.) and TFA.H$_2$N-Ala-Pro-OBn (1.34 mg, 3.43 mmol, 1 eq.). White solid (1.24 g, 57%).

MS (ESI$^+$): 639.3 [M+H]$^+$; 661.3 [M+Na]$^+$; 677.3 [M+K]$^+$

Z-Lys(TFA)-Ala-Pro-OBn: Using general procedure B, starting from Z-Lys(Boc)-Ala-Pro-OBn (1.08 g, 1.69 mmol, 1 eq.). Pale brown solid (1.1 g, 56%).

MS (ESI$^+$): 539.3 [M-TFA+H]$^+$

Boc-Pro-Ala-OBn: Using general procedure A with Boc-Pro-OH (2.0 g, 9.29 mmol, 1 eq.) and HCl.H$_2$N-Ala-OBn (2.04 mg, 9.29 mmol, 1 eq.). White solid (2.79 g, 80%).

MS (ESI$^+$): 399.2 [M+Na]$^+$; 415.2 [M+K]$^+$

TFA.H$_2$N-Pro-Ala-OBn: Using general procedure B starting from Boc-Pro-Ala-OBn (537 mg, 1.43 mmol, 1 eq.). Pale yellow solid (558 mg, 100%).

MS (ESI$^+$): 277.2 [M-TFA+H]$^+$; 299.1 [M-TFA+Na]$^+$

Z-Lys(Boc)-Pro-Ala-OBn: TFA.H$_2$N-Pro-Ala-OBn (542 mg, 1.39 mmol, 1.1 eq.) was dissolved in dichloromethane (7 mL) under $N_2$ atmosphere. Z-Lys(Boc)-OH (479 mg, 1.26 mmol, 1 eq.) and 2-bromoethylpyridinium (380 mg, 1.39 mmol, 1.1 eq.) were added sequentially. The reaction mixture was cooled to 0° C. and N,N-diisopropylethylamine (670 µL, 4.03 mmol, 3.2 eq.) was added dropwise. The mixture was allowed to warm to room temperature and stirred for 5 h. After completion of the reaction, the reaction mixture was diluted with dichloromethane (15 mL). The obtained solution was washed with an aqueous solution of citric acid (10%, 10 mL), then with an aqueous solution of sodium hydrogenocarbonate (5%, 10 mL) before being dried over anhydrous sodium sulfate and concentrated under vacuum. The obtained residue was purified by flash column chromatography to give Z-Lys(Boc)-Pro-Ala-OBn as a white solid (382 mg, 43%).

MS (ESI$^+$): 639.5 [M+H]$^+$; 661.5 [M+Na]$^+$; 677.4 [M+K]$^+$

Z-Lys(TFA)-Pro-Ala-OBn: Using general procedure B starting from Z-Lys(Boc)-Pro-Ala-OBn (358 mg, 0.56 mmol, 1 eq.). Pale brown solid (365 mg, 100%).

MS (ESI$^+$): 539.3 [M-TFA+H]$^+$

Z-Ala-Lys(Boc)-OMe: Using general procedure A starting from Z-Ala-OH (500 mg, 2.24 mmol, 1 eq.) and HCl.H$_2$N-Lys(Boc)-OMe (665 mg, 2.24 mmol, 1 eq.). Viscous colorless oil (863 mg, 83%).

MS (ESI$^+$): 466.3 [M+H]$^+$; 488.2 [M+Na]$^+$; 504.2 [M+K]$^+$

Z-Ala-Lys(Boc)-OH: To a solution of Z-Ala-Lys(Boc)-OMe (786 mg, 1.69 mmol) in tetrahydrofuran (49 mL) was added a solution of lithium hydroxide (121 mg, 3 eq.) in water (5.6 mL). The reaction mixture was stirred for 16 h then a solution of aqueous hydrochloric acid (1M) was added until pH 1 and the mixture was extracted 3 times with ethyl acetate. The combined organic layers were dried over anhydrous sodium sulfate and concentrated under vacuum to give a pale yellow oil (763 mg, 100%).

MS (ESI$^+$): 452.2 [M+H]$^+$; 474.2 [M+Na]$^+$; 490.2 [M+K]$^+$

Z-Ala-Lys(Boc)-Ala-OBn: Using general procedure A starting from Z-Ala-Lys(Boc)-OH (585 mg, 1.23 mmol, 1 eq.) instead of Boc-aa$_1$-OH and HCl.H$_2$N-Ala-OBn (265 mg, 1.23 mmol, 1 eq.). White solid (364 mg, 48%).

MS (ESI$^+$): 613.3 [M+H]$^+$; 635.3 [M+Na]$^+$; 651.3 [M+K]$^+$

Z-Ala-Lys(HCl)-Ala-OBn: Using general procedure C starting from Z-Ala-Lys(Boc)-Ala-OBn (364 mg, mmol, 1 eq.). White solid (326 mg, 100%).

MS (ESI$^+$): 513.3 [M-HCl+H]$^+$; 535.3 [M-HCl+Na]$^+$; 551.2 [M-HCl+K]$^+$

Boc-Tyr(OMe)-Ala-OBn: Using general procedure A starting from Boc-Tyr(OMe)-OH (1.35 g, 4.57 mmol, 1 eq.) and HCl.H$_2$N-Ala-OBn (1.084 mg, 5.03 mmol, 1.1 eq.). White solid (863 mg, 83%).

MS (ESI$^+$): 457.2 [M+H]$^+$; 479.2 [M+Na]$^+$; 495.2 [M+K]$^+$

HCl.H$_2$N-Tyr(OMe)-Ala-OBn: Using general procedure C starting from Boc-Tyr(OMe)-Ala-OBn (1.7 g, mmol, 1 eq.). White solid (1.51 g, 100%).

MS (ESI$^+$): 357.2 [M-HCl+H]$^+$; 379.2 [M-HCl+Na]$^+$

Z-Lys(Boc)-Tyr(OMe)-Ala-OBn: Using general procedure D starting from HCl.H$_2$N-Tyr(OMe)-Ala-OBn (1.53 g, 3.89 mmol, 1 eq.) and Z-Lys(Boc)-OH (1.63 g, 4.28 mmol, 1.1 eq.). Pale yellow solid (1.01 g, 40%).

MS (ESI$^+$): 720.4 [M+H]$^+$; 766.5 [M+K]$^+$

Z-Lys(HCl)-Tyr(OMe)-Ala-OBn: Using general procedure C starting from Z-Lys(Boc)-Tyr(OMe)-Ala-OBn (970 mg, 1.35 mmol, 1 eq.). Pale yellow solid (880 mg, 100%).

MS (ESI$^+$): 619.3 [M-HCl+H]$^+$; 641.3 [M-HCl+Na]$^+$; 657.3 [M-HCl+K]$^+$

Synthesis of Intermediate Compounds 2 and 4:

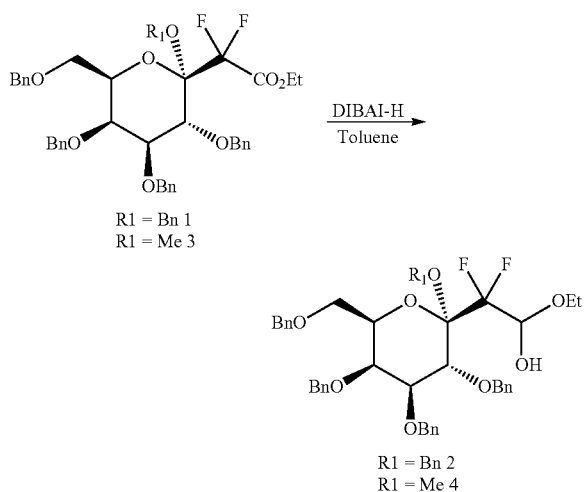

With R₁=Bn

To a cooled (−78° C.) solution of compound 1 (1.0 g, 1.33 mmol, 1 eq.), obtained from a process described in WO 2012/085221 A1, in anhydrous toluene (13 mL) was added dropwise a solution of diisobutylaluminium hydride (1.2 M in toluene, 1.4 mL, 1.66 mmol, 1.25 eq.) and the reaction mixture was stirred at the same temperature for 6 h 30 under nitrogen atmosphere. The reaction mixture was quenched with ethanol (3 mL), allowed to warm to −20° C., and stirred at this temperature for 15 minutes. A solution of Rochelle's salt (20%, 8 ml) was added, and the mixture was allowed to warm to room temperature and stirred for 1 h. The reaction mixture was extracted with ethyl acetate (3×30 mL). The combined organic layers were washed with brine (30 mL), dried over anhydrous sodium sulfate, filtered and concentrated in vacuo to give compound 2 (987 mg, colorless oil) which was used in the next step without any further purification.

Mass (ESI⁺): 777.4 [M+Na]⁺, 793.4 [M+K]⁺

With R₁=Me

The same procedure as above, using compound 3 (3.56 g, 5.26 mmol) described in *Bioorganic & Medicinal Chemistry Letters*, 2010, 20, 5251-5254 as starting material, leads to compound 4 (3.11 g, pale yellow oil).

Mass (ESI⁺): 701.3 [M+Na]⁺, 717.3 [M+K]⁺

Synthesis of Compounds 15, 21, 23, 25, 27, 29, 31, 33, 35, 37, 39 and 43

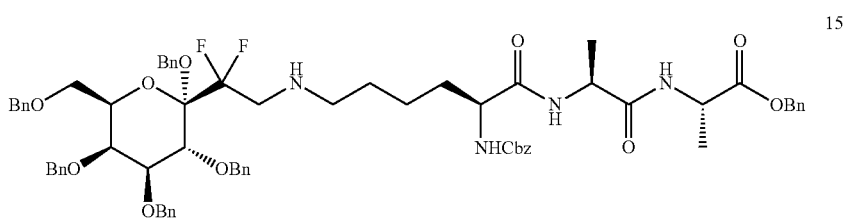

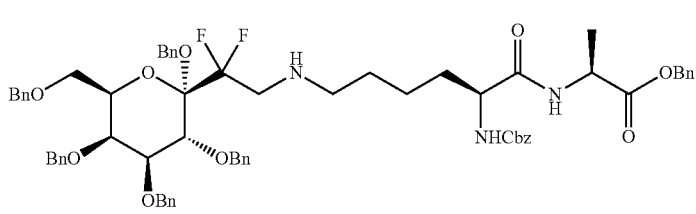

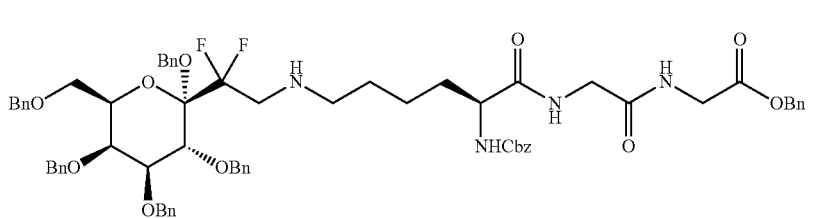

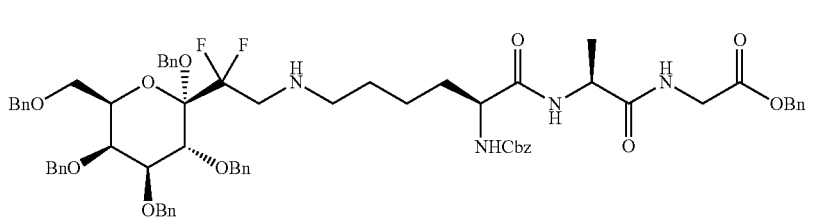

-continued
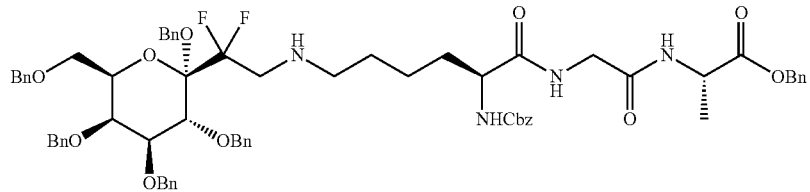
27
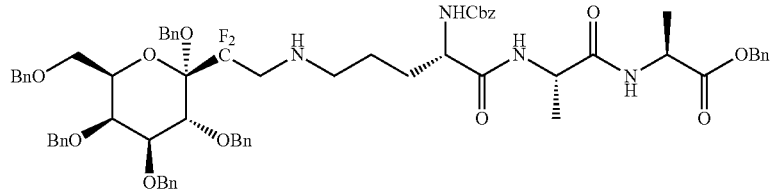
29
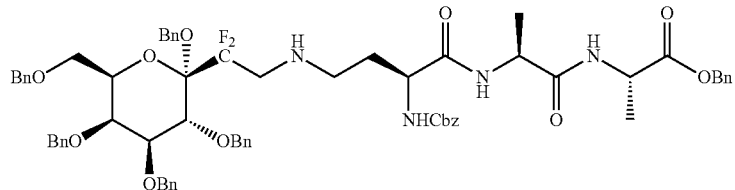
31
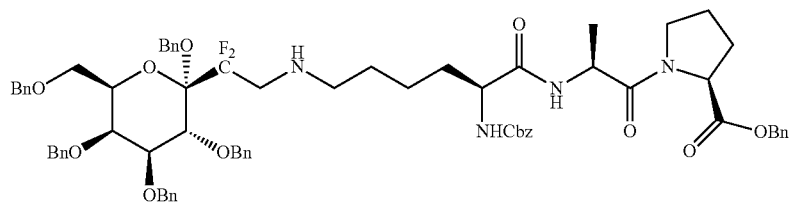
33
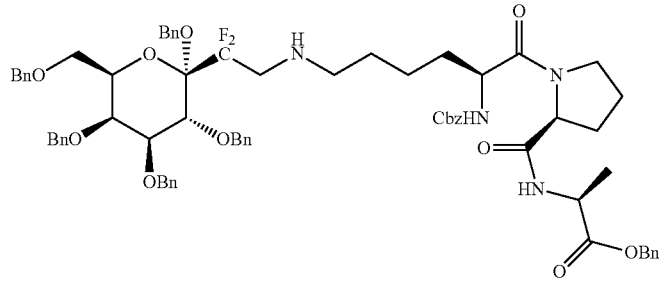
35
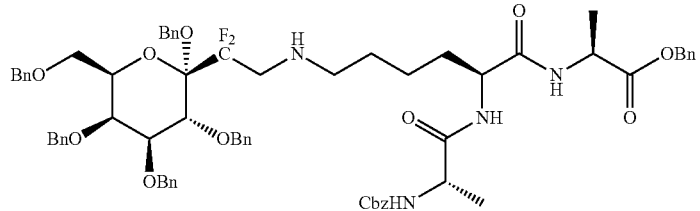
37

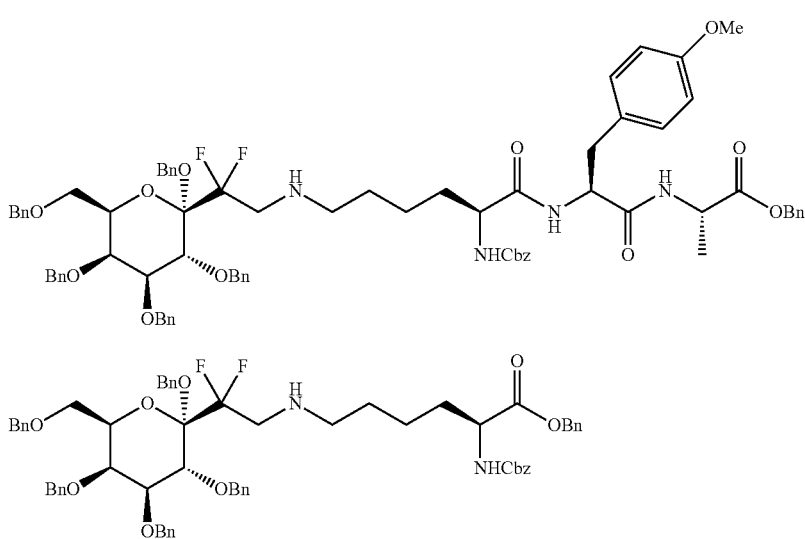

Peptide or amino acid condensation onto hemiketal 2 and subsequent reduction: Hemiketal 2 derivative was dissolved in dichloroethane (0.05M) under nitrogen atmosphere. Magnesium sulfate (3 eq.), the peptide or amino acid derivative (0.95 to 1 eq.) and PS-NEt$_2$ (3.2 mmol·g$^{-1}$, 2 eq.) were added sequentially. The reaction mixture was stirred 30 min at room temperature and then refluxed for 20 h. After completion of the reaction (monitored by $^{19}$F NMR) the reaction mixture was rapidly filtered over a plug of Celite® which was washed with dichloroethane (about 10% of the initial quantity). The obtained solution was cooled to 0° C. and sodium triacetoxyborohydride (2 eq.) and acetic acid (1 eq.) were added sequentially under nitrogen atmosphere. After 30 min stirring at 0° C., the reaction mixture was allowed to warm to room temperature and stirred overnight. A saturated aqueous solution of sodium hydrogenocarbonate was slowly added and the mixture was stirred for 2 h. The layers were separated and the aqueous one extracted with dichloromethane. The combined organic layers were washed with brine, dried over anhydrous sodium sulfate and concentrated under vacuum to yield the crude glycopeptide derivative which was purified by flash column chromatography.

Compound 15: Using general procedure starting from hemiketal 2 (9.63 g, 12.76 mmol, 1 eq.) and Z-Lys(TFA)-Ala-Ala-OBn (7.59 g, 12.12 mmol, 0.95 eq.). White solid (6.71 g, 46%).

MS (ESI$^+$): 1205.6 [M+H]$^+$

Compound 21: Using general procedure starting from hemiketal 2 (1.02 g, 1.35 mmol, 1 eq.) and Z-Lys(HCl)-Ala-OBn (751 mg, 1.35 mmol, 1 eq.). Pale yellow oil (1.14 g, 74%).

MS (ESI$^+$): 1134.5 [M+H]$^+$; 1156.5 [M+Na]$^+$

Compound 23: Using general procedure starting from hemiketal 2 (1.02 g, 1.35 mmol, 1 eq.) and Z-Lys(HCl)-Gly-Gly-OBn (786 mg, 1.35 mmol, 1 eq.). White solid (1.03 g, 65%).

MS (ESI$^+$): 1177.5 [M+H]$^+$; 1199.5 [M+Na]$^+$

Compound 25: Using general procedure starting from hemiketal 2 (1.01 g, 1.34 mmol, eq.) and Z-Lys(TFA)-Ala-Gly-OBn (924 mg, 1.27 mmol, 0.95 eq.). White solid (719 mg, 47%).

MS (ESI$^+$): 1191.5 [M+H]$^+$; 1213.5 [M+Na]$^+$; 1229.5 [M+K]$^+$

Compound 27: Using general procedure starting from hemiketal 2 (1.13 g, 1.49 mmol, 1 eq.) and Z-Lys(TFA)-Gly-Ala-OBn (1.02 g, 1.42 mmol, 0.95 eq.). Pale yellow oil (774 mg, 46%).

MS (ESI$^+$): 1191.5 [M+H]$^+$; 1213.5 [M+Na]$^+$; 1229.5 [M+K]$^+$

Compound 29: Using general procedure starting from hemiketal 2 (1.07 g, 1.42 mmol, 1 eq.) and Z-Orn(HCl)-Ala-Ala-OBn (802 mg, 1.42 mmol, 1 eq.). White solid (1.23 g, 73%).

MS (ESI$^+$): 1191.5 [M+H]$^+$

Compound 31: Using general procedure starting from hemiketal 2 (516 mg, 684 mmol, 1 eq.) and Z-Dab(HCl)-Ala-Ala-OBn (413 mg, 684 mmol, 1 eq.). Colorless oil (588 mg, 73%).

MS (ESI$^+$): 1177.5 [M+H]$^+$; 1199.5 [M+Na]$^+$; 1215.5 [M+K]$^+$

Compound 33: Using general procedure starting from hemiketal 2 (497 mg, 0.658 mmol, 1 eq.) and Z-Lys(TFA)-Ala-Pro-OBn (408 mg, 0.625 mmol, 0.95 eq.). Pale yellow oil (466 mg, 61%).

RMN $^{19}$F(CDCl$_3$, 282.5 MHz) (without $^1$H coupled): −110.1 (d, 2J$_{F\text{-}F}$=257 Hz), −111.0 (d, $^2$J$_{F\text{-}F}$=257 Hz)

Compound 35: Using general procedure starting from hemiketal 2 (396 mg, 0.524 mmol, 1 eq.) and Z-Lys(TFA)-Pro-Ala-OBn (326 mg, 0.498 mmol, 0.95 eq.). White solid (409 mg, 67%).

MS (ESI$^+$): 1231.6 [M+H]$^+$

Compound 37: Using general procedure starting from hemiketal 2 (448 mg, 0.594 mmol, 1 eq.) and Z-Ala-Lys(HCl)-Ala-OBn (331 mg, 0.594 mmol, 1 eq.). Colorless oil (470 mg, 66%).

MS (ESI$^+$): 1205.6 [M+H]$^+$; 1227.5 [M+Na]$^+$; 1243.5 [M+K]$^+$

Compound 39: Using general procedure starting from hemiketal 2 (1.01 g, 1.34 mmol, 1 eq.) and Z-Lys(HCl)-Tyr(OMe)-Ala-OBn (830 mg, 1.27 mmol, 0.95 eq.). White solid (1.02 g, 59%).

MS (ESI$^+$): 1311.6[M+H]$^+$; 1333.6[M+Na]$^+$; 1349.6 [M+K]$^+$

Compound 43: Using general procedure starting from hemiketal 2 (408 mg, 0.54 mmol, 1 eq.) and Z-Lys(HCl)-OBn (255 mg, 0.54 mmol, 1 eq.). Colorless oil (310 mg, 54%).

MS (ESI$^+$): 1063.4 [M+H]$^+$

Synthesis of Compounds 17, 22, 24, 26, 28, 30, 32, 34, 36, 38, 40 and 44
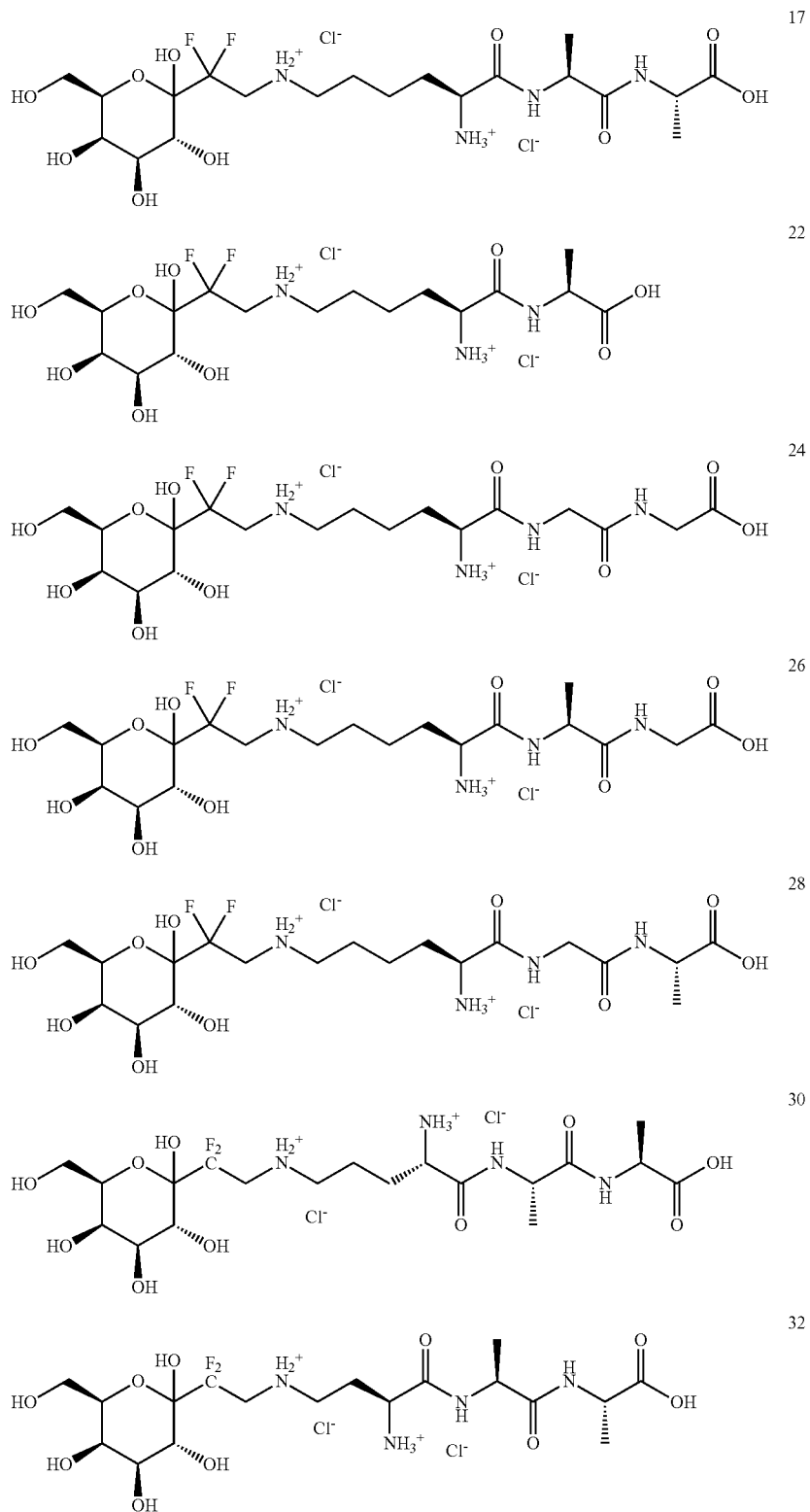

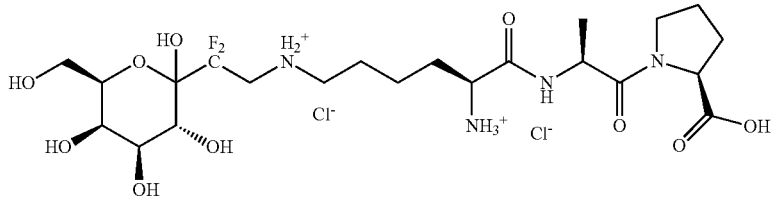

34

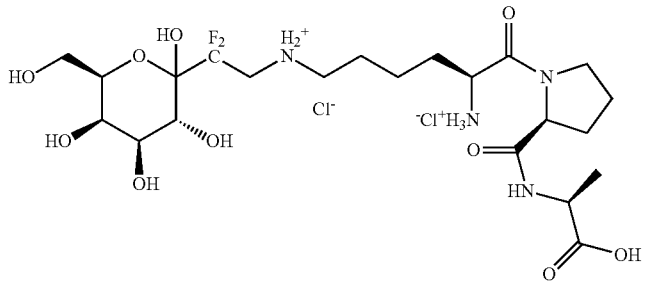

36

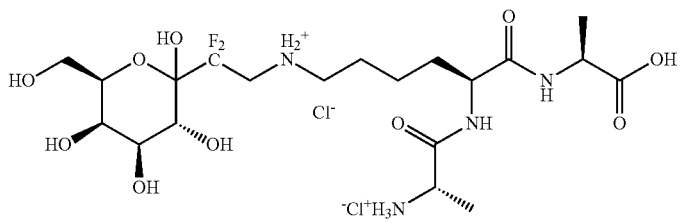

38

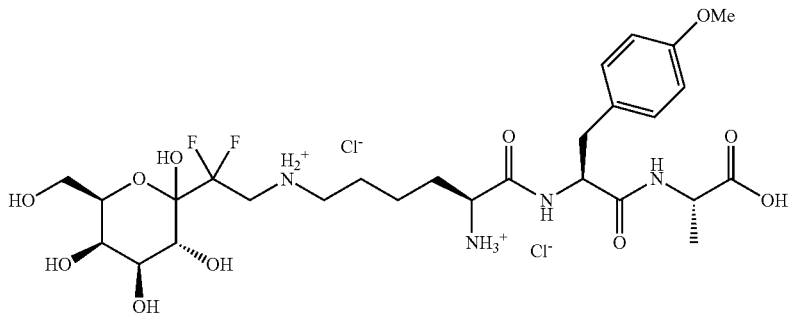

40

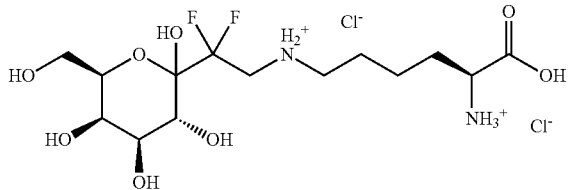

44

Glycopeptides deprotection using hydrogenolysis: To a solution of protected glycopeptide in tetrahydrofuran (0.025M) under inert atmosphere was added an aqueous solution of hydrochloric acid (1.0M, 3.6 eq.) followed by Pd/C (10% Pd, 0.1 eq.). The flask was purged with vacuum and filled with $H_2$ (3 times). The reaction mixture was vigorously stirred under $H_2$ atmosphere for 18 h. After completion of the reaction, the mixture was filtered (Millipore 0.45 μm) and the filter was washed with water. The filtrate was concentrated under vacuum and the obtained residue was dissolved in water and freeze dried to give the desired compound.

Compound 17: Using general procedure starting from compound 15 (6.48 g, 5.38 mmol, 1 eq.). White solid (3.21 g, 99%).

MS (ESI$^+$): 531.2 [M-2HCl+H]$^+$; 553.2 [M-2HCl+Na]$^+$; 569.2 [M-2HCl+K]$^+$

Compound 22: Using general procedure starting from compound 21 (702 mg, 0.619 mmol, 1 eq.). White solid (330 mg, 100%).

MS (ESI$^+$): 460.2 [M-2HCl+H]$^+$; 482.2 [M-2HCl+Na]$^+$; 498.1 [M-2HCl+K]$^+$

Compound 24: Using general procedure starting from compound 23 (700 mg, 0.595 mmol, 1 eq.). White solid (344 mg, 100%).

MS (ESI$^+$): 503.2 [M-2HCl+H]$^+$; 525.2 [M-2HCl+Na]$^+$; 541.2 [M-2HCl+K]$^+$

Compound 26: Using general procedure starting from compound 25 (640 mg, 0.537 mmol, 1 eq.). White solid (307 mg, 97%).

MS (ESI+): 517.2 [M-2HCl +H]+; 539.2 [M-2HCl +Na]+; 555.2 [M-2HCl +K]+

Compound 28: Using general procedure starting from compound 27 (604 mg, 0.507 mmol, 1 eq.). White solid (290 mg, 97%).

MS (ESI+): 517.2 [M-2HCl +H]+; 539.2 [M-2HCl +Na]+; 555.2 [M-2HCl +K]+

Compound 30: Using general procedure starting from compound 29 (700 mg, 0.588 mmol, 1 eq.). White solid (356 mg, 100%).

MS (ESI+): 517.2 [M-2HCl +H]+; 539.2 [M-2HCl +Na]+

Compound 32: Using general procedure starting from compound 31 (643 mg, 0.55 mmol, 1 eq.). Pale orange solid (290 mg, 92%).

MS (ESI−): 501.2 [M-2HCl −H]−

Compound 34: Using general procedure starting from compound 33 (436 mg, 0.354 mmol, 1 eq.). White solid (227 mg, 100%).

MS (ESI+): 557.2 [M-2HCl +H]+

Compound 36: Using general procedure starting from compound 35 (380 mg, 0.309 mmol, 1 eq.). White solid (196 mg, 100%).

MS (ESI+): 557.2 [M-2HCl +H]+

Compound 38: Using general procedure starting from compound 37 (470 mg, 0.39 mmol, 1 eq.). White solid (235 mg, 100%).

MS (ESI−): 529.3 [M-2HCl −H]−

Compound 40: Using general procedure starting from compound 39 (50 mg, 0.038 mmol, 1 eq.). White solid (21 mg, 78%).

MS (ESI−): 635.2 [M-2HCl −H]−

Compound 44: Using general procedure starting from compound 43 (750 mg, 0.705 mmol, 1 eq.). White solid (305 mg, 94%).

MS (ESI−): 387.1 [M-2HCl −H]−

I-2. Particular Procedures

Synthesis of Intermediate Compounds 5 and 6:

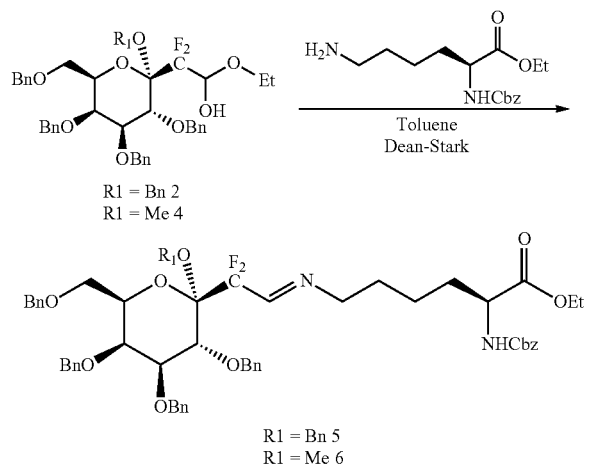

With $R_1$=Bn

Compound 2 (606 mg, 0.80 mmol, 1 eq.) and N-carboxy-benzoyl-ethyl-lysinate (485 mg, 1.61 mmol, 2 eq.) were refluxed in toluene (8 mL) using a Dean-Stark apparatus under nitrogen atmosphere. After 3 h, the mixture is concentrated in vacuo to obtain compound 5 which was engaged in the next step without further purification. $^{19}$F NMR (CDCl$_3$, 282.5 MHz) (without H coupled): −110.2 (d, J=263 Hz, 1F); −114.1 (d, J=263 Hz, 1F).

With $R_1$=Me

The same procedure as above, using compound 4 (1.08 g, 1.59 mmol) as starting material, leads to compound 6 which was engaged in the next step without further purification.

$^{19}$F NMR (CDCl$_3$, 282.5 MHz) (without H coupled): −109.7 (d, J=263 Hz, 1F); −114.5 (d, J=263 Hz, 1F).

Synthesis of Compounds 7 and 8:

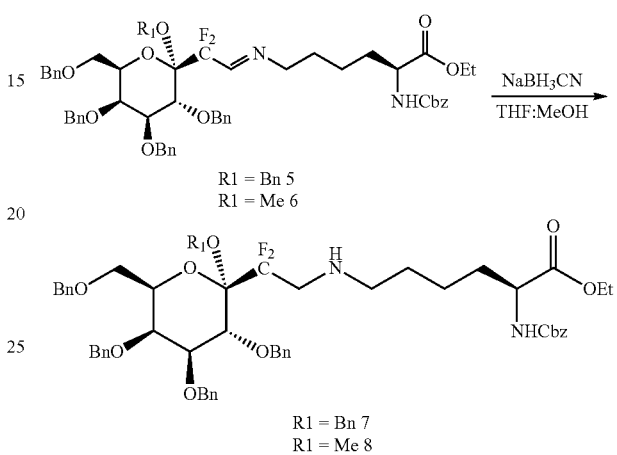

With $R_1$=Bn

Sodium cyanoborohydride (151 mg, 2.41 mmol, 3 eq.) was added to a solution of compound 5 (802 mg, 0.803 mmol, 1 eq.) in tetrahydrofuran (1.6 mL) and methanol (7.4 mL) under nitrogen atmosphere. The reaction mixture was stirred at room temperature for 16 h. A saturated aqueous ammonium chloride solution (8 mL) was added and the mixture was extracted with ethyl acetate (3×15 mL). The combined organic layers were washed with brine (15 mL), dried over anhydrous sodium sulfate, filtered and concentrated in vacuo. The residue was purified by flash column chromatography to yield compound 7 (382 mg, 31%, colorless oil).

Mass (ESI+): 1001.6 [M+H]+, 1023.5 [M+Na]+, 1039.5 [M+K]+

With $R_1$=Me

The same procedure as above, using compound 6 (1.47 g, 1.59 mmol) as starting material, leads to compound 8 (796 mg, 54%, pale brown oil).

Mass (ESI+): 925.3 [M+H]+

Alternative Synthesis of Compound 8 ($R_1$=Me) Using a Substitutive Approach:

Synthesis of Intermediate Compound 9 ($R_1$=Me):

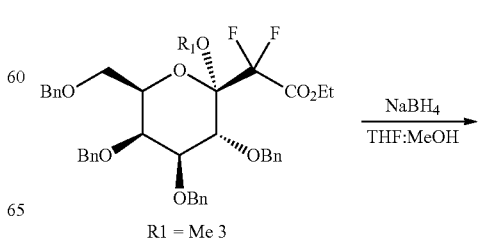

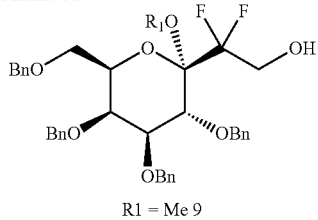

R1 = Me 9

Sodium borohydride (1 g, 26.4 mmol, 7 eq.) was added portionwise to a cooled (0° C.) solution of compound 3 (2.55 g, 3.77 mmol, 1 eq.) in methanol (30 mL) and THF (2.5 mL) under nitrogen atmosphere. The reaction mixture was allowed to warm to room temperature and stirred for 3 h 30. Saturated ammonium chloride solution (10 mL) and brine (10 mL) were added and the mixture was extracted with ethyl acetate (3×30 mL). The combined organic layers were washed with brine (30 mL), dried over anhydrous sodium sulfate, filtered and concentrated in vacuo to yield compound 9 (2.35 g, 98%, pale yellow oil).

Mass (ESI$^+$): 657.3 [M+Na]$^+$, 673.3 [M+K]$^+$ $^{19}$F NMR (CDCl$_3$, 282.5 MHz) (without H coupled): −113.6 (d, J=262 Hz, 1F); −114.6 (d, J=262 Hz, 1F).

Synthesis of Intermediate Compound 10 (R$_1$=Me):

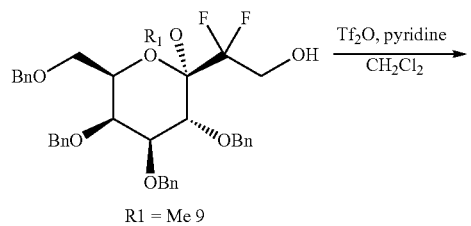

Pyridine (650 µL, 7.97 mmol, 2.2 eq.) and trifluoromethanesulfonic anhydride (1.3 mL, 7.97 mmol, 2.2 eq.) were added successively to a cooled (−78° C.) solution of compound 9 (2.3 g, 3.62 mmol, 1 eq.) in dichloromethane (36 mL) under nitrogen atmosphere. The reaction mixture was allowed to warm to room temperature and stirred for 2 h. Water (20 mL) was added and the mixture was extracted with dichloromethane (3×30 mL). The combined organic layers were dried over anhydrous sodium sulfate, filtered and concentrated in vacuo to yield compound 10 (2.79 g, 100%, pale orange oil).

Mass (ESI$^+$): 789.3 [M+Na]$^+$, 805.2 [M+K]$^+$ $^{19}$F NMR (CDCl$_3$, 282.5 MHz) (without H coupled): −113.4 (d, J=259 Hz, 1F); −115.6 (d, J=259 Hz, 1F).

Synthesis of Compound 8 (R$_1$=Me):

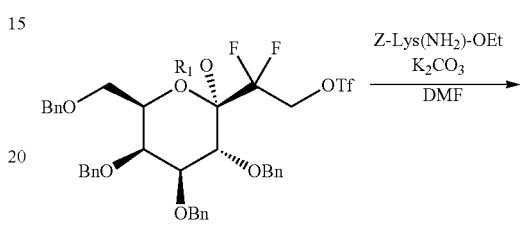

R1 = Me 10

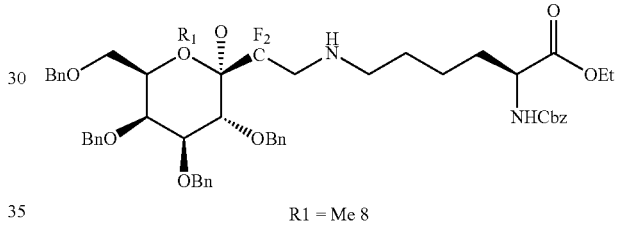

R1 = Me 8

To a solution of compound 10 (100 mg, 0.13 mmol, 1 eq.) in dry DMF (0.65 mL) under nitrogen atmosphere, was added a solution of Z-Lys(NH$_2$)—OEt (80 mg, 0.26 mmol, 2 eq.) in dry DMF (0.65 mL) and potassium carbonate (22 mg, 0.261 mmol, 2 eq.). The reaction mixture was stirred for 2 h 30 at room temperature and 15 h at 50° C. After cooling, saturated ammonium chloride solution (5 mL) and brine (5 mL) were added and the mixture was extracted with ethyl acetate (3×10 mL). The combined organic layers were washed with brine (2×20 mL), dried over anhydrous sodium sulfate, filtered and concentrated in vacuo to yield compound 8 (15 mg, 13%, colorless oil).

Mass (ESI$^+$): 925.3 [M+H]$^+$

Synthesis of Compounds 11 and 12:

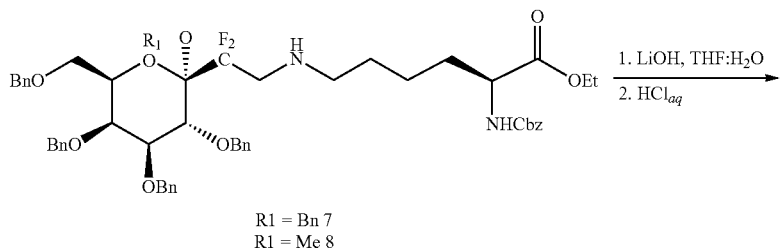

R1 = Bn 7
R1 = Me 8

-continued

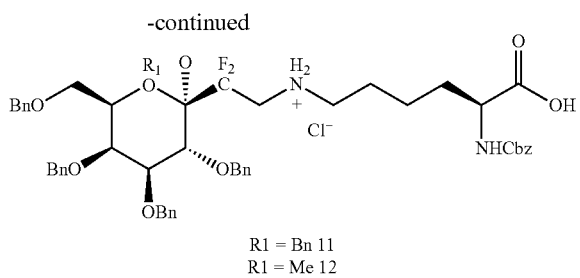

R1 = Bn 11
R1 = Me 12

With R₁=Bn

A 2N aqueous solution of lithium hydroxide (75 μL, 0.015 mmol, 2 eq.) was added dropwise to a cooled (0° C.) solution of compound 7 (75 mg, 0.075 mmol, 1 eq.) in tetrahydrofuran (750 μL). The reaction was then allowed to warm to room temperature and stirred for 18 h. A 1N aqueous solution of HCl was added until pH=1. The reaction mixture was extracted with ethyl acetate (3×8 mL). The combined organic layers were washed with brine (8 mL), dried over anhydrous sodium sulfate, filtered and concentrated in vacuo to afford crude compound 11 (76 mg, 93%, pale orange solid) which was used in the next step without further purification.

Mass (ESI$^+$): 973.3 [M-HCl+H]$^+$, 995.4 [M-HCl+Na]$^+$ $^{19}$F NMR (CDCl$_3$, 282.5 MHz) (without H coupled): −106.8 (d, J=261 Hz, 1F); −109.6 (d, J=261 Hz, 1F).

With R₁=Me

The same procedure as above, using compound 8 (604 mg, 0.652 mmol) as starting material, leads to compound 12 (578 mg as a pale orange solid, 95%).

Mass (ESI$^+$): 897.5 [M-HCl+H]$^+$, 919.5 [M-HCl+Na]$^+$, 935.4 [M-HCl+K]$^+$ $^{19}$F NMR (CDCl$_3$, 282.5 MHz) (without H coupled): −106.1 (d, J=263 Hz, 1F); −108.7 (d, J=263 Hz, 1F).

Synthesis of Intermediate Compounds 13 and 14:

R1 = Bn 2
R1 = Me 4

R1 = Bn 13
R1 = Me 14

With R₁=Bn

Compound 2 (45 mg, 0.073 mmol, 1 eq.) and Z-Lys(NH₂)AlaAla-OBn (75 mg, 0.15 mmol, 2 eq.) were refluxed in toluene (5 mL) using a Dean-Stark apparatus under nitrogen atmosphere. After completion of the reaction, the mixture is concentrated in vacuo to obtain compound 13 which was engaged in the next step without further purification.

$^{19}$F NMR (CDCl$_3$, 282.5 MHz) (without H coupled): −110.3 (d, J=263 Hz, 1F); −114.0 (d, J=263 Hz, 1F).

With R₁=Me

The same procedure as above, using compound 4 (200 mg, 0.32 mmol) as starting material, leads to compound 14 which was engaged in the next step without further purification.

$^{19}$F NMR (CDCl$_3$, 282.5 MHz) (without H coupled): −109.5 (d, J=264 Hz, 1F); −114.1 (d, J=264 Hz, 1F).

Alternative Synthesis of Intermediate Compound 13 (R₁=Bn):

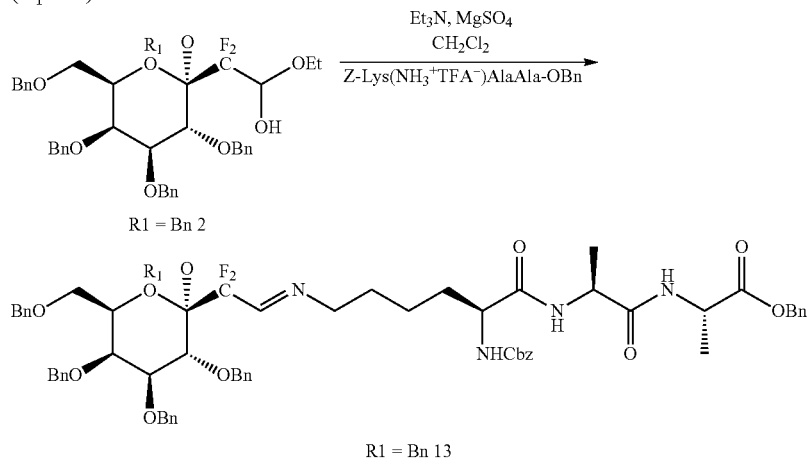

R1 = Bn 2

R1 = Bn 13

With R₁=Bn

Triethylamine (116 μL, 0.83 mmol, 1 eq.) was added dropwise to a stirred solution of compound 2 (628 mg, 0.83 mmol, 1 eq.) in dichloromethane (8.3 mL) under nitrogen atmosphere, Z-Lys(NH₃⁺TFA⁻)AlaAla-OBn (521 mg, 0.83 mmol, 1 eq.) and anhydrous magnesium sulfate (151 mg, 1.25 mmol, 1.5 eq.) were successively added and the mixture was stirred at room temperature for 3 h before being filtered. The filter was washed with a small amount of dichloromethane and the filtrate was washed with water (5 mL), dried with anhydrous magnesium sulfate and evaporated to give pure compound 13 (878 mg, 88%, colorless oil).

¹⁹F NMR (CDCl₃, 282.5 MHz) (without H coupled): −110.3 (d, J=263 Hz, 1F); −114.0 (d, J=263 Hz, 1F).

Alternative Synthesis of Compound 15 and Synthesis of Compound 16:

To a solution of compound 11 (347 mg, 0.34 mmol, 1 eq.) in DMF (3.5 mL), under nitrogen atmosphere, was added a solution of TFA⁻⁺H₃N-AlaAla-OBn (163 mg, 0.45 mmol, 1.3 eq.) in DMF (3.5 mL), PyBOP (521 mg, 0.722 mmol, 2.1 eq.), N-methylmorpholine (150 μL, 13.8 mmol, 4 eq.). The reaction mixture was stirred for 72 hours. Brine (4 mL) was added and the reaction mixture was extracted with ethyl acetate (3×8 mL). The combined organic layers were washed with an aqueous 10% citric acid solution (8 mL), 1N aqueous sodium hydroxide (8 mL) and brine (2×8 mL), dried over anhydrous sodium sulfate, filtered and concentrated in vacuo. The residue was purified by flash column chromatography to yield compound 15 (219 mg, 53%, white solid).

Mass (ESI⁺): 1205.4 [M+H]⁺

With R₁=Me

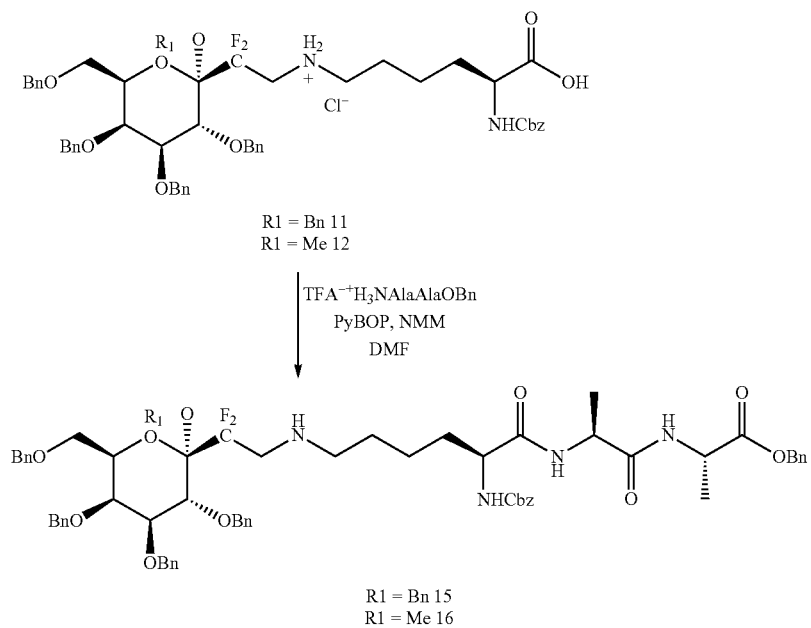

R1 = Bn 11
R1 = Me 12

TFA⁻⁺H₃NAlaAlaOBn
PyBOP, NMM
DMF

R1 = Bn 15
R1 = Me 16

With R₁=Bn

The same procedure as above, using compound 12 (556 mg, 0.595 mmol) as starting material, leads to compound 16 (544 mg as a pale yellow oil, 81%).

Mass (ESI⁺): 1129.4 [M+H]⁺, 1151.5 [M+Na]⁺, 1167.5 [M+K]⁺

Alternative Synthesis of Compounds 15 and 16:

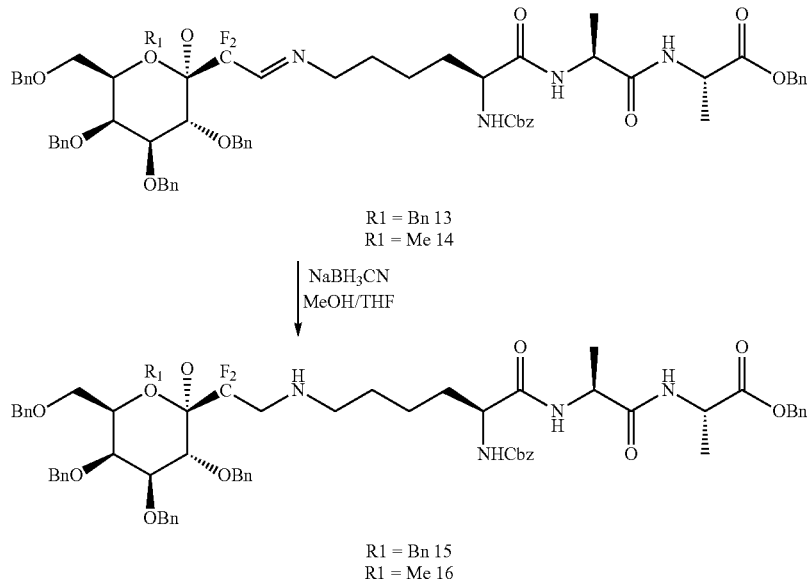

With R₁=Bn

Sodium cyanoborohydride (32 mg, 0.51 mmol, 6.9 eq.) was added to a solution of compound 13 (88 mg, 0.073 mmol, 1 eq.) in tetrahydrofuran (0.8 mL) and methanol (1.9 mL) under nitrogen atmosphere. The reaction mixture was stirred at room temperature for 20 h. A saturated aqueous ammonium chloride solution (10 mL) was added and the mixture was extracted with ethyl acetate (3×10 mL). The combined organic layers were washed with brine (20 mL), dried over anhydrous sodium sulfate, filtered and concentrated in vacuo. The residue was purified by flash column chromatography to yield compound 15 (57 mg, 68%, pale yellow solid).

Mass (ESI⁺): 1205.6 [M+H]⁺

With R₁=Me

The same procedure as above, using compound 14 (364 mg, 0.32 mmol) as starting material, leads to compound 16 (113 mg, 32%, colorless oil).

Mass (ESI⁺): 1129.5 [M+H]⁺, 1151.5 [M+Na]⁺, 1167.5 [M+K]⁺

Synthesis of Compound 18:

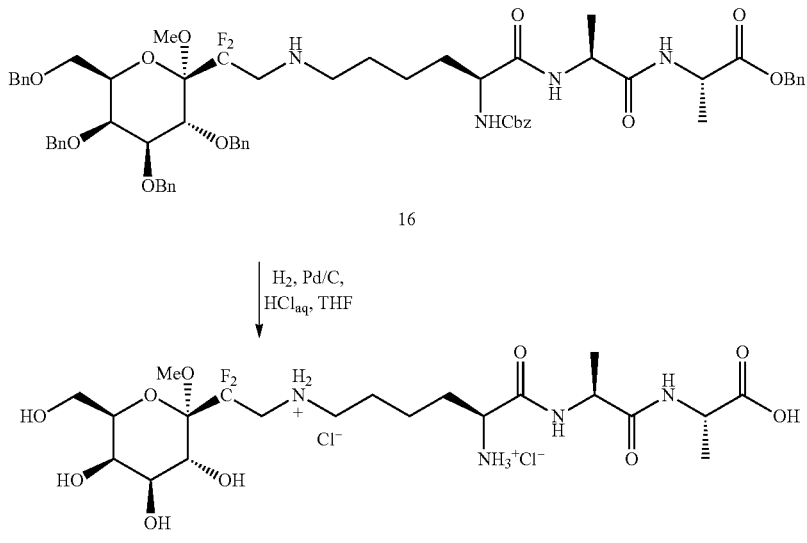

Compound 16 (100 mg, 0.089 mmol, 1 eq.) was dissolved in tetrahydrofuran (798 μL) and aqueous hydrochloric acid (2 M, 88 μL, 2 eq.). The flask was placed under nitrogen atmosphere and Pd/C 10% (30 mg, 0.32 eq.) was added. The flask was then filled with a hydrogen atmosphere and the reaction mixture was stirred for 24 hours before being Millipore filtered and concentrated in vacuo. The residue was dissolved in water, Millipore filtered (0.2 μm) and freeze dried to yield compound 18 (55 mg, 100%) as a pale orange solid.

Mass (ESI$^+$): 545.3 [M-2HCl+H]$^+$, 562.4 [M-2HCl+NH$_4$]$^+$ $^{19}$F NMR (CDCl$_3$, 282.5 MHz) (without H coupled): −109.1 (d, J=258 Hz, 1F); −110.8 (d, J=258 Hz, 1F).

Synthesis of Compound 19:

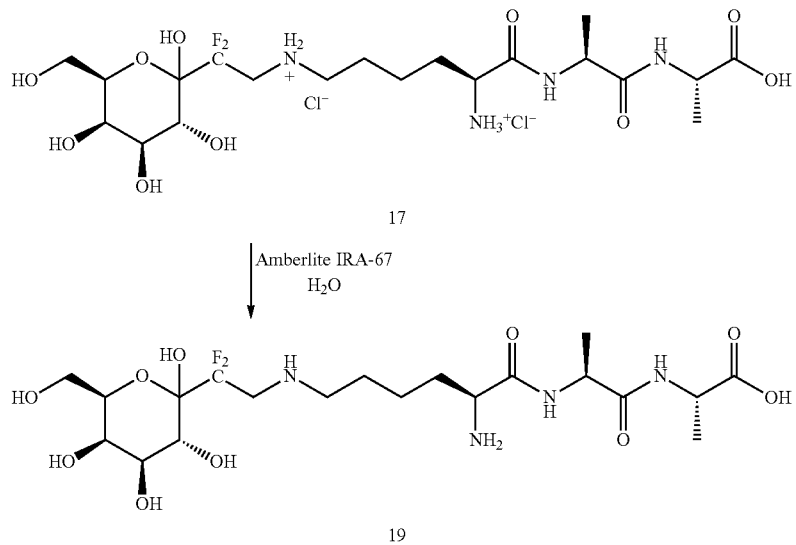

Compound 17 (323 mg, 0.54 mmol) was dissolved in water (7 mL) and Amberlite™ IRA-67 (1.3 g, previously washed with water) was added. The reaction mixture was stirred for 3 hours at room temperature before being Millipore filtered (0.2 μm), diluted with water and freeze dried to yield compound 19 (223 mg, 78%).

Mass (ESI$^+$): 531.2 [M+H]$^+$, 553.2 [M+Na]$^+$, 569.2 [M+K]$^+$

Synthesis of Compound 20:

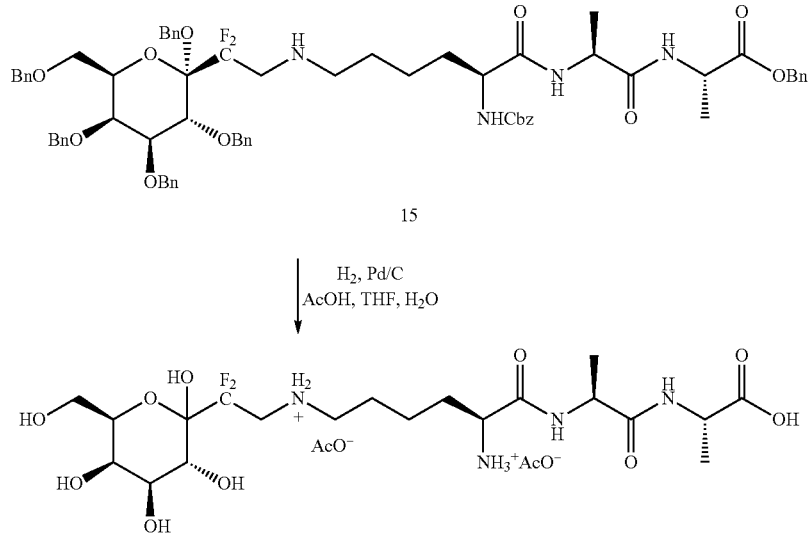

Compound 15 (150 mg, 0.124 mmol, 1 eq.) was dissolved in tetrahydrofuran (1.5 mL), water (1.5 mL) and acetic acid (5.3 mL). The flask was placed under nitrogen atmosphere and Pd/C 10% was added (26 mg, 0.2 eq.). The flask was then filled with a hydrogen atmosphere and the reaction mixture was vigorously stirred for 24 hours before being Millipore filtered and concentrated in vacuo. The residue was dissolved in water, Millipore filtered (0.2 μm) and freeze dried to yield compound 20 (66 mg, 82%) as a pale yellow solid.

Mass (ESI$^+$): 531.2 [M-2AcOH+H]$^+$, 553.2 [M-2AcOH+Na]$^+$, 569.2 [M-2AcOH+K]$^+$ Alternative Synthesis of Compound 20:

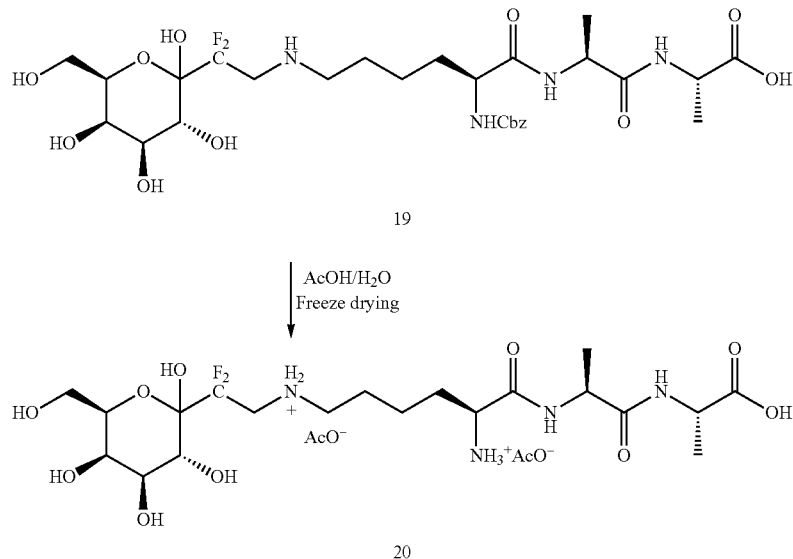

Compound 19 was dissolved in water (10.4 mL). AcOH (6 eq., 1 M, 2.34 mL, 2.34 mmol) was added dropwise and the mixture was manually agitated several times during 1 h 30. The mixture was then freeze dried to give compound 20 (244 mg, 0.375 mmol, 96%) as a white solid.

Mass (ESI$^+$): 531.2 [M-2AcOH+H]$^+$, 553.2 [M-2AcOH+Na]$^+$, 569.2 [M-2AcOH+K]$^+$ Synthesis of Compounds 41 and 42:

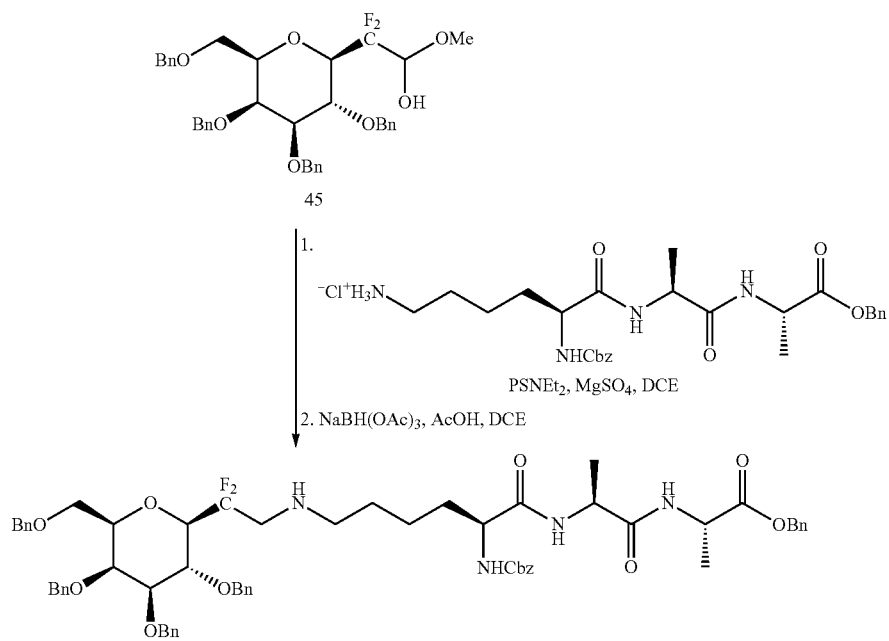

Hemiketal 45 (1g, 1.58 mmol, 1 eq.) was dissolved in dichloroethane (32 mL) under nitrogen atmosphere. Magnesium sulfate (570 mg, 4.73 mmol, 3 eq.), Z-Lys(HCl)-Ala-Ala-OBn (820 mg, 1.50 mmol, 0.95 eq.) and PS-NEt$_2$ (3.2 mmol·g$^{-1}$, 980 mg, 3.15 mmol, 2 eq.) were added sequentially. The reaction mixture was stirred 30 min at room temperature and then refluxed for 20 h. After completion of the reaction (monitored by $^{19}$F NMR) the reaction mixture was rapidly filter over a plug of Celite® which was washed with dichloroethane. The obtained solution was cooled to 0° C. and sodium triacetoxyborohydride (634 mg, 2.99 mmol, 2 eq.) and acetic acid (86 µl, 1.50 mmol, 1 eq.) were added sequentially under nitrogen atmosphere. After 30 min stirring at 0° C., the reaction mixture was allowed to warm to room temperature and stirred overnight. A saturated aqueous solution of sodium hydrogenocarbonate was slowly added and the mixture was stirred for 2 h. The layers were separated and the aqueous one extracted with dichloromethane. The combined organic layers were washed with brine, dried over anhydrous sodium sulfate and concentrated under vacuum to yield the compound 41 as a white solid (611 mg, 37%).

MS (ESI$^+$): 1099.4 [M+H]$^+$; 1121.4 [M+Na]$^+$; 1137.4 [M+K]$^+$

Synthesis of Intermediate Compound 45:

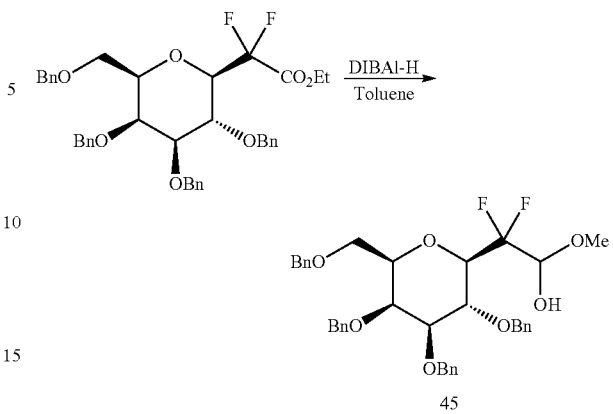

To a cooled (−78° C.) solution of difluoroester (2.19 g, 3.39 mmol, 1 eq.), synthesized according to *Synlett* 2005,17, 2627-2630 and *Org. Lett.* 2002, 4, 757-759—see also WO 2004/014928, WO 2007/125203 and WO 2007/125194, in anhydrous toluene (34 mL) was added a solution of diisobutylaluminium hydride (1.2M in toluene; 3.7 mL; 4.4 mmol; 1.2 eq.) and the resultant mixture was stirred for 3 h at this temperature. The reaction was then quenched with methanol

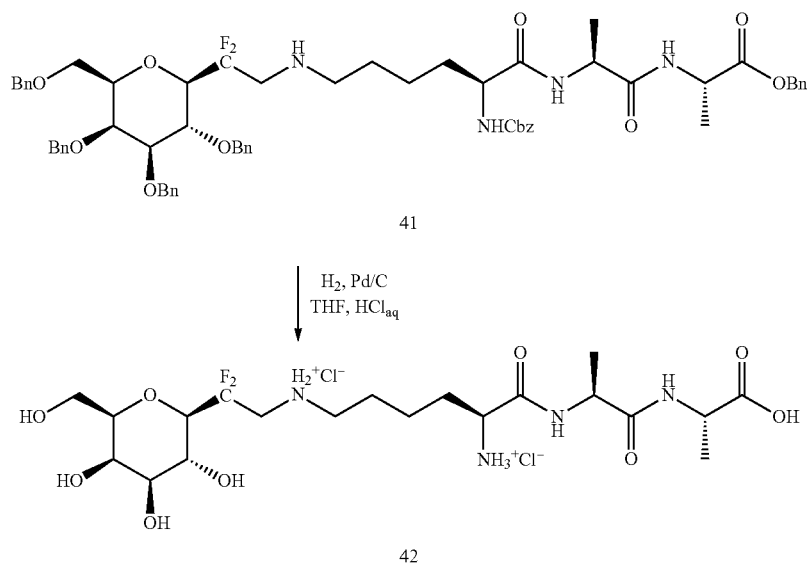

To a solution of compound 41 (585 mg, 0.45 mmol, 1 eq.) in THF (17.8 mL) under inert atmosphere was added an aqueous solution of hydrochloric acid (1.61 ml, 1.61 mmol, 3.6 eq.) followed by Pd/C (10% Pd, 4.7 mg, 0.045 mmol, 0.1 eq.). The flask was purged with vacuum and filled with H$_2$ (3 times). The reaction mixture was vigorously stirred under H$_2$ atmosphere for 18 h. After completion of the reaction, the mixture was filtered (Millipore 0.45 µm) and the filter was washed with water. The filtrate was concentrated under vacuum and the obtained residue was dissolved in water and freeze dried to give compound 42 as a pale orange solid (262 mg, 100%).

MS (ESI$^+$): 515.3 [M-2HCl +H]$^+$; 537.2 [M-2HCl +Na]$^+$; 553.2 [M-2HCl +K]$^+$ (6 mL) and the solution was warmed to −20° C. for 15 min. A Rochelle's salt solution (20%, 60 mL) was then added and the solution was vigorously stirred for 30 min. The mixture was then extracted with ethyl acetate. The combined organic extracts were washed with brine, dried over magnesium sulfate, filtered and evaporated in vacuo to give compound 45 as a colorless oil (2.15 g, 93%).

Mass (ESI$^+$): 652.2 [M+H$_2$O]$^+$

II—Biological Activity:

II-1. Effect of Glycopeptide 17 on the Preservation/Protection of Neonatal Skin Fibroblasts Under Starvation Conditions. Evaluation by Trypan Blue Exclusion Method.

Materials and Methods

Subculturing

The neonatal skin fibroblasts (Cell line: CCD-27SK, ATCC number CRL-1475) were grown with DMEM medium supplemented with Fetal Bovine Serum 10% final, antibiotics (Penicillin/Streptomycin) 1% final and Amphotericin B 0.1% final.

Fibroblasts were grown in 75 cm² culture flask to 80% confluence, in 37° C. and 10% $CO_2$ incubator. The medium was changed every two days by 37° C. preheated fresh medium.

The cell viability percentages from cultures under starvation conditions were compared with control culture for several days after their addition (D0, D3, D4, D5, D6, D7, D10, D12).

Results

The results were plotted in the histogram of FIG. 1 which represents the evolution of fibroblasts viability in vitro during a 12 days period, as well as on the table 1 below.

TABLE 1

| | Percentage of viability for 12 days | | | | | | | |
|---|---|---|---|---|---|---|---|---|
| Culture conditions | D 0 | D 3 | D 4 | D 5 | D 6 | D 7 | D 10 | D 12 |
| Surviving Control | 97.43 ± 1.30 | 95.69 ± 2.97 | 96.16 ± 1.27 | 93.49 ± 1.68 | 91.10 ± 2.24 | 91.29 ± 0.90 | 95.21 ± 1.37 | 90.33 ± 2.46 |
| Serum-Free Control | 96.55 ± 1.22 | 92.73 ± 1.03 | 76.94 ± 4.03 | 59.07 ± 5.86 | 33.54 ± 3.22 | 15.31 ± 3.46 | 0.00 ± 0.00 | 0.00 ± 0.00 |
| Compound 17 at 5 mg/mL in serum free medium | 96.69 ± 1.85 | 91.03 ± 1.88 | 88.98 ± 2.48 | 86.65 ± 4.26 | 85.53 ± 1.57 | 83.20 ± 3.72 | 80.62 ± 3.72 | 77.03 ± 2.02 |

Starvation Medium
  This medium was composed of 45% subculturing medium without Fetal Bovine Serum mixed with 55% of Phosphate Buffer Saline 1× containing EDTA (final concentration of 0.45 mM). This was referred to as serum-free medium.
Product Preparation
  Compound 17 (MM=603.4 g/mol) was diluted in starvation medium to 5 mg/ml final and pH was adjusted at 7.4 by addition of NaOH 1N.
General Experimental Procedure
Assays on 96 Well Plates
  Fibroblast cells were concentrated to $2.10^5$ cells/ml and 100 µl of cell suspension was added in wells of a 96-well plate and incubated in 37° C. and 10% $CO_2$ incubator for 4 hours.
  After cell adhesion the medium was changed and plates were incubated (37° C.-10% $CO_2$) to perform the assay as follow:
    One plate for each sampling times: D0, D3, D4, D5, D6, D7, D10, D12 days
    Three wells for each condition (triplicate count) added with 120 µl of culture medium (surviving control), starvation medium (serum-free control) or compound 17 solution at 5 mg/ml.
Viability Assay
  Cell Viability was evaluated by the Trypan blue exclusion technique based on the principle that live cells possess intact cell membranes that exclude the Trypan blue dye. So, only the dead cells are blue at microscopic observation.
    For sampling, 110 µl of Trypan Blue (SIGMA T8154) was added to 110 µl of trypsinated cell suspension of matching well for counting.
    200 µl of the trypan blue/cell mixture are dropped to a hemacytometer. Cells are counting by using a Neubauer-counting chamber. The unstained (viable) and stained (nonviable) cells are counted separately on 9 areas of 1 mm² forming a large square of 9 mm² and added to obtain the total number of cells per sample. An average of three counts was used to calculate the viability percentage as:

[Number of viable cells/total number of cells]*100

The surviving control showed a very good viability between D0 and D12 (viability>90%).

The cells in starvation medium (serum-free control) showed a clear decrease of their viability from D5 (59%); this phenomenon was greatly accentuated at D6 (34%), D7 (15%) to reach 100% of mortality at D10.

The viability of cells cultured in starvation medium but treated with compound 17 at 5 mg/ml, decreased very slightly between D0 (97%) and D12 (77%) and remained clearly higher than the serum-free control. Thus compound 17 showed a significant preservative/protective effect on skin fibroblasts since cells have been maintained in a healthy state under unfavorable conditions for growth.

II-2. Effect of Glycopeptides on the Preservation/Protection of Human Dermis Fibroblasts or Epithelial Nasal Cells in Different Stress Conditions.

Different stress conditions have been tested to evaluate the preservative/protective effect of several compounds on 2 types of cells: human skin fibroblasts (deprivation, UV stress, oxidative stress or bacterial stress) or human nasal epithelial cells (deprivation). The different protocols are described hereafter.

Materials and Methods
Subculturing
  The human neonatal skin fibroblasts (cell line: CCD-27SK, ATCC CRL-1475) were grown with DMEM medium supplemented with FBS 10% final, antibiotics (mix Dutscher L0010, Penicillin/Streptomycin/Amphotericin B) 1% final and L-Glutamine 1% final. The human nasal epithelial cells (cell line: RPMI2650, ATCC CCL-30) were grown with MEM medium supplemented with 10% of FBS, 1% of antibiotics and 1% of L-Glutamine.
  Cells were grown in 75 cm² culture flasks, in 37° C. and 10% $CO_2$ incubator, until 80% confluence and then subcultured in 3 flasks. The medium was changed every two days by 37° C. preheated fresh medium.
Assay Media
  For starvation assay, the medium was composed of 45% subculturing medium, devoid of FBS, mixed with 55% of PBS 1× containing EDTA (final concentration of 0.45 mM). This was referred to as starvation medium.
  For oxidative, bacterial and UV stress the medium was composed of 45% subculturing medium mixed with 55% of PBS 1× containing EDTA (final concentration of 0.45 mM).

Compound Solutions

The tested compounds were solubilized in PBS (10% of total volume) and then diluted in appropriate assay medium at definite final concentration. When necessary, the pH was adjusted at 7.4 by addition of NaOH 1N.

General Experimental Procedure

Assays on 24-Well Plates

Cells were concentrated to $1.10^5$ cells/ml and 500 µl of cell suspension was added in wells of a 24-well plate and incubated in 37° C. and 10% $CO_2$ incubator.

After 3 days of incubation the medium was removed in order to perform the assay in a way depending on the stress condition.

Several controls were performed i.e. the positive control (no stress) which was considered as 100% of viability and the stress control (stress, no compound) which was compared with the assay (stress+compound) to show a potential preservative effect of the tested compounds.

In the case of bacterial stress, the lysis of cells was compared between 3 assays only (stress+compound at 3 different concentrations).

Induced stresses were performed as follow:

Starvation

Three wells for each condition (triplicate count) were added with 1 ml of culture medium (positive control) or starvation medium (stress control) or starvation medium added with tested compounds at definite concentrations. Plates were incubated at 37° C. with 10% of $CO_2$ for different times (1, 4, 6, 7 or 8 days) and then the cell viability was analyzed using the neutral red uptake method.

Oxidative Stress

Three wells for each condition (triplicate count) were added with 0.8 ml of culture medium (control) or each tested compound solution. Plates were incubated at 37° C. with 10% of $CO_2$ for 24 h.

Then oxidative stress was performed as follow: 0.2 ml of solution at 500 µM of $H_2O_2$ was added in wells except for negative control where 0.2 ml of culture medium were added.

Plates were incubated at 37° C. with 10% of $CO_2$ for different time of exposure (1 h and 24 h) and then the cell viability was analyzed using the neutral red uptake method.

UV Stress

Three wells for each condition (triplicate count) were added with 1ml of culture medium (control) or each tested compound solution.

Plates were incubated at 37° C. with 10% of $CO_2$ for 24 h.

Then UV stress was performed as follow: plates were subjected to 11 Joules/$cm^2$ in a UVA CUBE 400 (HONLE UV technology) and the irradiated plates were incubated at 37° C. with 10% of $CO_2$ for different times (1 h, 3 h and 24 h) and then the cell viability was analyzed using the neutral red uptake method.

Bacterial Stress

Preparation of Supernatant of *Staphylococcus aureus* Culture.

Precultured of *Staphylococcus aureus* was performed in Tryptic Soy Broth during 16 hours at 37° C. under stirring.

After incubation, bacteria were harvested by centrifugation (4000 rpm, 10 minutes) and suspended to obtain $OD_{620\ nm}$=3.3 in culture medium of cells without antibiotics. Culture was performed during 24 hours at 37° C. under stirring. Then the supernatant was recovered after centrifugation (4000 rpm, 10 minutes) and sterilized by 0.22 µm filtration. Antibiotics (mix Dutscher L0010, Penicillin/Streptomycin/Amphotericin B) were added at 1% to respect proportion of culture medium of cells. The supernatant stored at deep freezer, contains all toxins and metabolic wastes produced during bacterial growth.

Assay.

Assay was performed as follow:

Supernatant of *Staphylococcus aureus* culture was diluted (1/2) in culture medium.

Three wells for each condition (triplicate count) were added with 0.5 ml of tested compound solution. Plates were incubated at 37° C. with 10% of $CO_2$ for 24 hours.

Then the bacterial stress was performed using the diluted supernatant of *Staphylococcus aureus* culture to stress the cells. Solutions in each well was removed and replaced by 0.5 ml of diluted supernatants and 0.5 ml of 2× concentrated compound solutions. Plates were incubated at 37° C. with 10% of $CO_2$ for 48 h.

Then the cell lysis was analyzed using the Lactate Dehydrogenase (LDH) bioassay.

Viability Assay (Neutral Red Uptake)

The neutral red uptake assay was used for the determination of cell viability. This assay is based on the ability of viable cells to incorporate and bind the supravital dye neutral red in its lysosomes. So, only the viable cells are dyed. At different times after the stress assay (T0), the plates were incubated with neutral red solution for 3.5 hours. The cells are subsequently washed, the dye is extracted in each well and the absorbance is read using a spectrophotometer.

For sampling, 1 mL of DMEM (without phenol red indicator) with neutral red (OD=0.110) was added to the cells for 3.5 hours (37° C., 10% $CO_2$). After incubation, the medium was removed, two washes of PBS were realized and 1 mL of extraction solution (absolute ethanol 49%, ultrapure water 49%, glacial acetic acid 2%) was added. Plates were placed 15 minutes on rotary shaker in the dark before reading OD at 540 nm.

Calculations

The $OD_{540\ nm}$ average value of positive control was considered as 100% of viability.

The percentage of viability for each assay was calculated as follow:

% viability assay=($OD_{540\ nm}$ of tested solution–blank)*100/($OD_{540\ nm}$ of positive control–blank).

The cell viability percentages calculated from stressed cultures added with tested compounds were compared with stress-control culture at different times.

LDH Bioassay

Revelation of Effect of Molecules by LDH Bioassay

The cell lysis was determined using a colorimetric assay that quantitatively measures lactate deshydrogenase (LDH), a stable cytosolic enzyme, which is released upon cell lysis.

After 48 hours of exposure of bacterial stress, a LDH bioassay was performed. The kit "CytoTox 96® Non-Radioactive Cytotoxicity Assay" (Promega) and its protocol was used to determine the concentration of LDH containing in the different well.

The OD values at 490 nm represented the level of cell lysis. The average of $OD_{490\ nm}$ values of each tested compound solution were compared together.

Results a) Starvation

The results obtained with different glycopeptides are gathered in tables 2 to 5 depending on compounds or cells which have been tested.

Human neonatal skin fibroblasts

TABLE 2 preservative effect of compound 17, compound 19 and compound 20 on human fibroblasts culture for 7 days after serum deprivation

| Culture conditions | Percentage of viability for 7 days | | | | | |
|---|---|---|---|---|---|---|
| | D 1 | | D 4 | | D 7 | |
| Positive control (no stress) | 100 | ±2.82 | 100 | ±6.14 | 100 | ±5.33 |
| Stress Control (starvation medium) | 77 | ±0.21 | 44 | ±0.77 | 8 | ±0.56 |
| Stress + compound 17 at 10 mg/mL | 71 | ±0.53 | 61 | ±3.35 | 55 | ±1.60 |
| Stress + compound 17 at 5 mg/mL | 75 | ±1.40 | 54 | ±2.77 | 45 | ±2.16 |
| Stress + compound 20 at 5 mg/mL | 87 | ±0.81 | 63 | ±1.21 | 50 | ±2.78 |
| Stress + compound 19 at 5 mg/mL | 73 | ±1.40 | 57 | ±2.05 | 50 | ±3.40 |

As seen in table 2, the cells in starvation medium (stress control) showed a clear decrease of their viability from D1 (77%) to D7 (8%). Likewise the results show that the viability of stressed cells treated with compound 17, compound 19 or compound 20 at 5 mg/ml, decreased slightly between D1 (73 to 87%) and D7 (45 to 50%) but remained clearly higher than the stress control at D7.

Thus compounds 17, 19 or 20 showed a significant preservative/protective effect on skin fibroblasts since cells have been maintained in a healthy state under unfavorable conditions for growth.

TABLE 3 preservative effect of compound 44, compound 24, compound 26, compound 28, compound 30, compound 34 and compound 38 on human skin fibroblast culture for 8 days after serum deprivation

| Culture conditions | Percentage of viability for 8 days | |
|---|---|---|
| | D4 | D8 |
| Positive control (no stress)* | 100 ± 2.70 | 100 ± 3.72 |
| Stress Control (starvation medium) | 83 ± 1.21 | 34 ± 4.67 |
| Stress + compound 44 at 10 mg/mL | 111 ± 2.9 | 102 ± 1.3 |
| Stress + compound 24 at 10 mg/mL | 99 ± 3.35 | 95 ± 1.60 |
| Stress + compound 26 at 10 mg/mL | 89 ± 1.21 | 64 ± 2.78 |
| Stress + compound 28 at 10 mg/mL | 109 ± 2.05 | 108 ± 3.40 |
| Stress + compound 30 at 10 mg/mL | 92 ± 1.2 | 74 ± 0.5 |
| Stress + compound 34 at 10 mg/mL | 103 ± 1 | 103 ± 2 |
| Stress + compound 38 at 10 mg/mL | 101 ± 3 | 88 ± 3 |

(*in this assay only the positive control was prepared with culture medium supplemented with 5% of FBS instead of 10%)

As seen in table 3, the cells in starvation medium (stress control) showed a clear decrease of their viability for 8 days (34%). The viability of skin fibroblasts cultured in starvation medium and added with compounds 44, 24, 26, 28, 30, 34 and 38 at 10 mg/ml, remained clearly higher than that of the stress control at D8 (64 to 108% vs 34%).

These results showed a significant preservative/protective effect of compounds 44, 24, 26, 28, 30, 34 and 38 on skin fibroblasts maintaining cells in a healthy state under unfavorable conditions for growth.

TABLE 4 preservative effect of compound 17 and compound 22 on human fibroblast culture for 4 days after serum deprivation

| Culture conditions | Percentage of viability for 4 days D4 |
|---|---|
| Positive control (no stress) | 100 ± 2.9 |
| Stress Control (serum free medium) | 57 ± 1 |
| Stress + compound 17 at 10 mg/mL | 116 ± 6.4 |
| Stress + compound 22 at 10 mg/mL | 93 ± 2.2 |

As seen in table 4, the cells in starvation medium (stress control) showed a clear decrease of their viability for 4 days (57%) whereas the cell viability of stressed cells treated with compound compound 17 or compound 22 at 10 mg/ml remains very high (116% and 93% respectively). These results showed a significant preservative/protective effect of compounds 17 and 22.

Human nasal epithelial cells

TABLE 5 preservative effect of compound 19 on human nasal epithelial cell culture for 6 days after serum deprivation

| Culture conditions | Percentage of viability for 6 days | |
|---|---|---|
| | D4 | D6 |
| Positive control (no stress) | 100 ± 33.77 | 100 ± 17 |
| Stress Control (serum free medium) | 27 ± 6.40 | 7 ± 1.87 |
| Stress + compound 19 at 10 mg/mL | 52 ± 4.64 | 26 ± 4.64 |

As seen in the table above, the cells in starvation medium (stress control) showed a clear decrease of their viability at D4 (27%) to D6 (7%). Likewise the results show that the viability of stressed cells added with compound 19 at 10 mg/ml decreased for 6 days but remained higher than the stress control (26% vs 7% at D6). Thus compound 19 showed a preservative/protective effect on human nasal epithelial cells.

b) Oxidative Stress

The results obtained with compound 19 at different concentration are gathered in table below.

TABLE 6 human neonatal skin fibroblasts viability in culture for 24 h after adding $H_2O_2$

| Culture conditions | Percentage of viability following oxidative stress | |
|---|---|---|
| | 1 h | 24 h |
| Positive control (no stress) | 100 7.21 | 100 ± 1.3 |
| Stress Control (100 µM $H_2O_2$) | 89 ± 4.7 | 74 ± 6.4 |
| Stress + compound 19 at 5 mg/mL | 89 ± 2.7 | 109 ± 2.2 |
| Stress + compound 19 at 10 mg/mL | 99 ± 0.5 | 120 ± 2.1 |
| Stress + compound 19 at 15 mg/mL | 110 ± 2.0 | 127 ± 5.8 |

The results in table 6 show that the viability of stressed cells added with compound 19 at 5 mg/ml, 10 mg/ml or 15 mg/ml increased for 24 h and remained highly higher than that of the stress control (109 to 127% respectively vs 74%, at 24 h after the oxidative stress). Thus, compound 19 has shown a preservative/protective effect against oxidative stress which is dose dependant.

Moreover in culture added with compound 19, the cell viability increased in time that showed a growth/regenerative effect on stressed cells.

c) UV Stress

The results obtained with compound 17 and compound 19 at different concentrations are gathered in table 7 below.

TABLE 7 human neonatal skin fibroblasts viability
in culture for 24 h after UV irradiation

| Culture conditions | Percentage of viability following UV stress (11 J/cm$^2$) | | | | | |
|---|---|---|---|---|---|---|
| | 1 h | | 3 h | | 24 h | |
| Positive control (no stress) | 100 | ±7.21 | 100 | ±7.21 | 100 | ±1.29 |
| Stress Control (UV irradiation) | 10 | ±3.1 | 6 | ±1.61 | 12 | ±5.3 |
| irradiation + compound 17 (5 mg/mL) | 55 | ±4.0 | 63 | ±4.2 | 82 | ±7.4 |
| irradiation + compound 17 (10 mg/mL) | 53 | ±2.4 | 46 | ±3.2 | 94 | ±9.0 |
| irradiation + compound 17 (15 mg/mL) | 50 | ±0.5 | 50 | ±1.0 | 84 | ±9.5 |
| irradiation + compound 19 (5 mg/mL) | 53 | ±6.6 | 71 | ±5.9 | 89 | ±14.0 |
| irradiation + compound 19 (10 mg/mL) | 70 | ±4.0 | 80 | ±3.9 | 116 | ±3.9 |
| irradiation + compound 19 (15 mg/mL) | 67 | ±1.7 | 80 | ±1.8 | 112 | ±2.7 |

As seen in the table above, the irradiated cells in the stress control assay showed a clear decrease of their viability from 1 h after the UV irradiation (viability 10%), whereas the viability of stressed cells added with compounds 17 or 19 at 5 mg/ml increased for 24 h and remained highly higher than that of the stress control (82% and 89% respectively vs 12% at 24 h after the UV stress).

Thus, compounds 17 and 19 showed a preservative/protective effect against UV stress.

Moreover in culture added with compound 17 or 19, the cell viability increased in time that showed a growth or regenerative effect on stressed cells.

d) Bacterial Stress

The values of OD$_{490\ nm}$ obtained with 3 solutions of compound 17 at 5, 10 or 15 mg/mL were compared in the table 8 below.

TABLE 8 human neonatal skin fibroblasts lysis at 48 h following bacterial stress

| Culture conditions | Lysis following bacterial stress at 48 h (OD$_{490\ nm}$) |
|---|---|
| 17 (5 mg/mL) | 0.333 ± 0.003 |
| 17 (10 mg/mL) | 0.293 ± 0.002 |
| 17 (15 mg/mL) | 0.270 ± 0.005 |

The OD$_{490\ nm}$ which represented the cell lysis under bacterial stress at 48 h, decreased when the quantity of compound 17 raised from 5 mg/ml to 15 mg/ml. Compound 17 has thus shown a protective effect on cells against bacterial stress.

III—Comparative Study

Comparative Stability Studies Between Compound 17 and Compound X (Referred as Compound 15 in WO 2006/059227)

The aim of this study is to demonstrate the tremendous improvement of the stability towards basic conditions of compound 17 compared to compound X. For that, the following sets of experiments have been carried out.

In a first set of experiments (experiments 1 to 7 in table 9), X (10 mg, 1.72 10$^{-2}$ mmol) was reacted with 2 to 8 equivalents of NaOD in a total volume of 355 µL of deuterium oxide ([X]=4.8 10$^{-2}$ mmol·mL$^{-1}$) during 2 h 30 before being acidified with 1M DCl in D$_2$O. To be sure that all compounds in solution are in their acidic form, the equivalents of DCl are adjusted to 3 more equivalents of DCl than the amount required to neutralize the solution (n$_{DCl}$=n$_{NaOD}$+3). The volume was adjusted to 544 µL with deuterium oxide.

In a second set of experiments (experiments 8 to 14 in table 9), 17 (10 mg, 1.66 10$^{-2}$ mmol) was reacted with 2 to 8 equivalents of NaOD in a total volume of 343 µL of deuterium oxide ([17]=4.8 10$^{-2}$ mmol·mL$^{-1}$) during 2 h 30 before being acidified with 1M DCl in D$_2$O. To be sure that all compounds in solution are in their acidic form, the equivalents of DCl are adjusted to 3 more equivalents of DCl than the amount required to neutralize the solution (n$_{DCl}$=n$_{NaOD}$+3). The volume was adjusted to 526 µL with deuterium oxide.

TABLE 9

| | Compound X | | | | | | |
|---|---|---|---|---|---|---|---|
| Experiment no | 1 | 2 | 3 | 4 | 5 | 6 | 7 |
| neq$_{NaOD\ 1M}$ | 2 | 3 | 4 | 5 | 6 | 7 | 8 |
| V$_{1D2O}$(µL) | 320 | 303 | 286 | 269 | 251 | 234 | 217 |
| V$_{NaOD\ 1M}$(µL) | 34 | 52 | 69 | 86 | 103 | 120 | 138 |
| V$_{reaction}$(µL) | 355 | 355 | 355 | 355 | 355 | 355 | 355 |
| V$_{DCl\ 1M}$(µL) | 86 | 103 | 120 | 138 | 155 | 172 | 189 |
| V$_{2D2O}$(µL) | 103 | 86 | 69 | 52 | 35 | 17 | 0 |
| V$_{total}$ | 544 | 544 | 544 | 544 | 544 | 544 | 544 |
| | Compound 17 | | | | | | |
| Experiment no | 8 | 9 | 10 | 11 | 12 | 13 | 14 |
| neq$_{NaOD\ 1M}$ | 2 | 3 | 4 | 5 | 6 | 7 | 8 |
| V$_{1D2O}$(µL) | 310 | 294 | 277 | 260 | 244 | 227 | 211 |
| V$_{NaOD\ 1M}$(µL) | 33 | 50 | 66 | 83 | 100 | 116 | 133 |
| V$_{reaction}$(µL) | 343 | 343 | 343 | 343 | 343 | 343 | 343 |
| V$_{DCl\ 1M}$(µL) | 83 | 100 | 116 | 133 | 149 | 166 | 183 |
| V$_{2D2O}$(µL) | 100 | 83 | 66 | 50 | 33 | 17 | 0 |
| V$_{total}$ | 526 | 526 | 526 | 526 | 526 | 526 | 526 |

$^1$H NMR analyses were performed on each experiment. It is why experiments were realized in deuterium oxide and using 1M NaOD in D$_2$O as base and 1M DCl in D$_2$O as acid. These $^1$H NMR analyses allowed showing the absence of degradation of compound 17 and the degradation of compound X as presented on scheme 1 below:

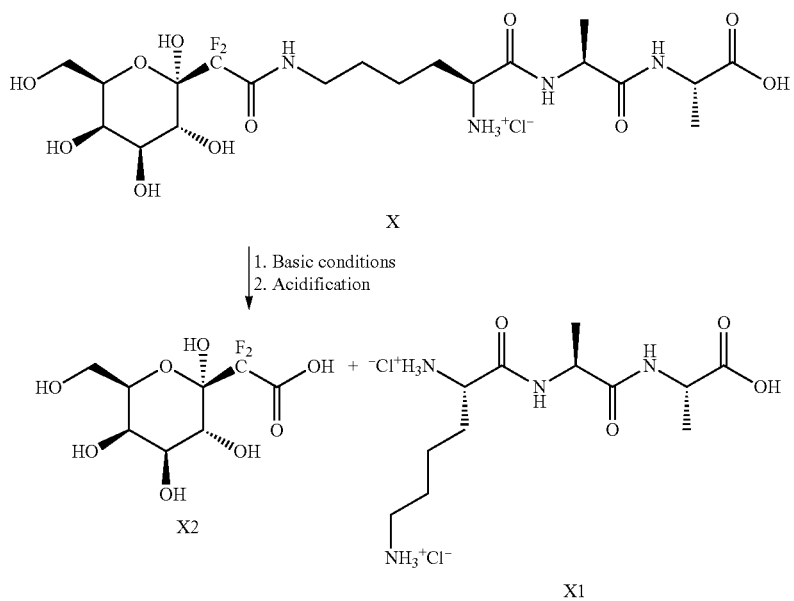

X

1. Basic conditions
2. Acidification

X2  +  X1

$^1$H NMR allows indeed the determination of the amount of compound X1 formed, by comparison between the integration corresponding to the methylene group of the lysine side chain connected to the nitrogen atom in X (CH$_2$NGP) (3.3 ppm) and the integration of the same methylene group in X1 (CH$_2$Lys hydrolyzed) (3.0 ppm). Results are depicted in table 10 below.

TABLE 10

| Experiment | | neq$_{NaOD}$ | integration CH$_2$NGP | integration CH$_2$Lys hydrolysis | % hydrolyzed |
|---|---|---|---|---|---|
| Compound X | Control | 0 | 2 | 0.01 | 0.5 |
| | 1 | 2 | 2 | 0.04 | 2.0 |
| | 2 | 3 | 2 | 0.10 | 4.8 |
| | 3 | 4 | 2 | 0.30 | 13.0 |
| | 4 | 5 | 2 | 0.38 | 16.0 |
| | 5 | 6 | 2 | 0.47 | 19.0 |
| | 6 | 7 | 2 | 0.52 | 20.6 |
| | 7 | 8 | 2 | 0.57 | 22.2 |
| Compound 17 | Control | 0 | 2 | 0 | 0 |
| | 8 | 2 | 2 | 0 | 0 |
| | 9 | 3 | 2 | 0 | 0 |
| | 10 | 4 | 2 | 0 | 0 |
| | 11 | 5 | 2 | 0 | 0 |
| | 12 | 6 | 2 | 0 | 0 |
| | 13 | 7 | 2 | 0 | 0 |
| | 14 | 8 | 2 | 0 | 0 |

Figure 2:
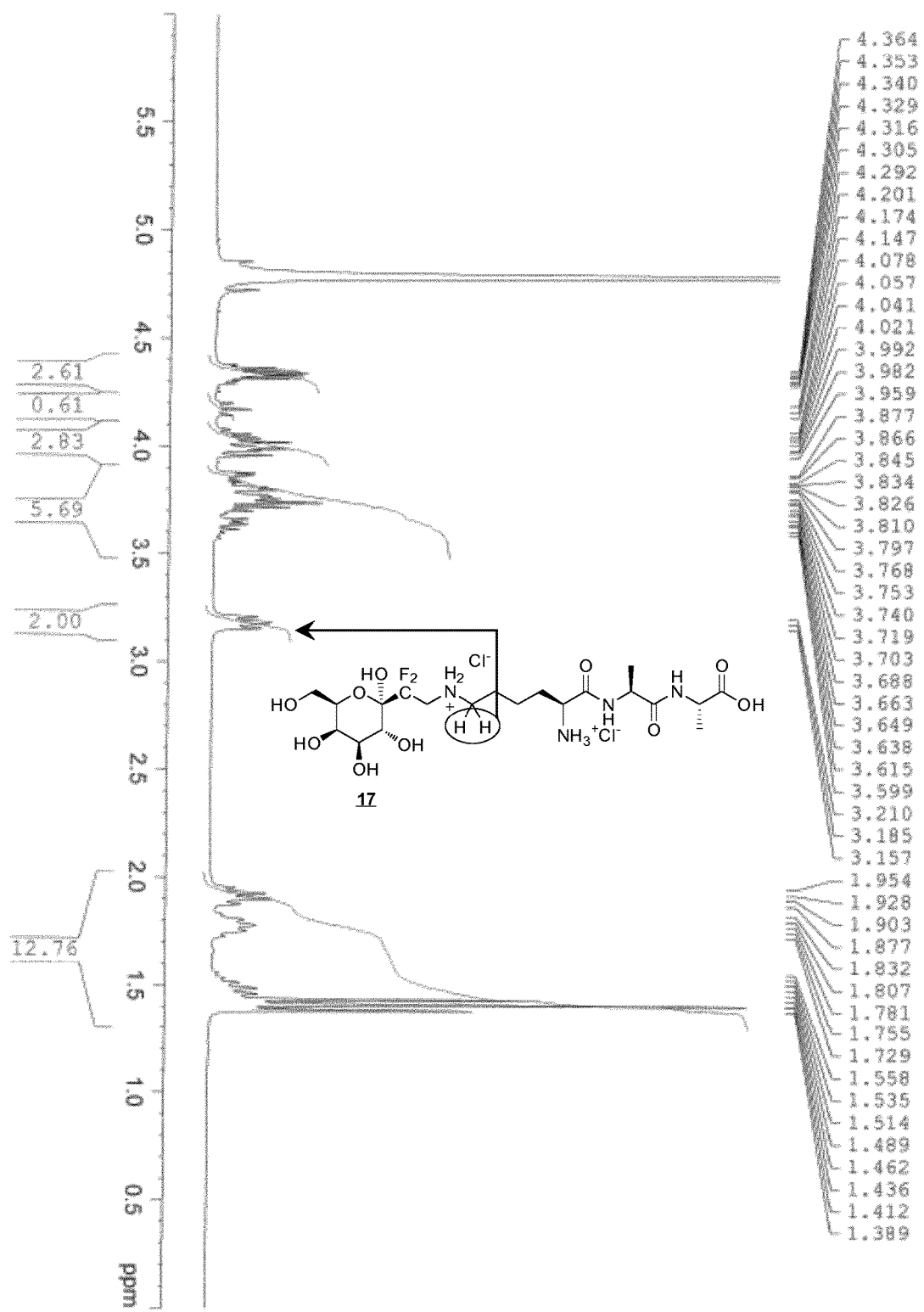
Figure 3:
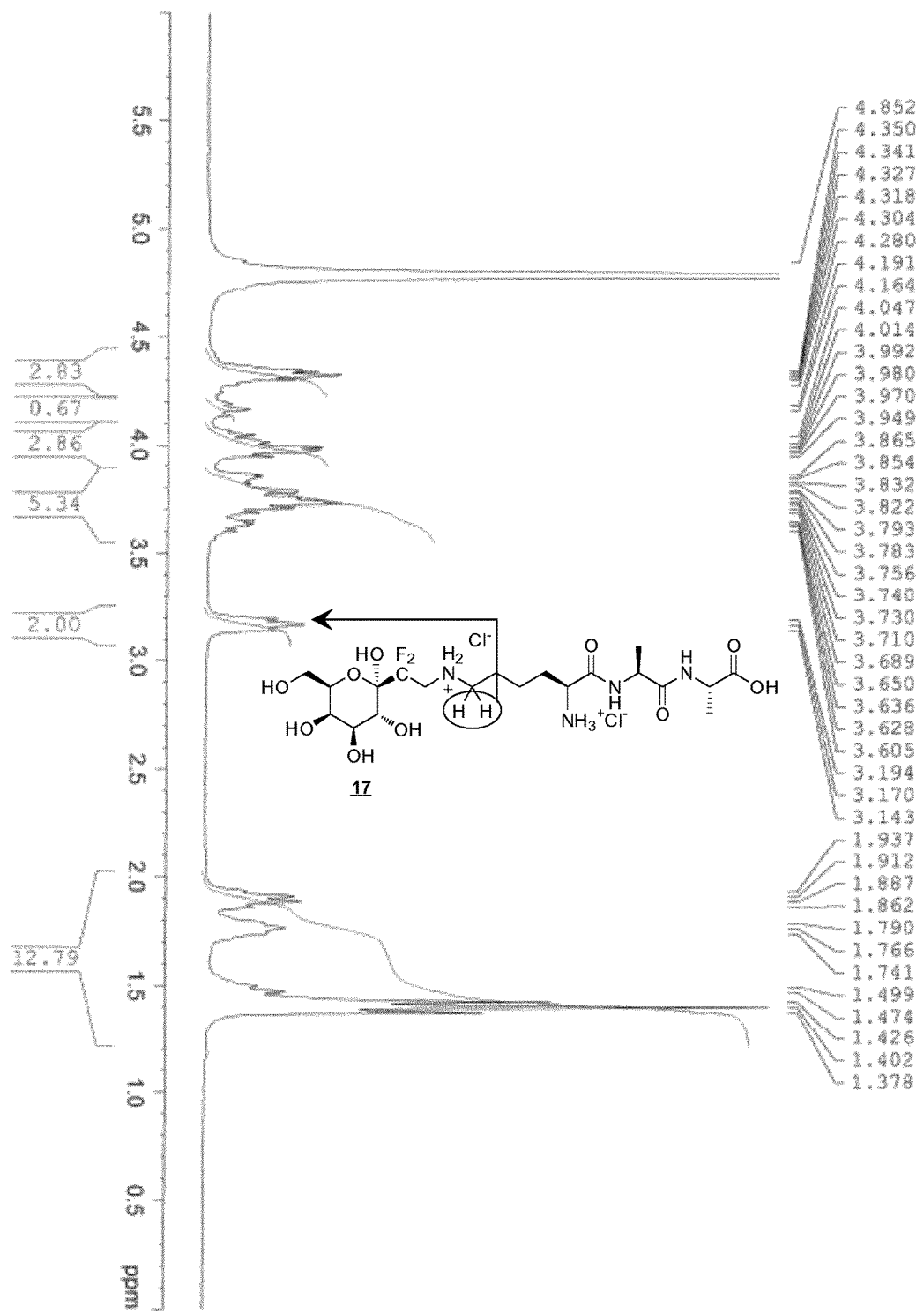

Regarding these results, it appears that compound X is sensitive to basic medium which is not the case for compound 17. Indeed, the initial $^1$H NMR spectrum of compound 17 (control—FIG. 2) and the $^1$H NMR spectra of experiments 8 to 14 ($^1$H NMR spectrum of experiment 14 is presented on FIG. 3) are very similar while comparison of the initial $^1$H NMR spectrum of compound X (control—FIG. 4) and the $^1$H NMR and spectra of experiments 1 to 7 ($^1$H NMR spectrum of experiment 7 is presented on FIG. 5) show the progressive hydrolysis of compound X by the progressive formation of compound X1 (and thus compound X2), with up to 22% hydrolysis in experiment 7 (8 equivalents of NaOD for 2 h 30).

To confirm the structure of compounds X1 and X2, resulting from hydrolysis of X, the following experiment was realized, in which X (10 mg, 1.72 10$^{-2}$ mmol) was reacted with 8 equivalents of NaOD in a total volume of 355 µL of deuterium oxide ([X]=4.8 10$^{-2}$ mmol·mL$^{-1}$) during 3 days before being acidified with 1M DCl in D$_2$O. In these conditions, almost the totality of compound X is hydrolyzed, the percentage of hydrolysis of compound X being 85% as determined by $^1$H NMR as evidence in table 11.

TABLE 11

| Experiment | neq$_{NaOD}$ | integration CH$_2$NGP | integration CH$_2$Lys hydrolyzed | % hydrolysis |
|---|---|---|---|---|
| A | 0 | 2 | 0.01 | 0.5 |
| B | 8 | 2 | 11.13 | 85 |

Figure 4:
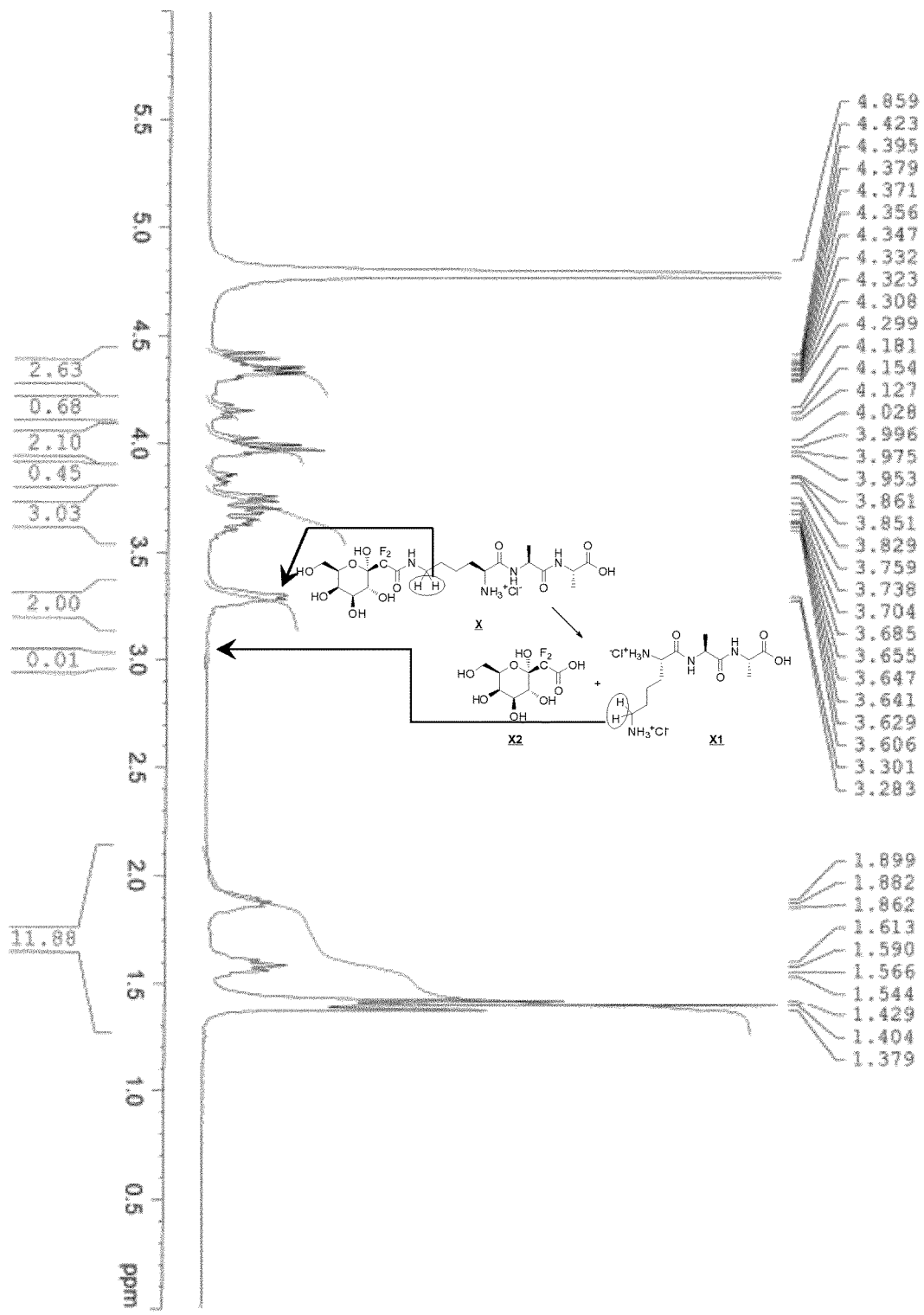
FIGS. 4 and 5 represent respectively the $^1$H RMN spectrum of a solution of compound X after addition of 0 or 8 equivalents of NaOD and 2 h 30 of reaction.
Figure 5:
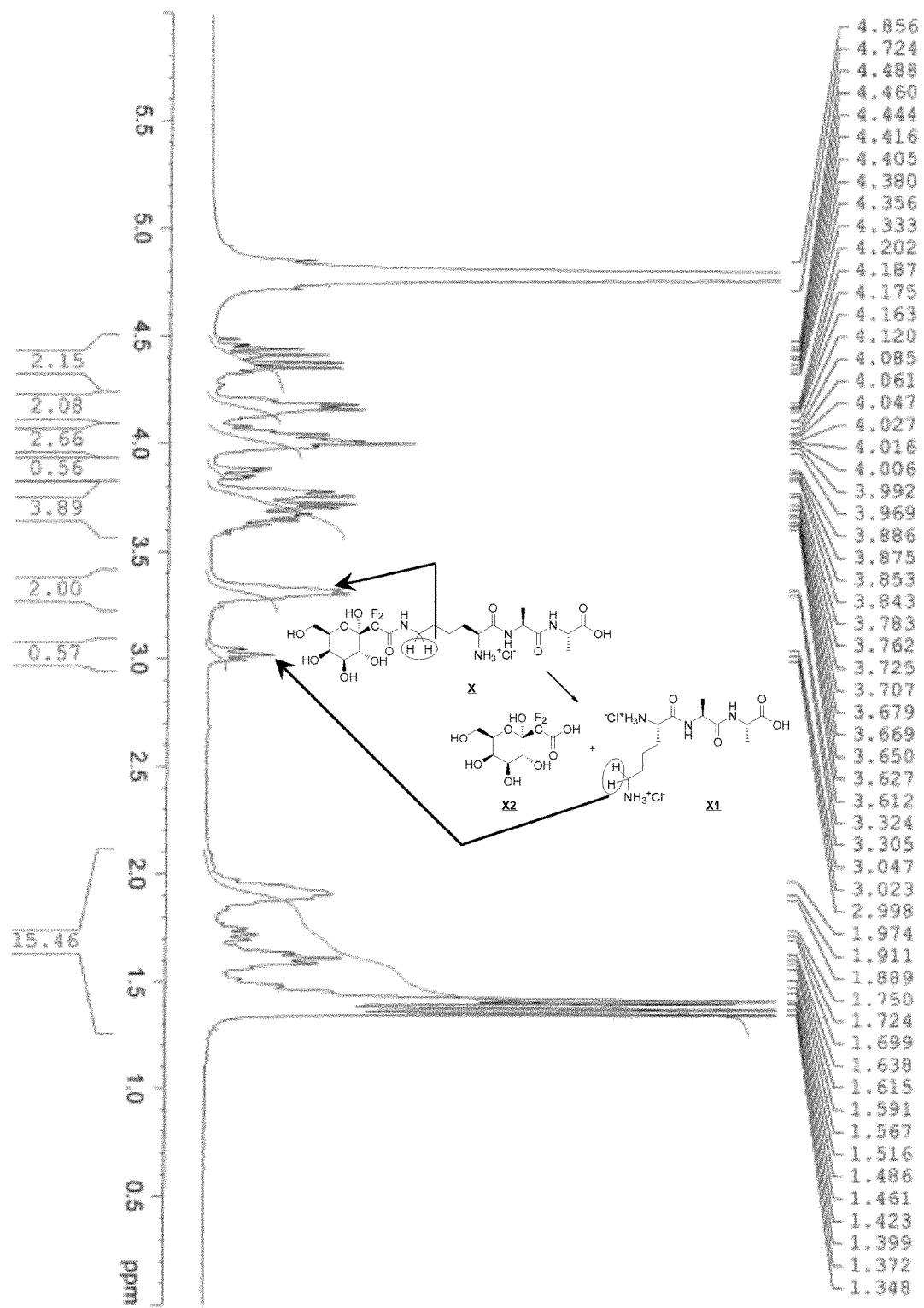
Figure 6:
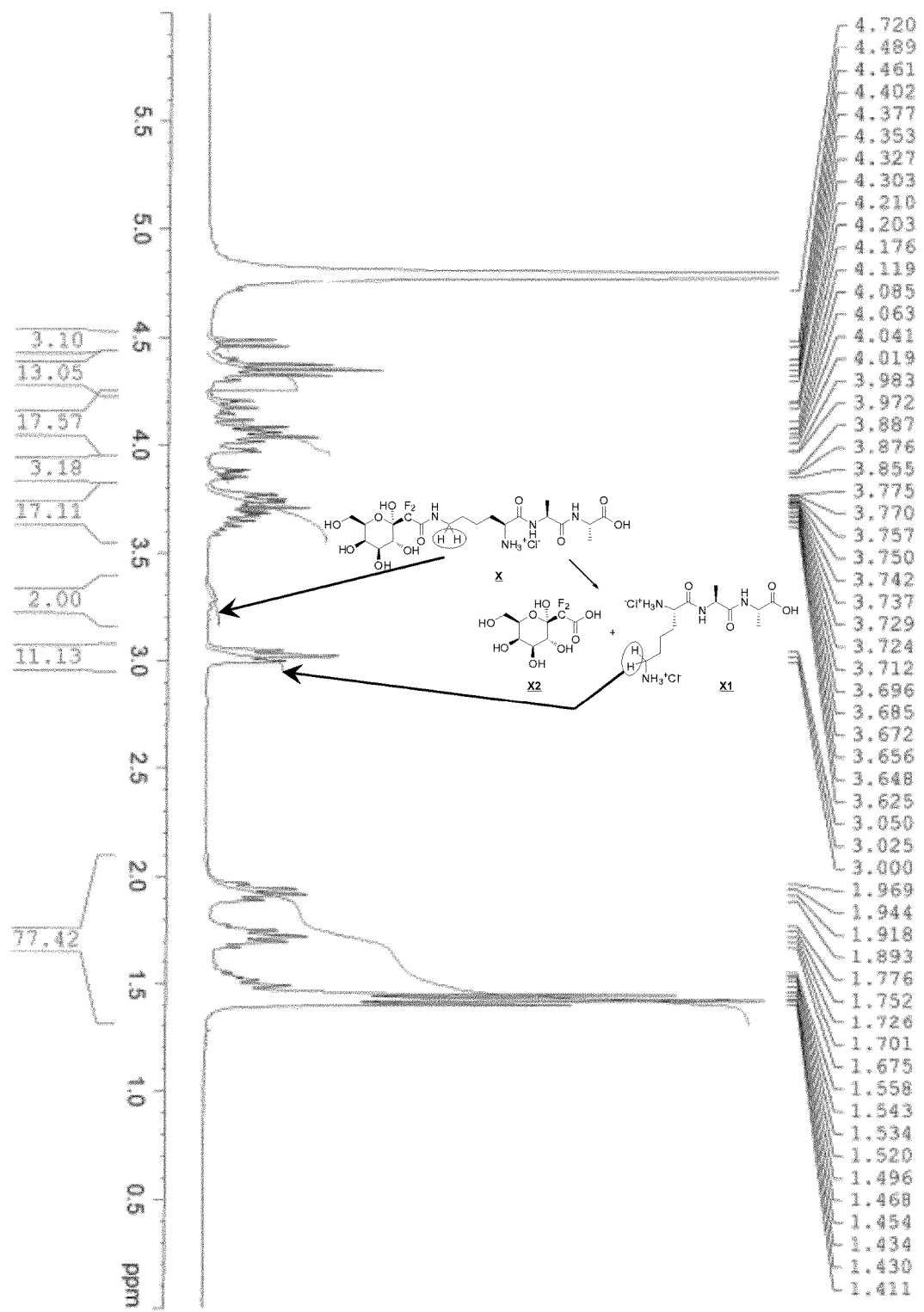
FIG. 6 represents the $^1$H RMN spectrum of a solution of compound X after addition of 8 equivalents of NaOD and 3 days of reaction.

The $^1$H NMR spectra of the solution of experiments A and B are presented respectively on FIG. 4 and FIG. 6.

Figure 7:
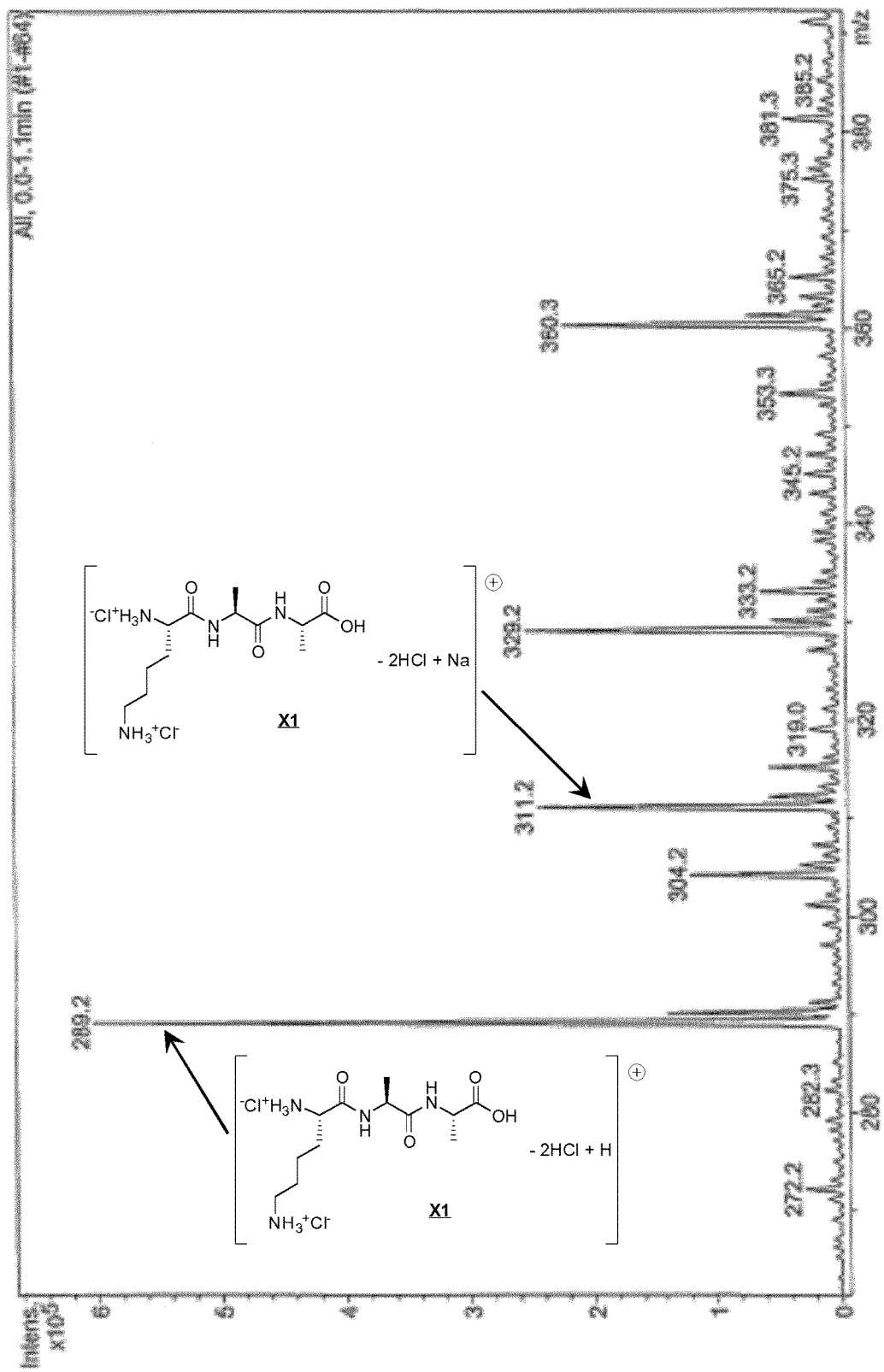
FIGS. 7 and 8 represent the mass spectra of a solution of compound X after addition of 8 equivalents of NaOD and 3 days of reaction, respectively in ESI$^+$ and ESI$^-$ mode.
Figure 8:
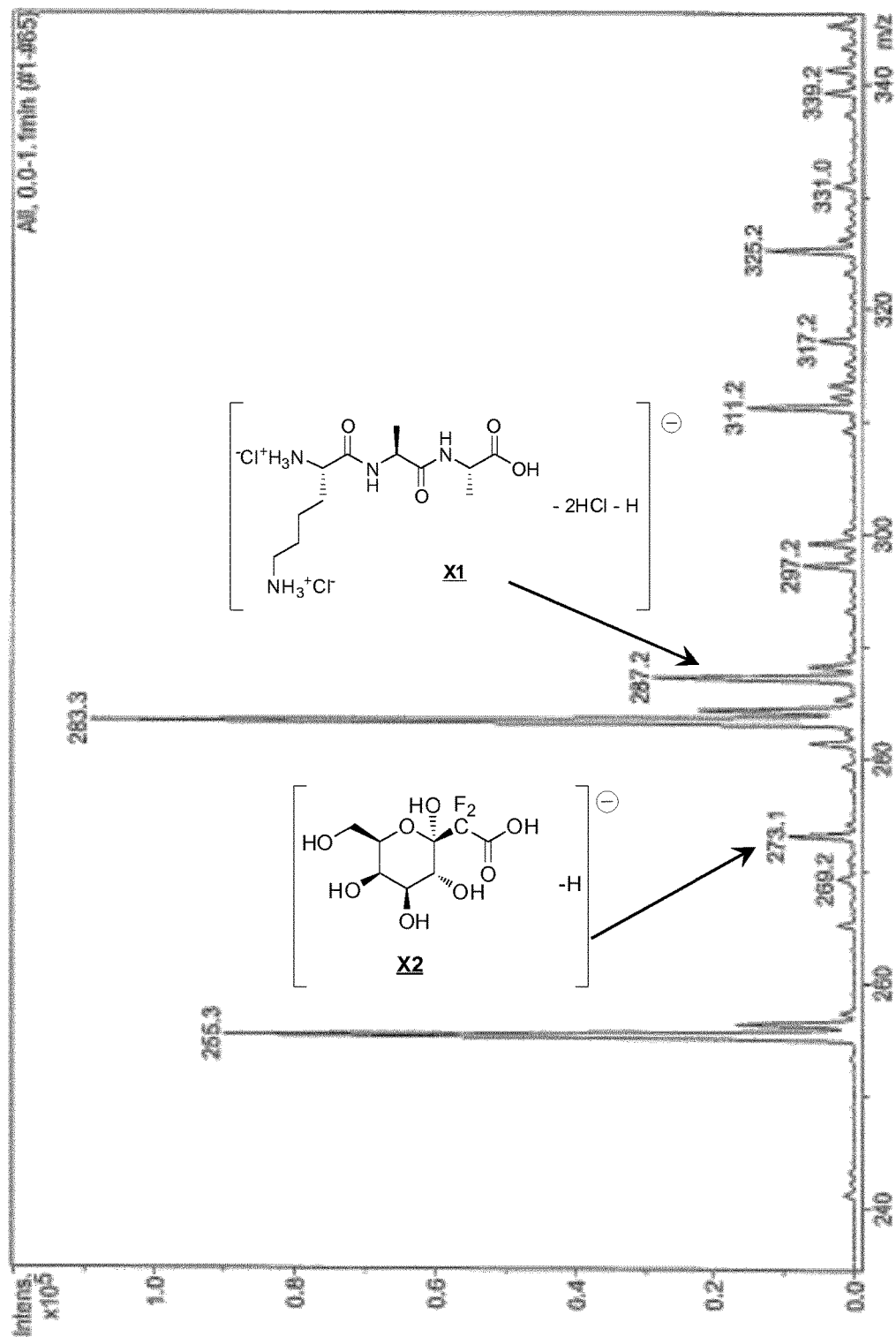

The solution of experiment B was analyzed by mass spectrometry (ESI$^+$ and ESI$^-$). In ESI$^+$ two ion adducts with mass of 289.2 and 311.2 were detected, corresponding to [X1-2HCl+H]$^+$ and [X1-2HCl+Na]$^+$ respectively (mass spectrum presented on FIG. 7). In ESI$^-$ two ion adducts with mass of 273.1 and 287.2 were detected, corresponding to [X2-H]$^-$ and [X1-2HCl -H]$^-$ respectively (mass spectrum presented on FIG. 8).

The invention claimed is:
1. A compound of formula (I):

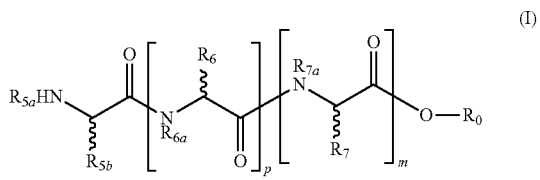

(I)

or a salt thereof, a solvate, a tautomer, a stereoisomer or a mixture of stereoisomers in any proportion, wherein:
m is 0 or 1,
p is 0 or 1,
$R_0$ is a hydrogen atom, a O-protecting group or a ($C_1$-$C_6$)alkyl, ($C_2$-$C_6$)alkenyl, ($C_2$-$C_6$)alkynyl, ($C_3$-$C_7$)cycloalkyl, 5- to 7-membered heterocycloalkyl, aryl, heteroaryl, aryl-($C_1$-$C_6$)alkyl, heteroaryl-($C_1$-$C_6$)alkyl, ($C_1$-$C_6$)-alkyl-aryl or ($C_1$-$C_6$)-alkyl-heteroaryl group, this group being possibly substituted with one or more groups selected from a halogen atom, ($C_1$-$C_6$)alkoxy, OH, COOH and CHO,
$R_{5a}$, $R_{6a}$ and $R_{7a}$ are, independently from each other, a hydrogen or a N-protecting group, and
$R_5$, $R_6$ and $R_7$ are, independently from each other, a hydrogen; a ($C_1$-$C_6$)alkyl optionally substituted by a ($C_1$-$C_6$)alkoxy or a ($C_1$-$C_6$)thioalkoxy; an aryl; an aryl-($C_1$-$C_6$)alkyl optionally substituted by a ($C_1$-$C_6$) alkoxy; or a group of the following formula:

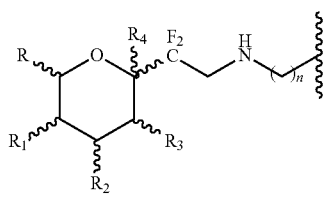

or $R_5$ and $_{5a}$ and/or $R_6$ and $R_{6a}$ and/or $R_7$ and $R_{7a}$ form, with the nitrogen and carbon atoms carrying them, a pyrrolidine cycle

provided that at least one and only one group among $R_5$, $R_6$ and $R_7$ when m=p=1, or at least one and only one group among $R_5$ and $R_6$ when m=0 and p=1, or at least one and only one group among $R_5$ and $R_7$ when m=1 and p=0, or $R_5$ when m=p=0, is a group of formula:

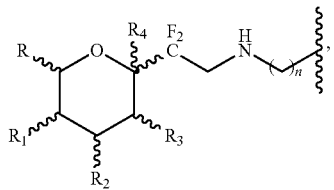

with
n is an integer from 1 to 6,
R is a hydrogen or fluorine atom or a $CH_3$, $CH_2F$, $CH_2OSiR^{a1}R^{b1}R^{c1}$, $CH_2OR_8$, $CH_2OC(O)R_9$, $CH_2OCO_2R_{10}$, $CH_2OC(O)NR_{11}R_{12}$, $CH_2OP(O)(OR_{13})_2$ or $CH_2OSO_3R_{14}$ group,
$R_1$ and $R_2$ are, independently from one another, a fluorine atom or an $OSiR^{a2}R^{b2}R^{c2}$, $OR_{15}$, $OC(O)R_{16}$, $OCO_2R_{17}$, $OC(O)NR_{18}R_{19}$, $OP(O)(OR_{20})_2$ or $OSO_3R_{21}$ group,
$R_3$ is a fluorine atom or an $OSiR^{a3}R^{b3}R^{c3}$, $OR_{22}$, $OC(O)R_{23}$, $OCO_2R_{24}$, $OCONR_{25}R_{26}$, $OP(O)(OR_{27})_2$, $OSO_3R_{28}$, $N_3$, phthalimidyl, $NR_{29}R_{30}$, $NR_{31}C(O)R_{32}$,
$NR_{33}C(O)OR_{34}$, $N(C(O)R_{35})C(O)R_{36}$, $N(C(O)R_{37})C(O)OR_{38}$ or $N(C(O)OR_{39})C(O)OR_{40}$ group,
$R_4$ is a hydrogen or halogen atom or an $OSiR^{a4}R^{b4}R^{c4}$, $OR_{41}$, $OC(O)R_{42}$, $OCO_2R_{43}$, $OCONR_{44}R_{45}$, $OP(O)(OR_{46})_2$, or $OSO_3R_{47}$ group,
or R and $R_1$, together with the carbon atoms carrying them, form a cyclic acetal having the following formula:

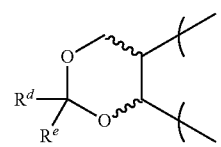

and/or ($R_1$ and $R_2$), ($R_2$ and $R_3$), and/or ($R_3$ and $R_4$), together with the carbon atoms carrying them, form a cyclic acetal having the following formula:

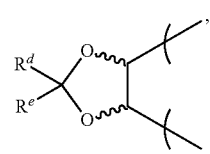

$R_8$, $R_{15}$, $R_{22}$ and $R_{41}$ are, independently from one another, a hydrogen atom, a O-protecting group or a ($C_1$-$C_6$) alkyl, ($C_2$-$C_6$)alkenyl, ($C_2$-$C_6$)alkynyl, ($C_3$-$C_7$)cycloalkyl, 5- to 7-membered heterocycloalkyl, aryl, heteroaryl, aryl-($C_1$-$C_6$)alkyl, heteroaryl-($C_1$-$C_6$)alkyl, ($C_1$-$C_6$)-alkyl-aryl, ($C_1$-$C_6$)-alkyl-heteroaryl, saccharidic or polysaccharidic group, this group being possibly substituted with one or more groups selected from a halogen atom, ($C_1$-$C_6$)alkoxy, OH, COOH and CHO,
$R_9$, $R_{10}$, $R_{16}$, $R_{17}$, $R_{23}$, $R_{24}$, $R_{32}$, $R_{34}$ to $R_{40}$, $R_{42}$ and $R_{43}$ are, independently from one another, a ($C_1$-$C_6$)alkyl, ($C_2$-$C_6$)alkenyl, ($C_2$-$C_6$)alkynyl, ($C_3$-$C_7$)cycloalkyl, 5- to 7-membered heterocycloalkyl, aryl, heteroaryl, aryl-($C_1$-$C_6$)alkyl, heteroaryl-($C_1$-$C_6$)alkyl, ($C_1$-$C_6$)-alkyl-aryl or ($C_1$-$C_6$)-alkyl-heteroaryl group, this group being possibly substituted with one or more groups selected from a halogen atom, ($C_1$-$C_6$)alkoxy, OH, COOH and CHO,
$R_{11}$, $R_{12}$, $R_{18}$, $R_{19}$, $R_{25}$, $R_{26}$, $R_{29}$ to $R_{31}$, $R_{33}$, $R_{44}$ and $R_{45}$ are, independently from one another, a hydrogen atom or a ($C_1$-$C_6$)alkyl, ($C_2$-$C_6$)alkenyl, ($C_2$-$C_6$)alkynyl, aryl, heteroaryl, aryl-($C_1$-$C_6$)alkyl, heteroaryl-($C_1$-$C_6$) alkyl, ($C_1$-$C_6$)-alkyl-aryl or ($C_1$-$C_6$)-alkyl-heteroaryl group, this group being possibly substituted with one or more groups selected from a halogen atom, ($C_1$-$C_6$) alkoxy, OH, COOH and CHO,
$R_{13}$, $R_{14}$, $R_{20}$, $R_{21}$, $R_{27}$, $R_{28}$, $R_{46}$ and $R_{47}$ are, independently from one another, a hydrogen atom or a ($C_1$-$C_6$)alkyl group,
$R^{a1}$ to $R^{a4}$, $R^{b1}$ to $R^{b4}$ and $R^{c1}$ to $R^{c4}$ are, independently from one another, a ($C_1$-$C_6$)alkyl, aryl or aryl-($C_1$-$C_6$) alkyl group, and
$R^d$ and $R^e$ are, independently from one another, a hydrogen atom or a ($C_1$-$C_6$)alkyl group.

2. The compound according to claim 1, wherein it is a compound of the following formula (Ie1), (Ii1), (Im1) or (Iq1):

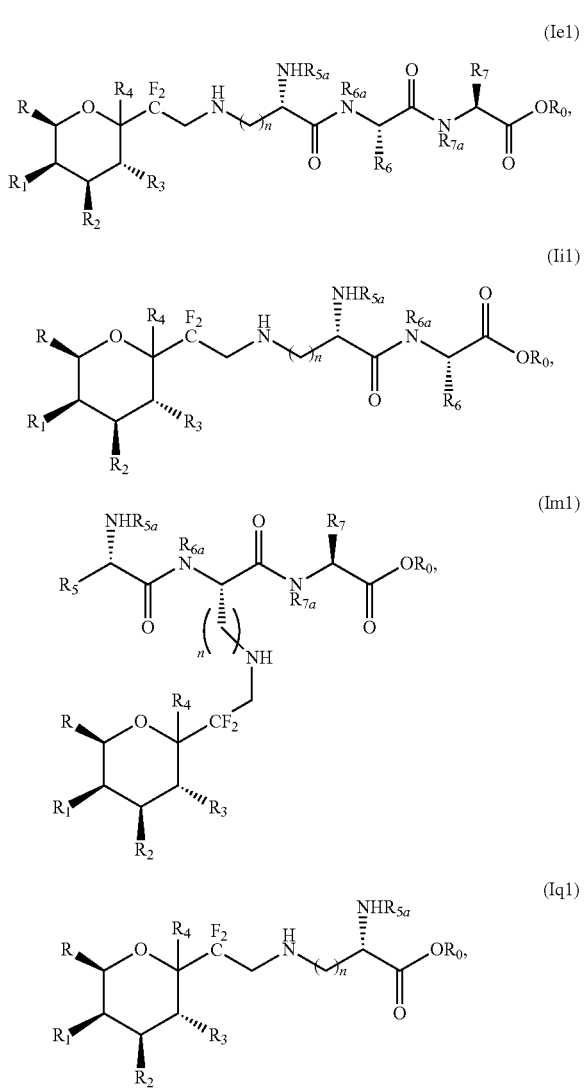

or a salt, a solvate or a tautomer thereof.

3. The compound according to claim 1, wherein $R_5$, $R_6$ and $R_7$ are, independently from each other, a hydrogen atom; a $(C_1\text{-}C_6)$alkyl; an aryl; an aryl-$(C_1\text{-}C_6)$alkyl optionally substituted by a $(C_1\text{-}C_6)$alkoxy group, or a group of the following formula:

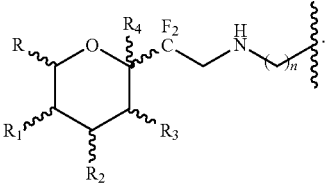

or $R_5$ and $R_{5a}$ and/or $R_6$ and $R_{6a}$ and/or $R_7$ and $R_{7a}$ form, with the nitrogen and carbon atoms carrying them, a pyrrolidine cycle

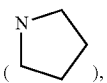

provided that at least one and only one group among $R_5$, $R_6$ and $R_7$ when m=p=1, or at least one and only one group among $R_5$ and $R_6$ when m=0 and p=1, or at least one and only one group among $R_5$ and $R_7$ when m=1 and p=0, or $R_5$ when m=p=0, is a group of formula:

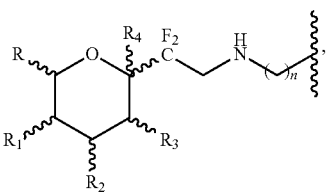

4. The compound according to claim 1, wherein $R_5$, $R_6$ and $R_7$ are, independently from each other, H, $CH_3$, $CH(CH_3)_2$, $CH_2CH(CH_3)_2$, $CH(CH_3)CH_2CH_3$, $CH_2Ph$, $CH_2PhOCH_3$, $CH_2CH_2SCH_3$ or a group of the following formula:

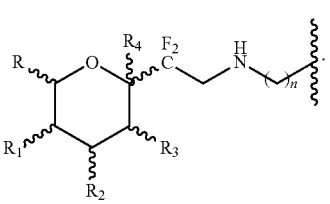

or $R_5$ and $_{5a}$ and/or $R_6$ and $R_{6a}$ and/or $R_7$ and $R_{7a}$ form, with the nitrogen and carbon atoms carrying them, a pyrrolidine cycle

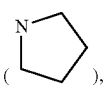

provided that at least one and only one group among $R_5$, $R_6$ and $R_7$ when m=p=1, or at least one and only one group among $R_5$ and $R_6$ when m=0 and p=1, or at least one and only one group among $R_5$ and $R_7$ when m=1 ad p=0, or $R_5$ when m=p=0, is a group of formula:

5. The compound according to claim 1, wherein n has the value 2, 3 or 4.

6. The compound according to claim 1, wherein $R_0$ is a hydrogen atom or a $(C_1\text{-}C_6)$alkyl, aryl or aryl-$(C_1\text{-}C_6)$alkyl group, this group being unsubstituted or substituted with one or more groups selected from a halogen atom, $(C_1-C_6)$ alkoxy, OH, COOH and CHO;

R is a $CH_2OR_8$ group; $R_1$ and $R_2$ are, independently from one another, an $OR_{15}$ group; and $R_3$ is an $OR_{22}$ group, with $R_8$, $R_{15}$ and $R_{22}$ are a hydrogen atom or an O-protecting group; and $R_4$ is a hydrogen atom or an $OR_{41}$ group, wherein $R_{41}$ is a hydrogen atom, a O-protecting group or a $(C_1-C_6)$ alkyl, aryl, aryl-$(C_1-C_6)$alkyl, or $(C_1-C_6)$-alkyl-aryl group, this group being unsubstituted or possibly substituted with one or more groups selected from a halogen atom and $(C_1-C_6)$alkoxy.

7. The compound according to claim 1, wherein $R_0$=H, Et or Bn, R=$CH_2OH$ or $CH_2OBn$, $R_1$=$R_2$=$R_3$=OH or OBn and $R_4$=H, OH, OMe or OBn.

8. The compound according to claim 1, wherein $R_0$=H, R=$CH_2OH$, $R_1$=$R_2$=$R_3$=OH and $R_4$=H or OH.

9. The compound according to claim 1, wherein it is selected from the following compounds:

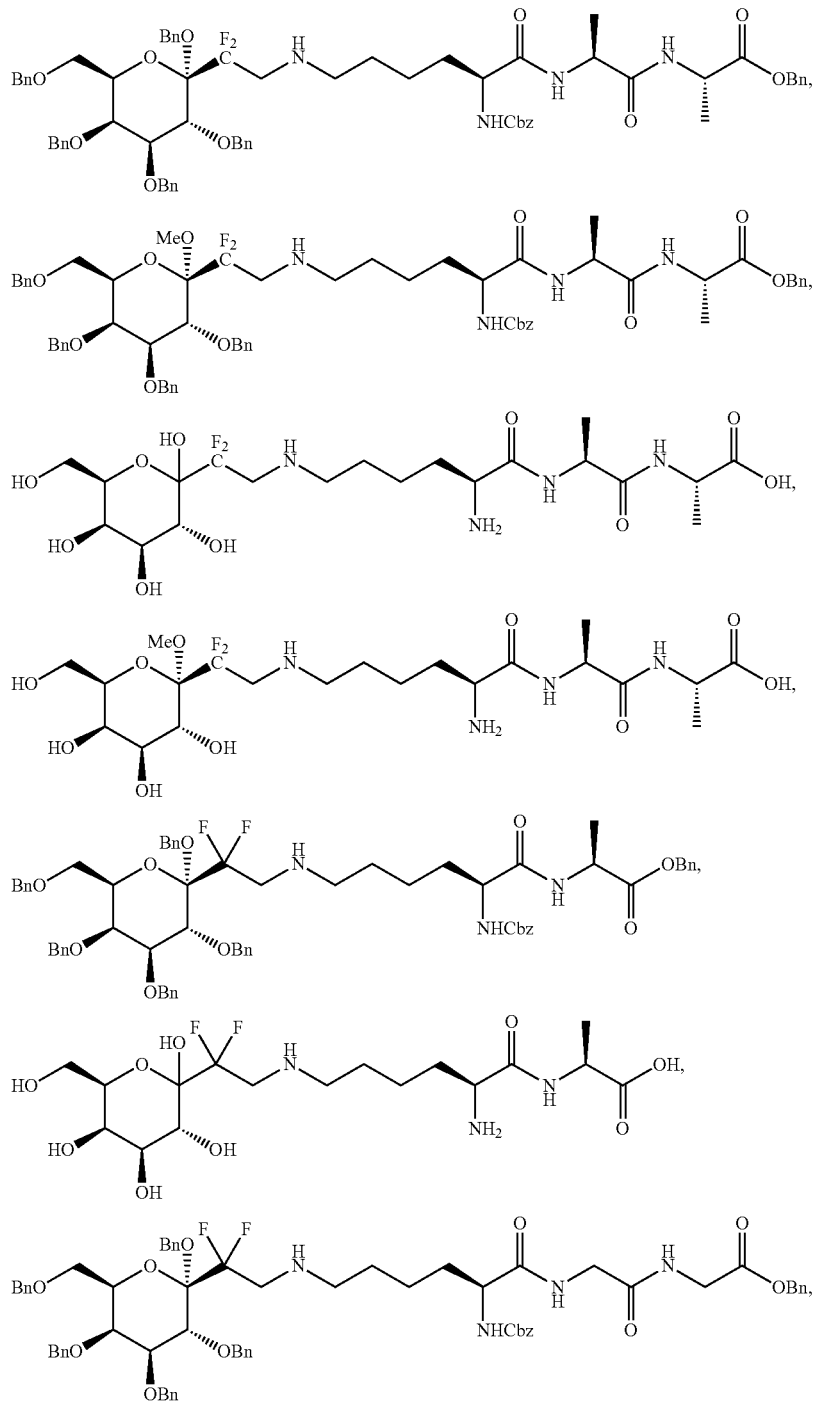

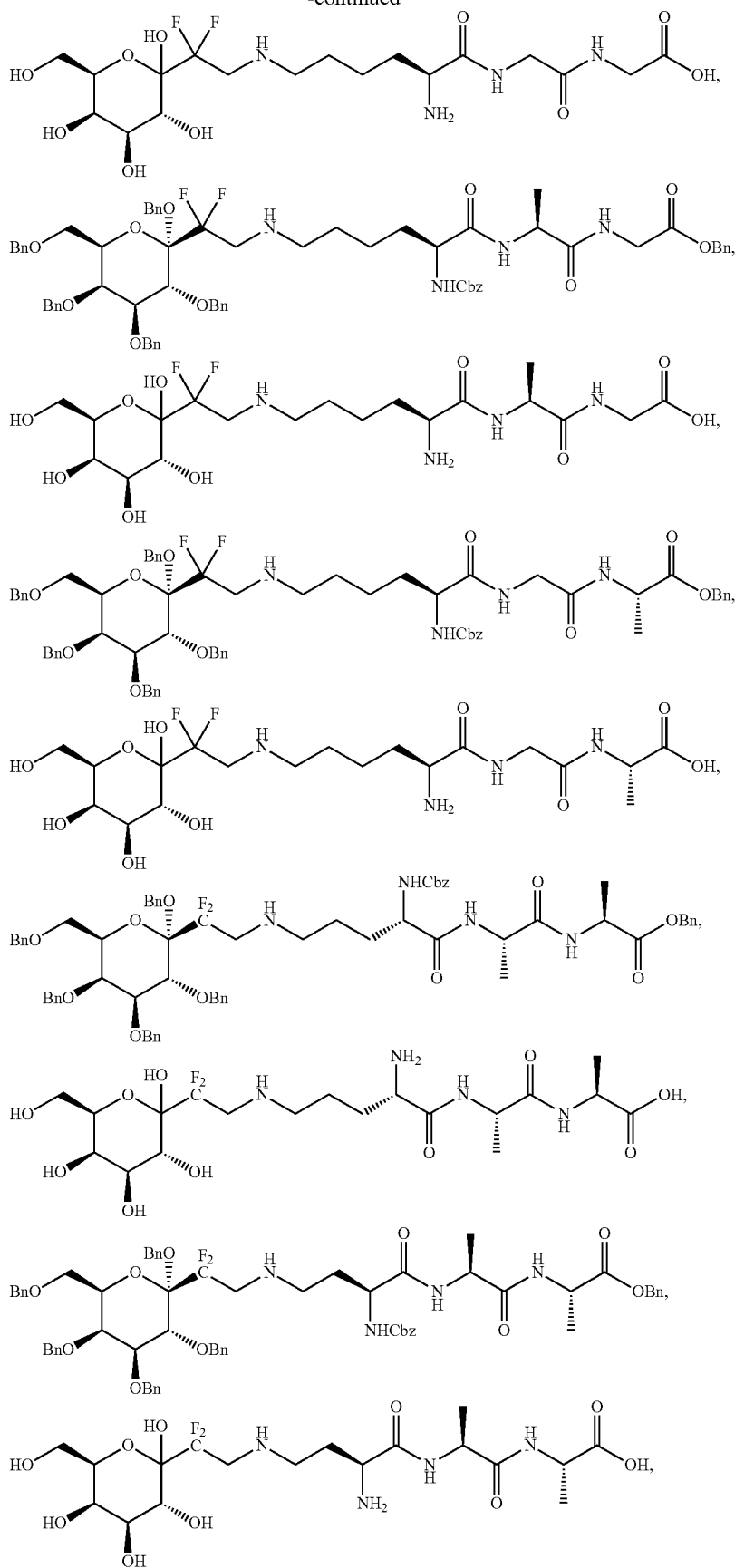

-continued
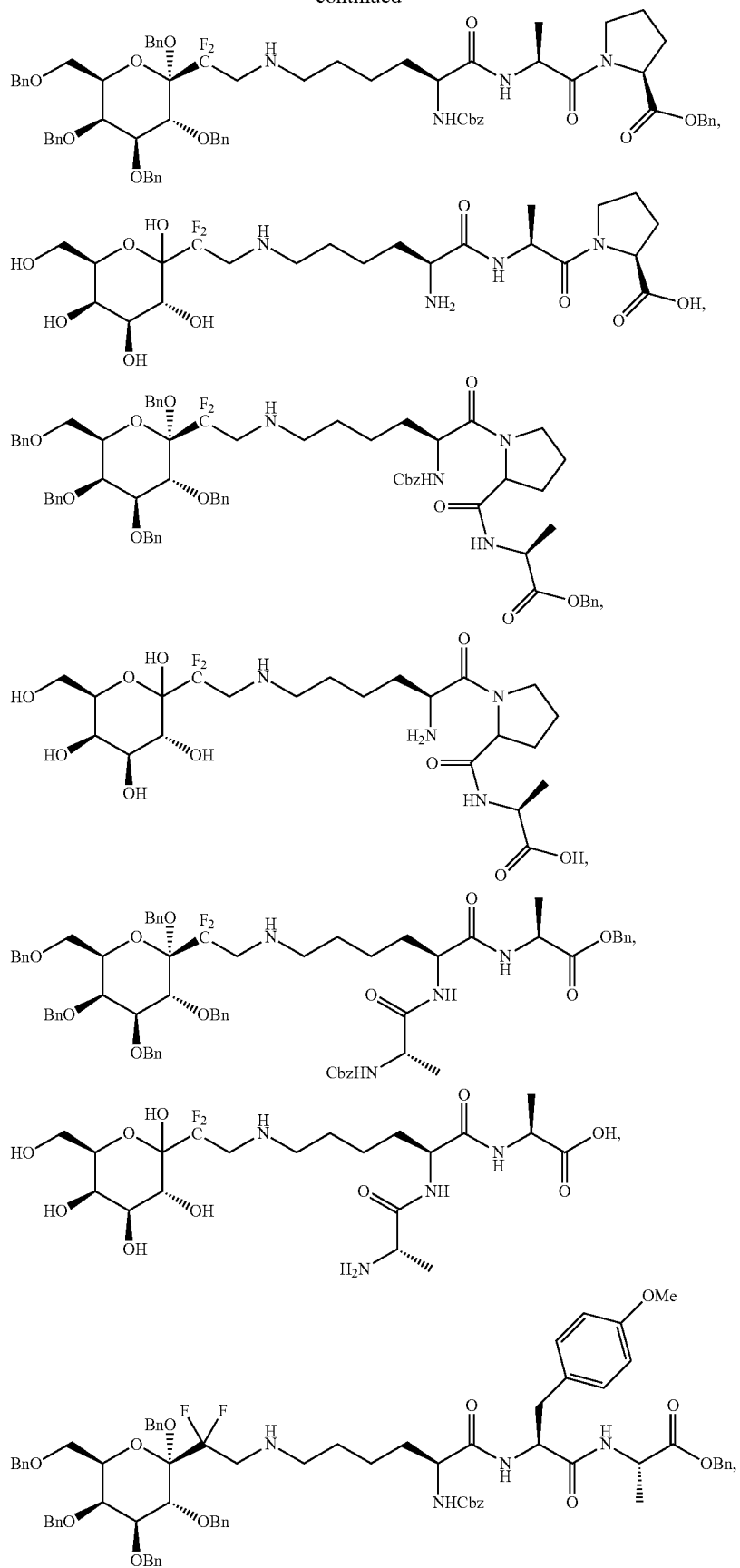

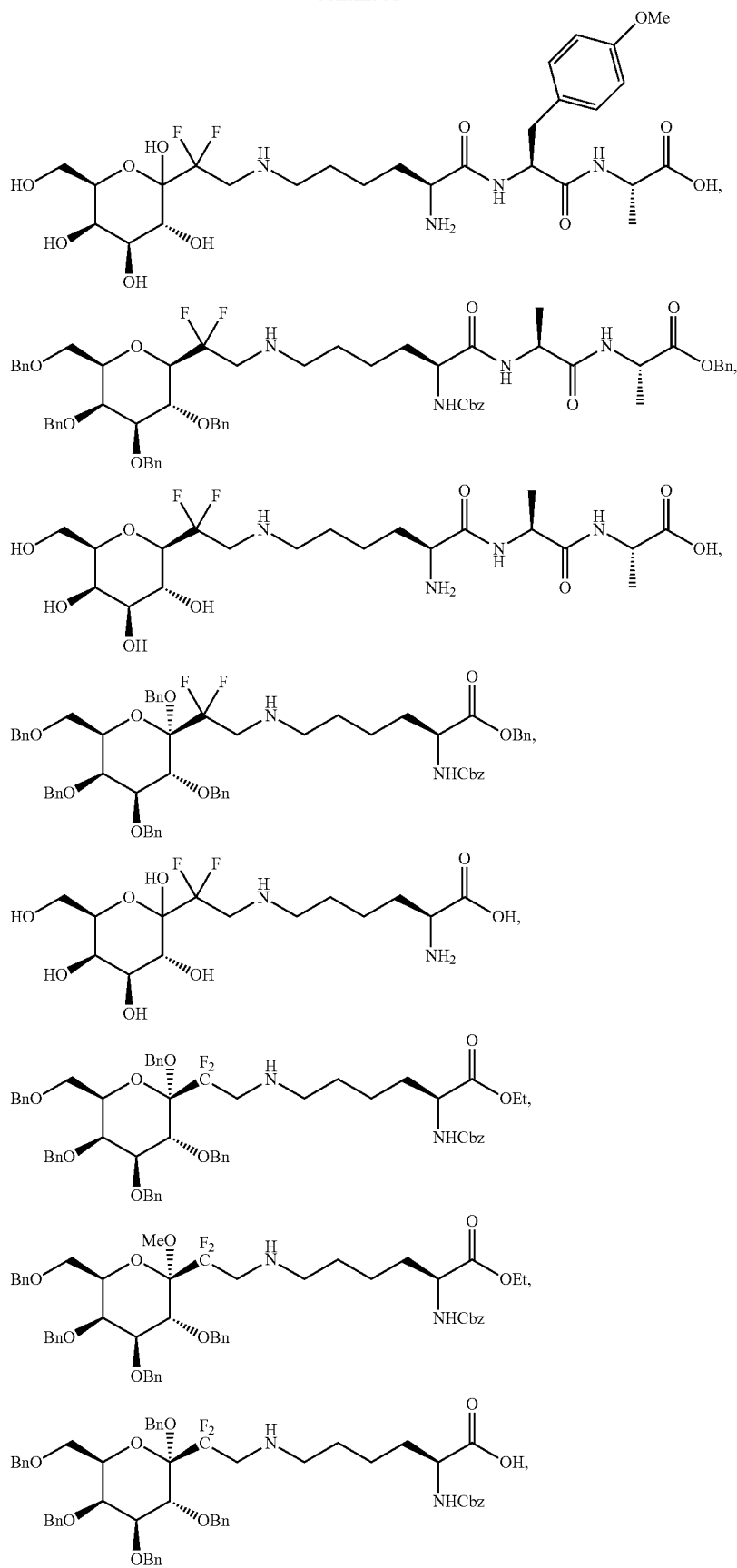

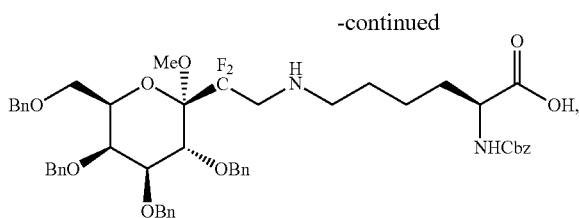

and salts and solvates thereof.

10. A culture, storage and/or preservation medium comprising at least one compound according to claim 1.

11. A cosmetic or dermatological composition comprising at least one compound according to claim 1 and at least one cosmetically or dermatologically acceptable excipient.

12. A process for preparing a compound of formula (I) according to claim 1 comprising the following successive steps:

(a) reducing the imine function of a compound of the following formula (II):

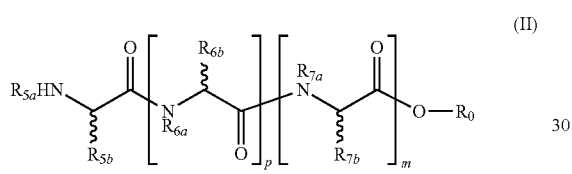 (II)

wherein:

R$_{5b}$, R$_{6b}$ and R$_{7b}$, are, independently from each other, a hydrogen; a (C$_1$-C$_6$)alkyl optionally substituted by a (C$_1$-C$_6$)alkoxy or a (C$_1$-C$_6$)thioalkoxy; an aryl; an aryl-(C$_1$-C$_6$)alkyl optionally substituted by a (C$_1$-C$_6$)alkoxy; or a group of the following formula:

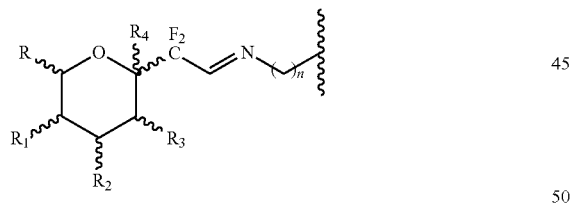

or R$_{5b}$ and R$_{5a}$ and/or R$_{6b}$ and R$_{6a}$ and/or R$_{7b}$ and R$_{7a}$ form, with the nitrogen and carbon atoms carrying them, a pyrrolidine cycle

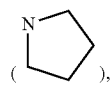

provided that at least one and only one group among R$_{5b}$, R$_{6b}$ and R$_{7b}$ when m=p=1, or at least one and only one group among R$_{5b}$ and R$_{6b}$ when m=0 and p=1, or at least one and only one group among R$_{5b}$ and R$_{7b}$ when m=1 and p=0, or R$_{5b}$ when m=p=0, is a group of formula:

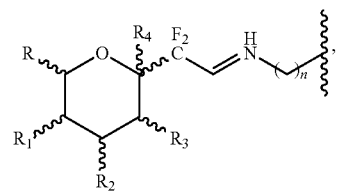

to obtain a compound of formula (I), and (b) optionally salifying or solvating the compound obtained in previous step (a) to obtain a salt or solvate of a compound of formula (I).

13. A process for preparing a compound of formula (I) according to claim 1 comprising the following successive steps:

(i) reacting a compound of the following formula (IX):

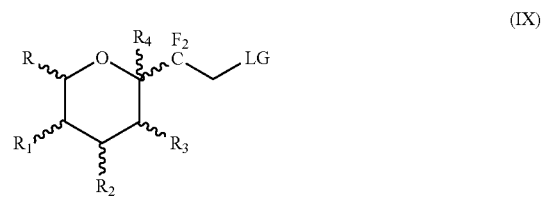 (IX)

wherein LG is a leaving group, with a compound of the following formula (III):

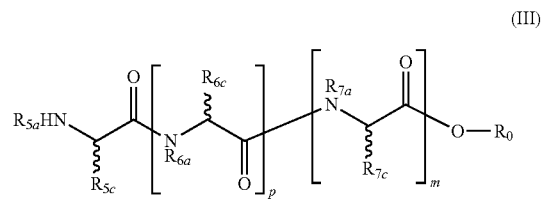 (III)

or a salt thereof, wherein:

R$_{5c}$, R$_{6c}$ and R$_{7c}$ are, independently from each other, a hydrogen; a (C$_1$-C$_6$)alkyl optionally substituted by a (C$_1$-C$_6$)alkoxy or a (C$_1$-C$_6$)thioalkoxy; an aryl; an aryl-(C$_1$-C$_6$)alkyl optionally substituted by a (C$_1$-C$_6$)alkoxy; or a group of the following formula:

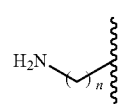

or $R_{5c}$ and $R_{5a}$ and/or $R_{6c}$ and $R_{6a}$ and/or $R_{7c}$ and $R_{7a}$ form, with the nitrogen and carbon atoms carrying them, a pyrrolidine cycle

provided that at least one and only one group among $R_{5c}$, $R_{6c}$ and $R_{7c}$ when m=p=1, or at least one and only one group among $R_{5c}$ and $R_{6c}$ when m=0 and p=1, or at least one and only one group among $R_{5c}$ and $R_{7c}$ when m=1 and p=0, or $R_{5c}$ when m=p=0, is a group of formula:

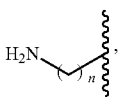

to obtain a compound of formula (I), and
(ii) optionally salifying or solvating the compound obtained in previous step (i) to obtain a salt or solvate of a compound of formula (I).

14. A process for preparing a compound of formula (I) according to claim 1 where m and p are not both 0 and $R_5$ is a group of the following formula:

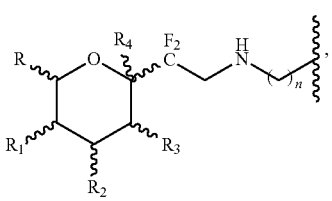

comprising the following successive steps:
(1) reacting a compound of the following formula (XIa):

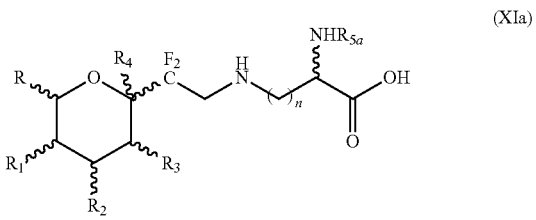

or a salt thereof,
with a compound of the following formula (VII)

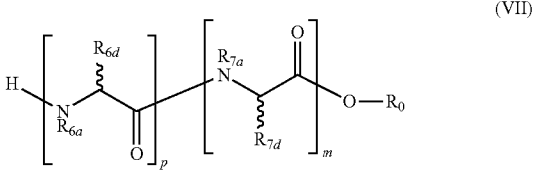

or a salt thereof,
provided that m and p are not both 0, and $R_{6d}$ and $R_{7d}$ are, independently of each other, a hydrogen; a ($C_1$-$C_6$)alkyl optionally substituted by a ($C_1$-$C_6$)alkoxy or a ($C_1$-$C_6$)thioalkoxy; an aryl; or an aryl-($C_1$-$C_6$)alkyl optionally substituted by a ($C_1$-$C_6$)alkoxy; or $R_{6d}$ and $R_{6a}$ and/or $R_{7d}$ and $R_{7a}$ form, with the nitrogen and carbon atoms carrying them, a pyrrolidine cycle

to obtain a compound of formula (I), and
(2) optionally salifying or solvating the compound obtained in previous step (1) to obtain a salt or solvate of a compound of formula (I).

15. A compound of formula (II), (VI) or (XI):

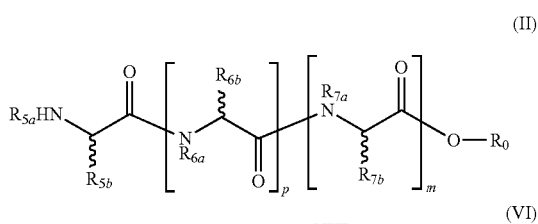

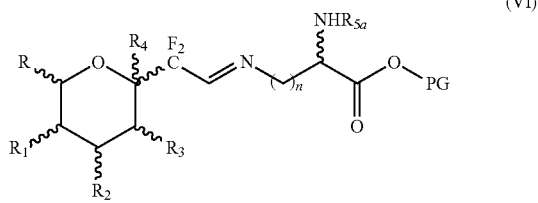

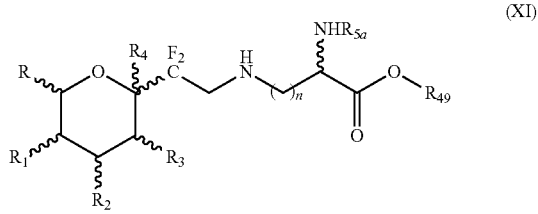

or a salt thereof, a solvate, a tautomer, a stereoisomer or a mixture of stereoisomers in any proportion,
wherein:
n is an integer from 1 to 6,
m is 0 or 1,
p is 0 or 1,
$R_0$ is a hydrogen atom, a O-protecting group or a ($C_1$-$C_6$)alkyl, ($C_2$-$C_6$)alkenyl, ($C_2$-$C_6$)alkynyl, ($C_3$-$C_7$)cycloalkyl, 5- to 7-membered heterocycloalkyl, aryl, heteroaryl, aryl-($C_1$-$C_6$)alkyl, heteroaryl-($C_1$-$C_6$)alkyl, ($C_1$-$C_6$)-alkyl-aryl or ($C_1$-$C_6$)-alkyl-heteroaryl group, this group being possibly substituted with one or more groups selected from a halogen atom, ($C_1$-$C_6$)alkoxy, OH, COOH and CHO,
R is a hydrogen or fluorine atom or a $CH_3$, $CH_2F$, $CH_2OSiR^{a1}R^{b1}R^{c1}$, $CH_2OR_8$, $CH_2OC(O)R_9$, $CH_2OCO_2R_{10}$, $CH_2OC(O)NR_{11}R_{12}$, $CH_2OP(O)(OR_{13})_2$ or $CH_2OSO_3R_{14}$ group,
$R_1$ and $R_2$ are, independently from one another, a fluorine atom or an $OSiR^{a2}R^{b2}R^{c2}$, $OR_{15}$, $OC(O)R_{16}$, $OCO_2R_{17}$, $OC(O)NR_{18}R_{19}$, $OP(O)(OR_{20})_2$ or $OSO_3R_{21}$ group, $R_3$ is a fluorine atom or an $OSiR^{a3}R^{b3}R^{c3}$, $OR_{22}$, $OC(O)R_{23}$, $OCO_2R_{24}$, $OCONR_{25}R_{26}$, $OP(O)(OR_{27})_2$, $OSO_3R_{28}$, $N_3$, phthalimidyl, $NR_{29}R_{30}$, $NR_{31}C(O)R_{32}$, $NR_{33}C(O)OR_{34}$, $N(C(O)R_{35})C(O)R_{36}$, $N(C(O)R_{37})C(O)OR_{38}$ or $N(C(O)OR_{39})C(O)OR_{40}$ group, $R_4$ is a hydrogen or halogen atom or an $OSiR^{a4}R^{b4}R^{c4}$, $OR_{41}$, $OC(O)R_{42}$, $OCO_2R_{43}$, $OCONR_{44}R_{45}$, $OP(O)(OR_{46})_2$, or $OSO_3R_{47}$ group, or R and $R_1$, together with the carbon atoms carrying them, form a cyclic acetal having the following formula:

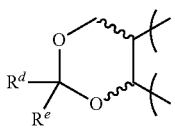

and/or ($R_1$ and $R_2$), ($R_2$ and $R_3$), and/or ($R_3$ and $R_4$), together with the carbon atoms carrying them, form a cyclic acetal having the following formula:

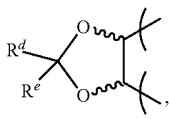

$R_{5a}$, $R_{6a}$ and $R_{7a}$ are, independently from each other, a hydrogen or a N-protecting group, $R_{5b}$, $R_{6b}$ and $R_{7b}$ are, independently from each other, a hydrogen; a $(C_1-C_6)$alkyl optionally substituted by a $(C_1-C_6)$alkoxy or a $(C_1-C_6)$thioalkoxy; an aryl; an aryl-$(C_1-C_6)$alkyl optionally substituted by a $(C_1-C_6)$alkoxy; or a group of the following formula:

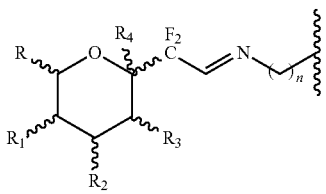

or $R_{5b}$ and $R_{5a}$ and/or $R_{6b}$ and $R_{6a}$ and/or $R_{7b}$ and $R_{7a}$ form, with the nitrogen and carbon atoms carrying them, a pyrrolidine cycle

provided that at least one and only one group among $R_{5b}$, $R_{6b}$ and $R_{7b}$ when m=p=1, or at least one and only one group among $R_{5b}$ and $R_{6b}$ when m=0 and p=1, or at least one and only one group among $R_{5b}$ and $R_{7b}$ when m=1 and p=0, or $R_{5b}$, when m=p=0, is a group of formula:

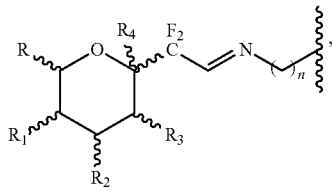

$R_8$, $R_{15}$, $R_{22}$ and $R_{41}$ are, independently from one another, a hydrogen atom, a O-protecting group or a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, aryl-$(C_1-C_6)$alkyl, heteroaryl-$(C_1-C_6)$alkyl, $(C_1-C_6)$-alkyl-aryl, $(C_1-C_6)$-alkyl-heteroaryl, saccharidic or polysaccharidic group, this group being optionally substituted with one or more groups selected from a halogen atom, $(C_1-C_6)$alkoxy, OH, COOH and CHO, $R_9$, $R_{10}$, $R_{16}$, $R_{17}$, $R_{23}$, $R_{24}$, $R_{32}$, $R_{34}$ to $R_{40}$, $R_{42}$ and $R_{43}$ are, independently from one another, a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, aryl-$(C_1-C_6)$alkyl, heteroaryl-$(C_1-C_6)$alkyl, $(C_1-C_6)$-alkyl-aryl or $(C_1-C_6)$-alkyl-heteroaryl group, this group being optionally substituted with one or more groups selected from a halogen atom, $(C_1-C_6)$alkoxy, OH, COOH and CHO, $R_{11}$, $R_{12}$, $R_{18}$, $R_{19}$, $R_{25}$, $R_{26}$, $R_{29}$ to $R_{31}$, $R_{33}$, $R_{44}$ and $R_{45}$ are, independently from one another, a hydrogen atom or a $(C_1-C_6)$alkyl, $(C_2-C_6)$alkenyl, $(C_2-C_6)$alkynyl, aryl, heteroaryl, aryl-$(C_1-C_6)$alkyl, heteroaryl-$(C_1-C_6)$alkyl, $(C_1-C_6)$-alkyl-aryl or $(C_1-C_6)$-alkyl-heteroaryl group, this group being optionally substituted with one or more groups selected from a halogen atom, $(C_1-C_6)$alkoxy, OH, COOH and CHO, $R_{13}$, $R_{14}$, $R_{20}$, $R_{21}$, $R_{27}$, $R_{28}$, $R_{46}$ and $R_{47}$ are, independently from one another, a hydrogen atom or a $(C_1-C_6)$alkyl group, $R_{49}$ is H or a O-protecting group, $R^{a1}$ to $R^{a4}$, $R^{b1}$ to $R^{b4}$ and $R^{c1}$ to $R^{c4}$, are, independently from one another, a $(C_1-C_6)$alkyl, aryl or aryl-$(C_1-C_6)$alkyl group, $R^d$ and $R^e$ are, independently from one another, a hydrogen atom or a $(C_1-C_6)$alkyl group, and PG is a O-protecting group.

16. The compound according to claim 1, wherein:

$R_8$, $R_{11}$, $R_{12}$, $R_{15}$, $R_{18}$, $R_{19}$, $R_{22}$, $R_{25}$, $R_{26}$, $R_{29}$ to $R_{31}$, $R_{33}$, $R_{41}$, $R_{44}$ and $R_{45}$ are a hydrogen atom or a $(C_1-C_6)$alkyl, aryl or aryl-$(C_1-C_6)$alkyl group, this group being possibly substituted with one or more groups selected from a halogen atom, $(C_1-C_6)$alkoxy, OH, COOH and CHO, and $R_9$, $R_{10}$, $R_{16}$, $R_{17}$, $R_{23}$, $R_{24}$, $R_{32}$, $R_{34}$ to $R_{40}$, $R_{42}$ and $R_{43}$ are a $(C_1-C_6)$alkyl, aryl or aryl-$(C_1-C_6)$alkyl group, this group being possibly substituted with one or more groups selected from a halogen atom, $(C_1-C_6)$alkoxy, OH, COOH and CHO.

17. The compound according to claim 4 wherein

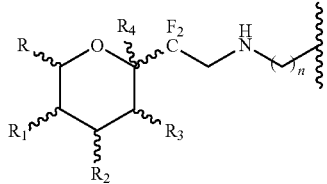

has the following configuration:

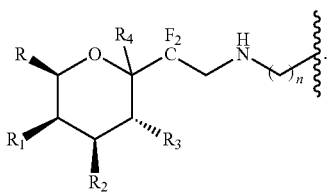

18. A method of preservation and/or protection of a biological material or of a microorganism comprising placing said biological material or microorganism in a medium containing a compound according to claim 1.

19. The method according to claim 18, wherein the biological material is selected from cells, tissues, body fluids and organs.

20. A method for anti-aging, skin protection or skin regeneration comprising applying to the skin of a person in need thereof of an affective amount of a compound according to claim 1.

* * * * *